(12) United States Patent
Xie

(10) Patent No.: US 10,245,043 B2
(45) Date of Patent: Apr. 2, 2019

(54) SURGICAL DRILL HAVING A BRAKE THAT, UPON THE DRILL BIT PENETRATING THROUGH BONE, PREVENTS FURTHER INSERTION OF THE DRILL

(71) Applicant: Stryker Corporation, Kalamazoo, MI (US)

(72) Inventor: Mark M. Xie, Kalamazoo, MI (US)

(73) Assignee: STRYKER CORPORATION, Kalamazoo, MI (US)

( * ) Notice: Subject to any disclaimer, the term of this patent is extended or adjusted under 35 U.S.C. 154(b) by 239 days.

(21) Appl. No.: 14/991,224

(22) Filed: Jan. 8, 2016

(65) Prior Publication Data

US 2016/0120553 A1 May 5, 2016

Related U.S. Application Data

(63) Continuation of application No. PCT/US2014/045702, filed on Jul. 8, 2014.
(Continued)

(51) Int. Cl.
*A61B 17/16* (2006.01)
*A61B 90/00* (2016.01)
*A61B 17/00* (2006.01)

(52) U.S. Cl.
CPC ........ *A61B 17/1633* (2013.01); *A61B 17/162* (2013.01); *A61B 17/1624* (2013.01);
(Continued)

(58) Field of Classification Search
CPC . A61B 17/16; A61B 17/1613; A61B 17/1615; A61B 17/162; A61B 17/1622;
(Continued)

(56) References Cited

U.S. PATENT DOCUMENTS 3,897,166 A 7/1975 Adams
4,688,970 A 8/1987 Eckman
(Continued)

FOREIGN PATENT DOCUMENTS

EP 0512867 A2 11/1992
EP 0343622 B1 4/1995
(Continued)

OTHER PUBLICATIONS

International Search Report for Application No. PCT/US2014/045702 dated Feb. 12, 2014, 4 pages.
(Continued)

*Primary Examiner* — Si Ming Ku
*Assistant Examiner* — Diana S Jones
(74) *Attorney, Agent, or Firm* — Howard & Howard Attorneys PLLC

(57) ABSTRACT

A surgical drill for use with a drill bit. The drill includes a handpiece with a motor and a brake mechanism. The brake mechanism is a sliding rack adjacent a first end and a second end with a stop adjacent the drill bit. An actuator is mounted to the handpiece and a plunger is coupled to the actuator. A sensor asserts a signal when the drill bit penetrates bone. When the sensor asserts the signal indicting the drill bit penetrated bone, the actuator moves the plunger into engagement with the rack to prevent further insertion of the drill bit.

11 Claims, 80 Drawing Sheets

Related U.S. Application Data

(60) Provisional application No. 61/844,132, filed on Jul. 9, 2013.

(52) U.S. Cl.
CPC ...... *A61B 17/1626* (2013.01); *A61B 17/1628* (2013.01); *A61B 90/03* (2016.02); *A61B 2017/0003* (2013.01); *A61B 2017/00022* (2013.01); *A61B 2017/0042* (2013.01); *A61B 2017/00199* (2013.01); *A61B 2017/00398* (2013.01); *A61B 2017/00407* (2013.01); *A61B 2017/00991* (2013.01); *A61B 2090/035* (2016.02); *A61B 2090/036* (2016.02)

(58) Field of Classification Search
CPC ............ A61B 17/1624; A61B 17/1626; A61B 17/1628; A61B 17/1633; A61B 17/17; A61B 17/1717; A61B 17/1725; A61B 90/03; A61B 2090/033; A61B 2090/035; A61B 2090/036

See application file for complete search history.

(56) References Cited

U.S. PATENT DOCUMENTS

| | | | |
|---|---|---|---|
| 5,071,293 A | | 12/1991 | Wells |
| 6,033,409 A * | | 3/2000 | Allotta ............... A61B 17/1622 606/170 |
| 6,162,226 A | | 12/2000 | DeCarlo, Jr. et al. |
| 6,336,931 B1 | | 1/2002 | Hsu et al. |
| 6,665,948 B1 | | 12/2003 | Kozin et al. |
| 7,188,431 B2 | | 3/2007 | Herrmann et al. |
| 7,638,958 B2 | | 12/2009 | Philipp et al. |
| 8,463,421 B2 | | 6/2013 | Brett et al. |
| 8,511,945 B2 | | 8/2013 | Apkarian et al. |
| 8,821,493 B2 | | 9/2014 | Anderson |
| 8,894,654 B2 | | 11/2014 | Anderson |
| 8,926,614 B2 | | 1/2015 | Hsieh |
| 8,970,207 B2 | | 3/2015 | Baumgartner |
| 9,186,156 B2 | | 11/2015 | Xie |
| 9,193,022 B1 | | 11/2015 | Janicki |
| 9,204,885 B2 | | 12/2015 | McGinley et al. |
| 2005/0116673 A1* | | 6/2005 | Carl ................... A61B 17/1626 318/432 |
| 2009/0245956 A1* | | 10/2009 | Apkarian ........... A61B 17/1626 408/1 R |
| 2009/0326537 A1 | | 12/2009 | Anderson |
| 2011/0245833 A1* | | 10/2011 | Anderson .......... A61B 17/1626 606/80 |
| 2013/0245629 A1 | | 9/2013 | Xie |
| 2013/0245833 A1 | | 9/2013 | McKibben et al. |
| 2015/0148596 A1* | | 5/2015 | Gitman ................. A61B 90/35 600/104 |
| 2016/0128704 A1 | | 5/2016 | McGinley et al. |

FOREIGN PATENT DOCUMENTS

| | | |
|---|---|---|
| WO | 0067645 A1 | 11/2000 |
| WO | 2007142830 A2 | 12/2007 |
| WO | 2009158115 A1 | 12/2009 |
| WO | 2016036756 A1 | 3/2016 |

OTHER PUBLICATIONS

English language abstract and machine-assisted English translation for WO 00/67645 extracted from espacenet.com database on Jan. 17, 2018, 9 pages.

* cited by examiner

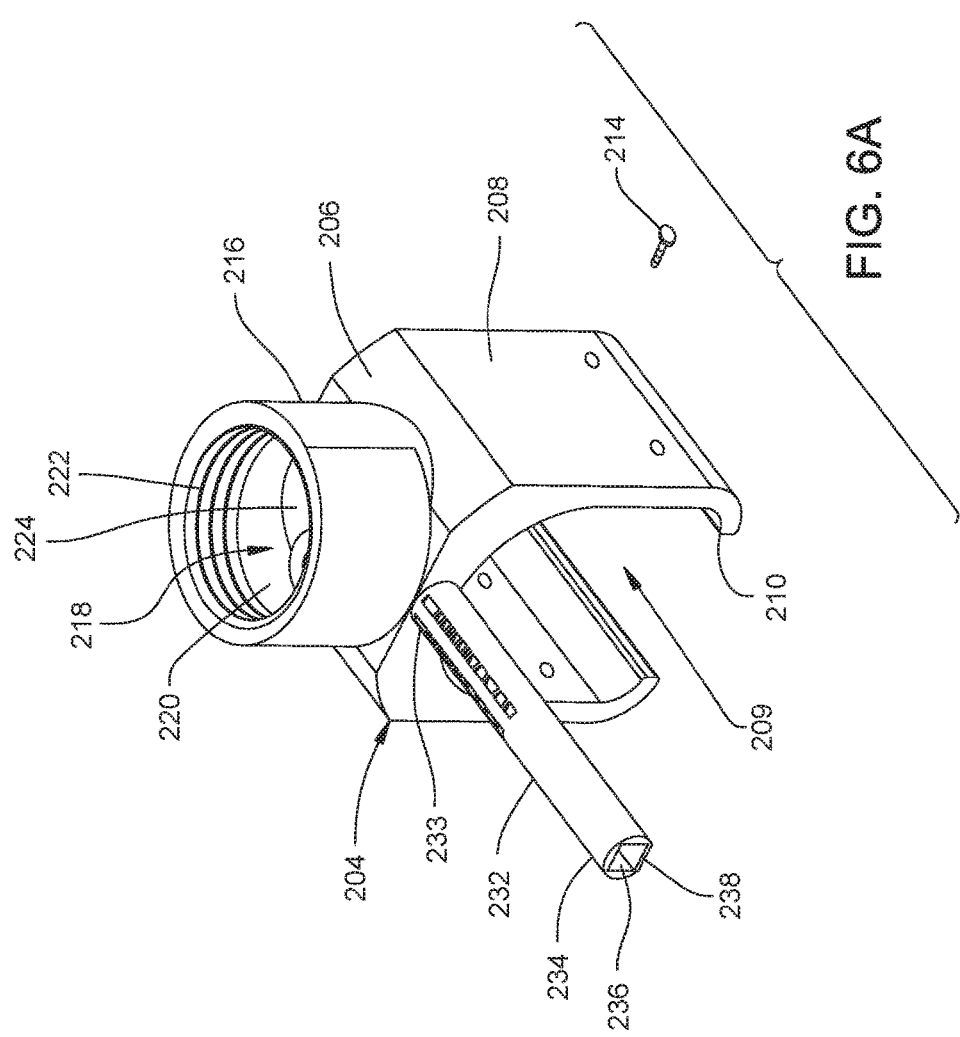

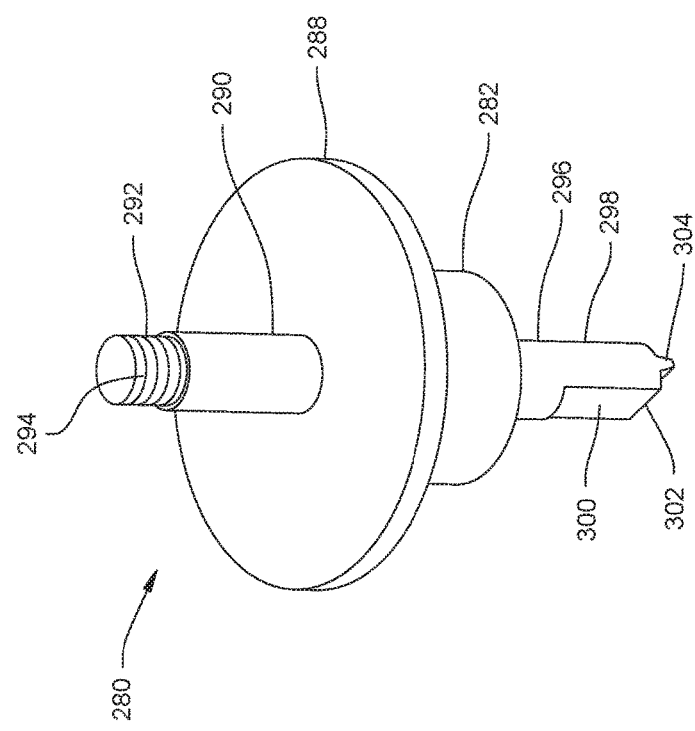

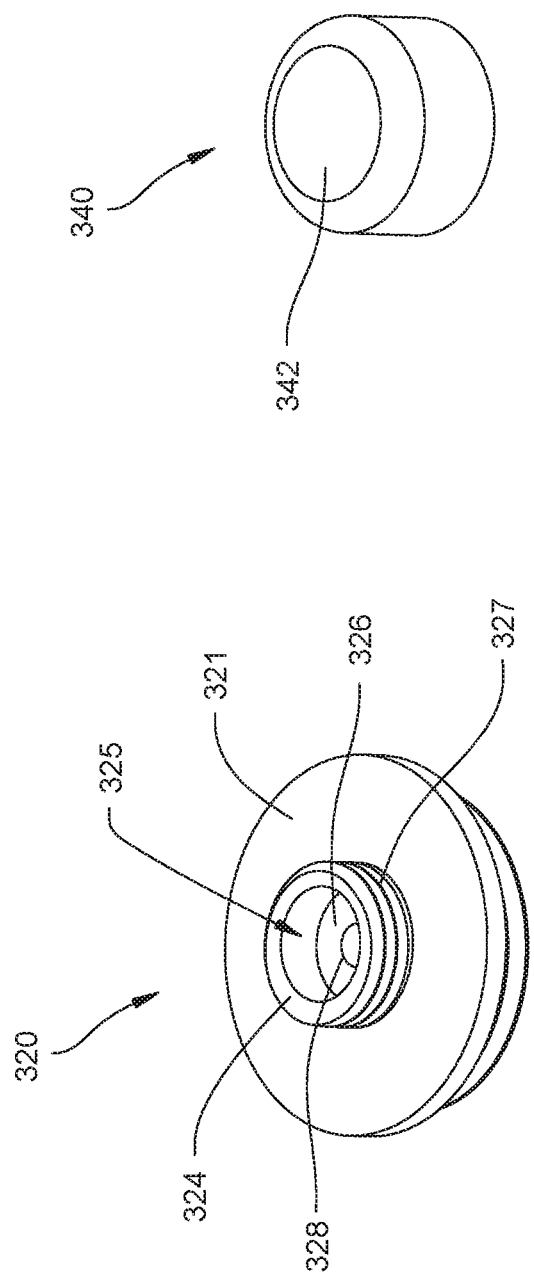

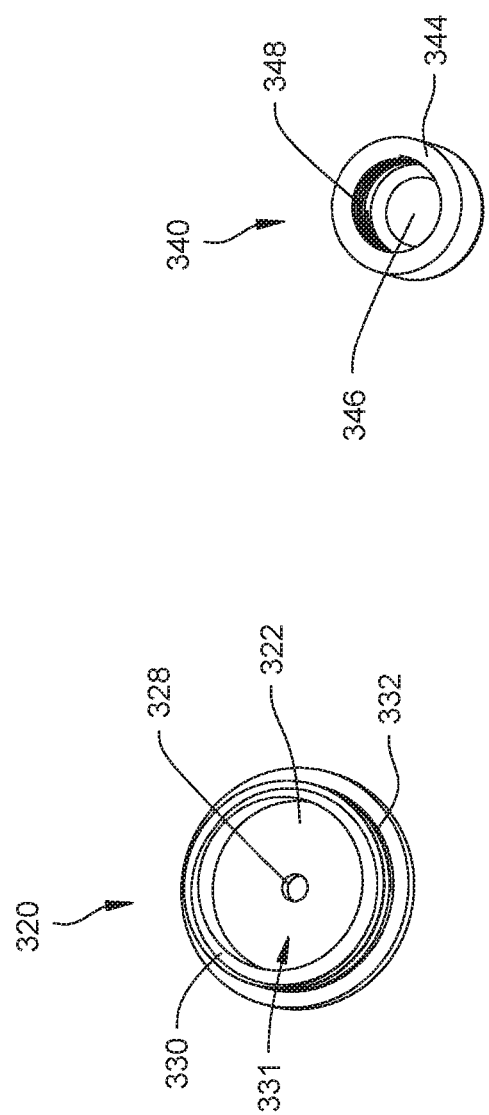

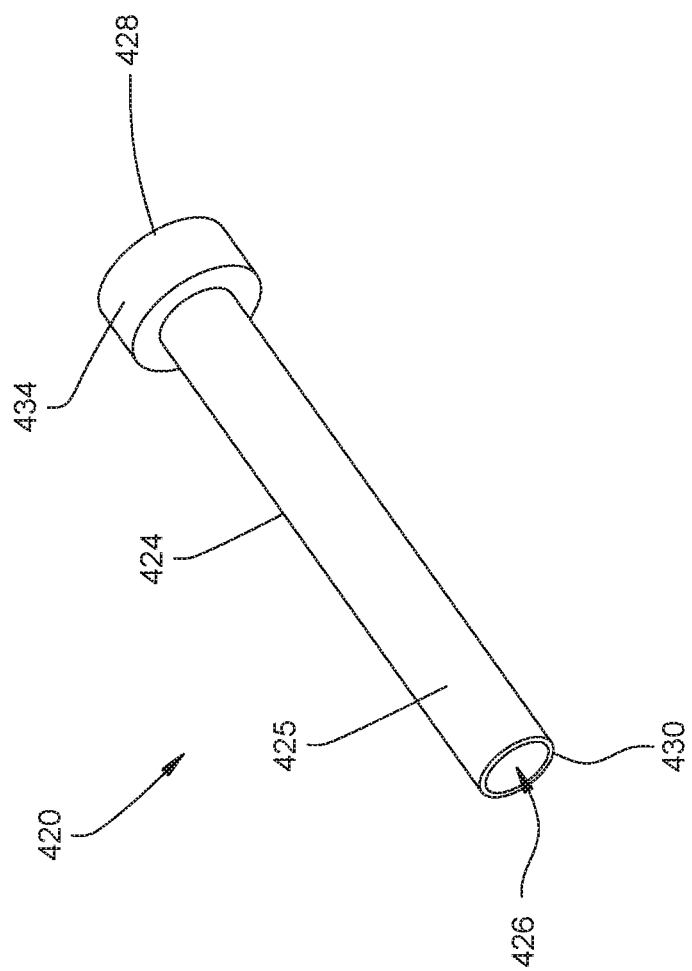

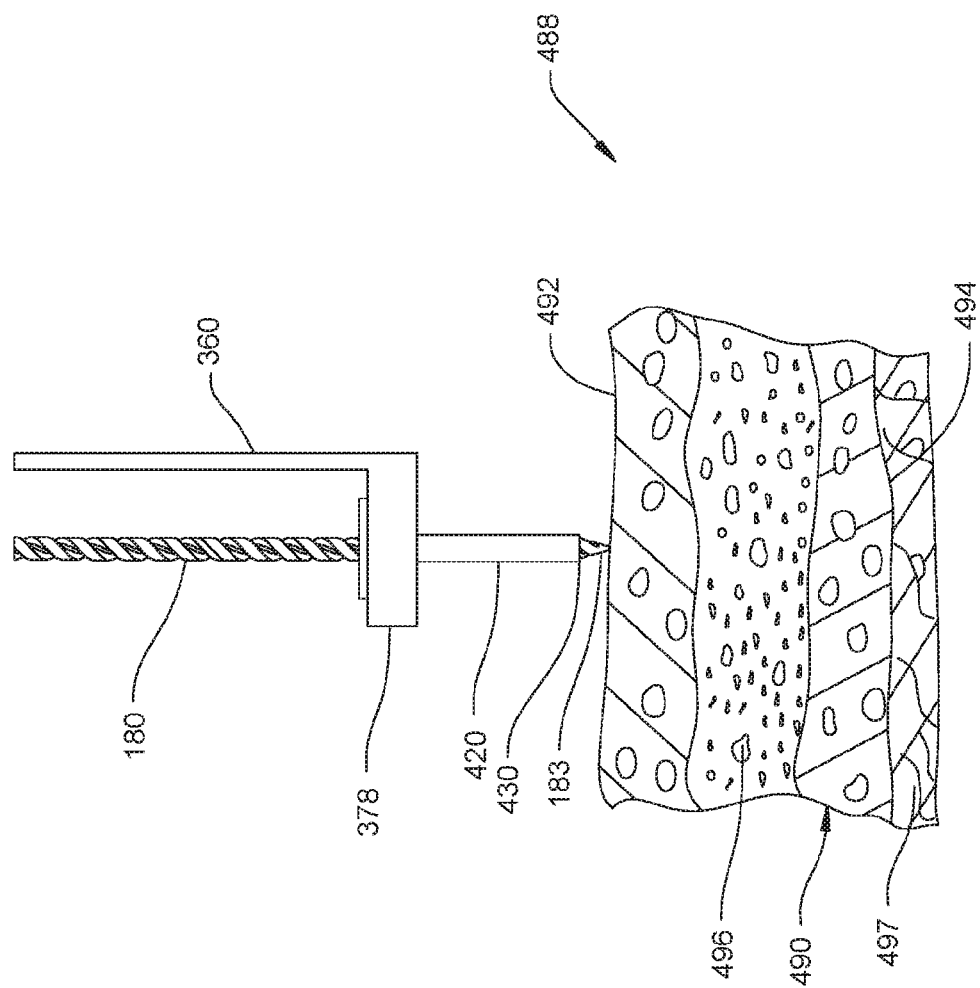

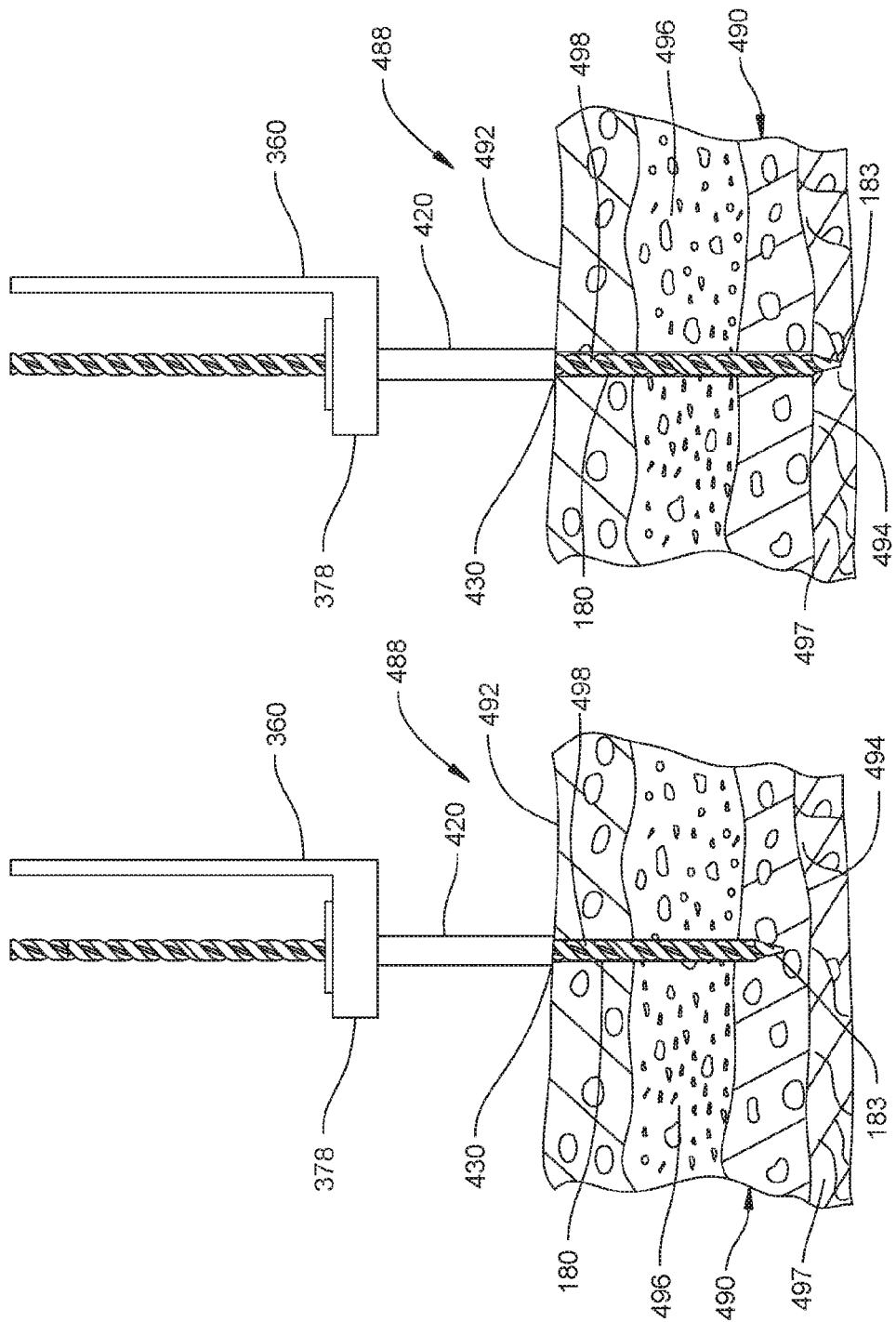

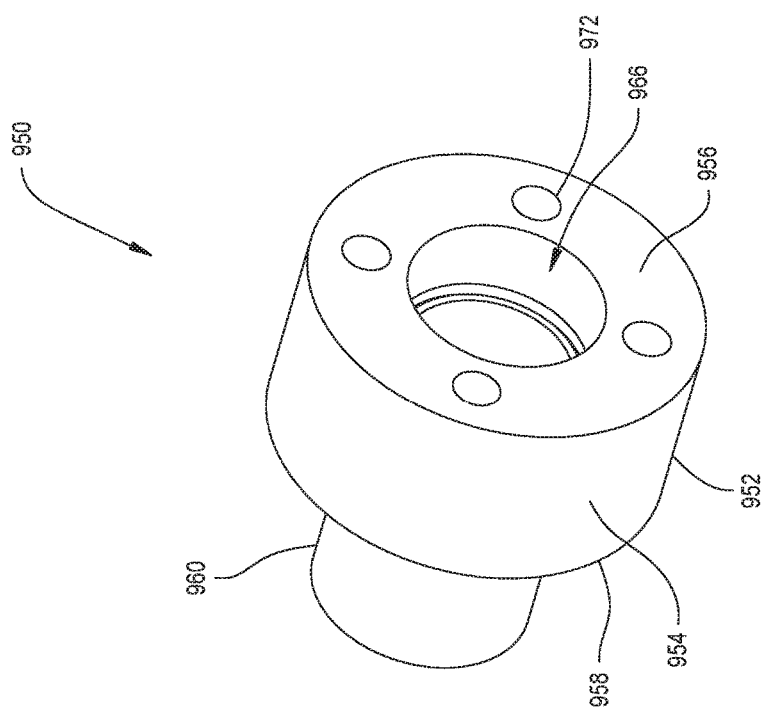

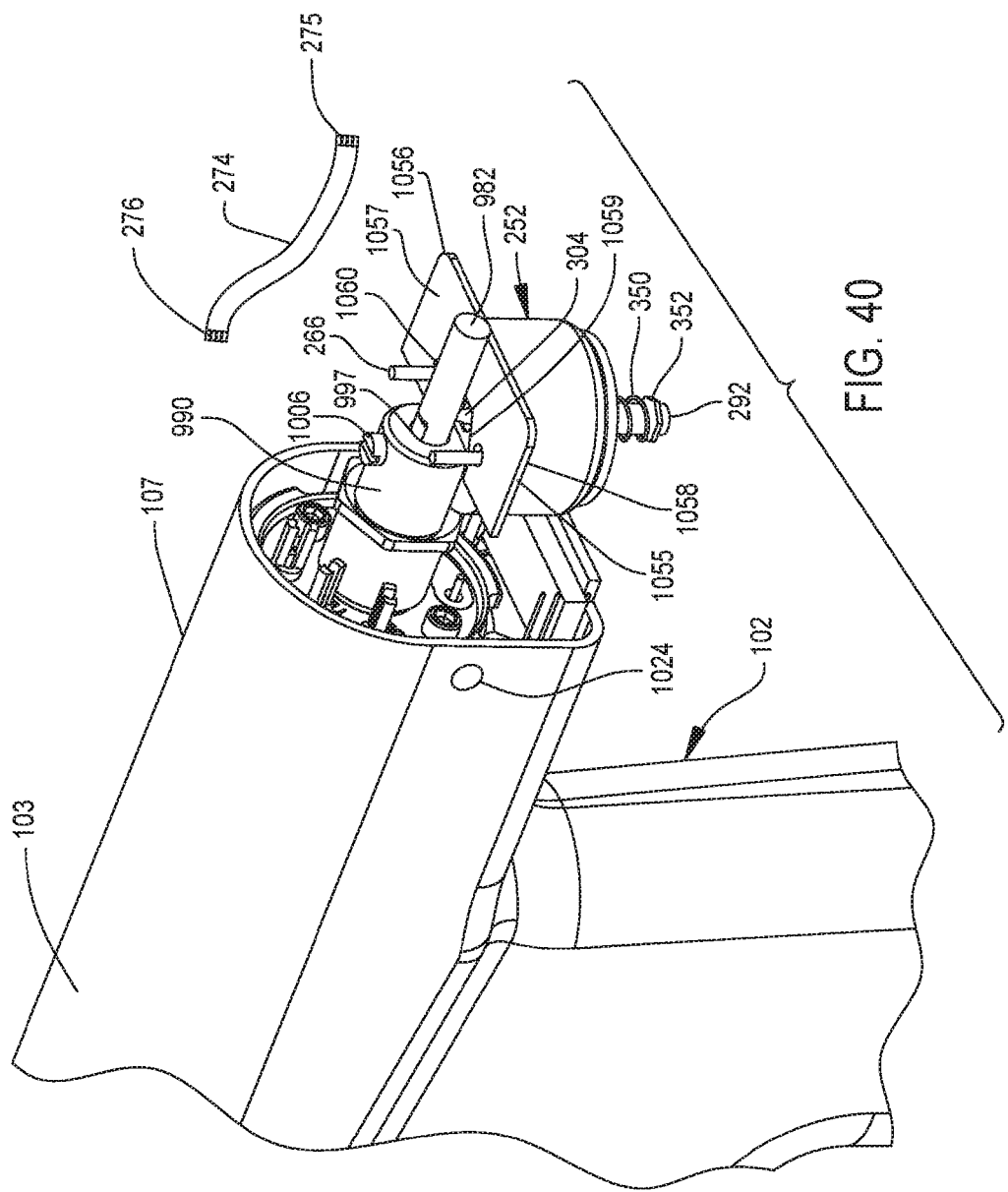

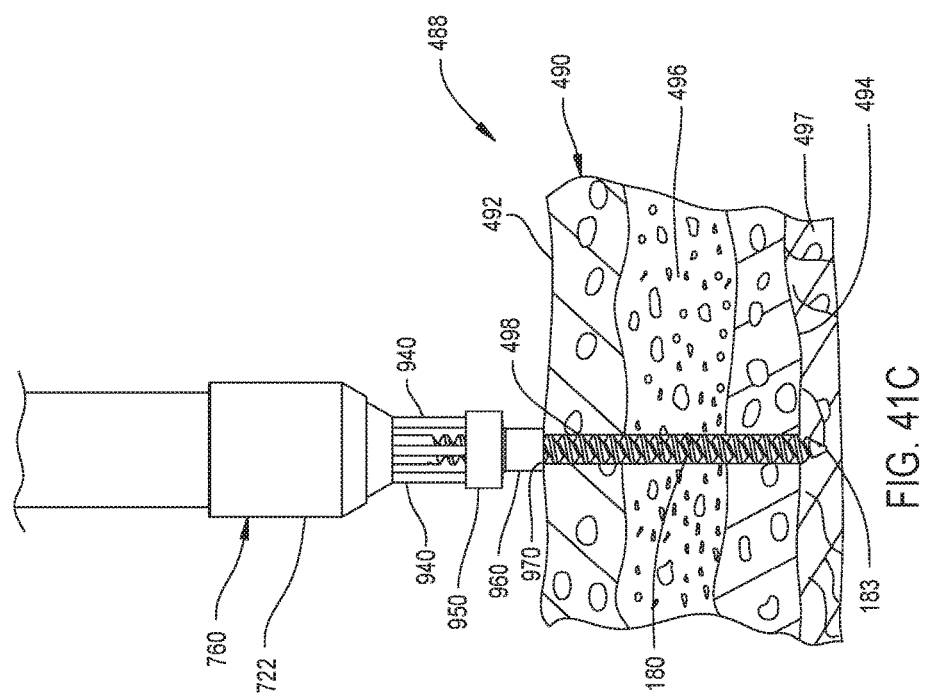

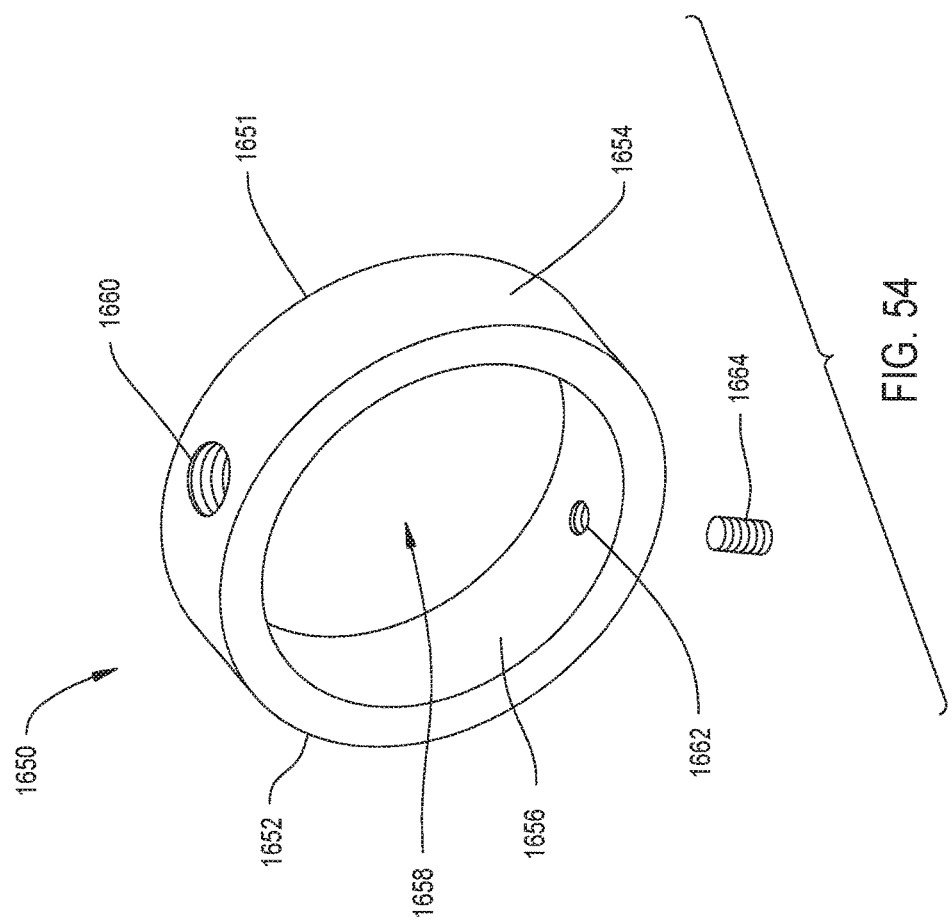

SURGICAL DRILL HAVING A BRAKE THAT, UPON THE DRILL BIT PENETRATING THROUGH BONE, PREVENTS FURTHER INSERTION OF THE DRILL

FIELD OF THE INVENTION

This invention relates generally to surgical drills used to form a bore in a bone. More particularly, the surgical drill of the present invention has a brake mechanism that upon the drill bit penetrating through the bone, prevents further insertion of the drill bit.

BACKGROUND OF THE INVENTION

In modern surgery, one of the most important instruments available to medical personnel is the powered surgical drill. Typically, this drill comprises a housing in which a motor is secured called a handpiece. The motor has a shaft that is connected to some type of chuck or other coupling assembly that is mounted to the housing. The coupling assembly holds a cutting accessory that is applied to the patient in order to perform a specific medical procedure. Some common cutting accessories are drill bits, burs and reamers. These accessories are used to drill into and/or separate sections of soft tissue and hard tissue, commonly referred to as bone. The ability to use surgical drills to actuate these and other cutting accessories has lessened the physical strain of physicians and other medical personnel that perform these medical procedures. Moreover, most surgical procedures can be performed more quickly and more accurately with powered surgical tools than with the manual equivalents that preceded them.

Surgical drills are often used in certain orthopedic surgical procedures in order to facilitate the repair of fractured and broken bones. These fractures and breaks typically occur as a result of trauma to the bone. In this type of procedure it is common practice to fit a pin or screw to the adjacent sections of the bone so as to hold these sections together. In this type of procedure, the drill is used to form a bore/hole/holes in the section/sections of the bone into which the pin or screw is to be fitted.

In this type of procedure, the drill bit, while it should extend through the bone, should not be pressed to extend beyond the bone. This is because if the tip of the drill bit, presses through the bone, the tip could damage the soft tissue adjacent the opposite side of the bone. This damage is more likely to occur if the tip, when pressed against the soft tissue, is rotating.

Accordingly, when a surgeon is forming a bore in a bone in order to set a pin or a screw, the surgeon must typically use extreme care to ensure that, as soon as possible after the drill bit tip penetrates the bone, the drill is deactivated.

One means suggested to reduce the extent to which a rotating drill bit is allowed to press into soft tissue adjacent a bone is to provide trauma surgeons with drills similar to the cranial perforators used by neurosurgeons. A cranial perforator is a drill used by a neurosurgeon to form the initial entrance opening into the skull. A cranial perforator includes a head and inner and outer drills. The inner drill is in the form of a solid cylinder. The outer drill is in the form of a sleeve that extends circumferentially around the inner drill. Both drill bits extend from the head. The head is attached to handpiece with a motor. Internal to both the head and the drill bits are features that, when engaged, cause the drill bits to rotate with the rotation of the head. Also, internal to the head is a spring. The spring normally holds at least one of the drills away from the complementary features integral with the head. When the drill bits are pressed against bone, the resistance of the bone pushes the drill bit and head features into engagement. When the perforator is in this state, the rotation of the head results in a like rotation of the drills. The rotational moment and forward force of the drills causes the drills to form the desired bore. When at least one of the drills, typically the inner drill, completely penetrates the skull, the skull no longer offers resistance to the release action of the spring. The spring pushes the drills away from the head. Thus, when the perforator is in this state, the rotation of the head does not cause a like rotation of the drills. Since the drills are not rotating when the perforator is in the this state, the pressing of the drills against the tissue, the thin soft tissue below the skull does not result in appreciable damage to this tissue.

One reason cranial perforators work well for forming bores in the skull is that the skull is relatively thin. Typically the skull has a thickness of 1.5 cm or less. Thus, once the bore is formed, the surgeon, with using only a minimal amount of force, can pull the perforator out of the newly formed bore.

In trauma surgeries and other orthopedic surgeries the surgeon may want to form a bore hole in bone that is relatively thick, having a thickness of 3.0 cm or more. Owing to the tight fit of the drill bit in the bore, it is rather difficult to simply pull the bit out of the bone. If a medical practitioner uses a large amount of manual force, there is the possibility that if they use this back force, especially if coupled with a back and forth prying action, can damage the bone.

To avoid the possibility of this post bore formation bone damage, an orthopedic surgeon typically drives the drill bit in reverse in order to facilitate the backing out of the bit from the bore. However, as mentioned above, once the drills of a cranial perforator penetrate the bone, they are disengaged from the complementary head. Driving the head in reverse does not foster a like rotational movement of the drills. This is why cranial perforators, while useful for preventing damage to the tissue underlying the bone against which they are pressed, have not proven particularly suitable for forming the relatively deep bores required by orthopedic surgeons.

Another problem with the use of cranial perforators is that during the formation of a bore, the drill bit may disengage from the motor before the bore is completely formed. The orthopedic surgeon may need to remove the drill and then re-drill the bore again to complete the formation of the bore.

The Inventor's U.S. patent application Ser. No. 13/798, 866, filed 13 Mar. 2013, now US Pat. Pub. No. US 2013/ 0245629 A1, the contents of which are hereby incorporated by reference, discloses a perforator like device for drilling into bone where a clutch mechanism both prevents overdrilling and allows the drill bit to be driven in the reverse direction. A limitation of this device is that it requires a bit assembly that includes inner and outer bits. Many orthopedic surgeons prefer working with a bit assembly that consists of a single drill bit.

An additional issue faced by orthopedic surgeons is that it is difficult and time consuming during surgery to use the current depth gauges to determine the depth of a bone bore. Current depth gauges use a piece of wire with a hook to try and measure the depth of the bore. The wire and hook is placed through the bone bore and moved until the hook catches on the bone adjacent the bottom of the bore. The surgeon places their finger on the wire adjacent the bore and removes the wire from the bore. The distance between the surgeon's finger and the hook represents the depth of the bore.

Unfortunately, if the surgeon's finger is placed incorrectly or slips, the measurement will be incorrect. Also, when the hook extends through the bone bore and out from the bottom of the bore, adjacent tissues can be subject to damage.

SUMMARY OF THE INVENTION

This invention is related to a new and useful surgical drill assembly used to form a bore in a bone. The surgical drill assembly has a brake mechanism that, upon the drill bit penetrating through the bone, prevents further insertion of the drill bit.

The surgical drill assembly includes a handpiece having a case and a rotary motor mounted within the case. A chuck is coupled to the motor. The chuck receives the drill bit. A brake mechanism is coupled to the case. The brake mechanism includes a rack with a first end and a second end. The first end of the rack is coupled to the case for sliding movement relative to the case and the second end has a protector that surrounds the drill bit. An actuator is coupled to the case. A plunger is coupled to the actuator and is positioned to be engaged and disengaged with the rack. A sensor is coupled to the handpiece and is configured to sense a first parameter associated with the motor or the drill bit. A controller is in communication with the motor, the actuator and the sensor. In response to the first parameter being greater than a pre-determined threshold, the controller causes the actuator to move the plunger into engagement with the rack preventing further insertion of the drill bit.

The drill assembly of this invention is designed for use with a bit assembly only includes a single piece drill bit.

BRIEF DESCRIPTION OF THE DRAWINGS

The invention is pointed out with particularity in the claims. The above and further features and advantages of this invention are understood from the following Detailed Description taken in conjunction with the accompanying drawings in which:

FIG. 6A is a perspective view of the brake mechanism housing;

FIG. 8A is a perspective view of the brake mechanism plunger;

FIG. 9A is a top perspective view of the brake mechanism cover;

FIG. 9B is a bottom perspective view of the brake mechanism cover;

FIG. 10A is a top perspective view of the brake mechanism cap;

FIG. 10B is a bottom perspective view of the brake mechanism cap;

FIG. 12B is a top perspective view of the tissue protector;

FIG. 14A is a side cross-sectional view of the tissue protector and drill bit of FIG. 1 prior to the start of drilling into a bone;

FIG. 14B is a side cross-sectional view of the tissue protector and drill bit of FIG. 1 during formation of a bone bore in a bone;

FIG. 14C is a side cross-sectional view of the tissue protector and drill bit of FIG. 1 after the drill bit has penetrated through the bone;

FIG. 35B is a rear perspective view of the tissue protector;

FIG. 40 is a rear perspective view of the rotary surgical drill of FIG. 26 with the brake housing removed showing the relative orientation of the linear actuator and the rack;

FIG. 41C is a side cross-sectional view of the tissue protector and drill bit of FIG. 26 after the drill bit has penetrated through the bone;

FIG. 54 is a front perspective view of the release ring;

DETAILED DESCRIPTION

I. Handpiece

Figure 1:
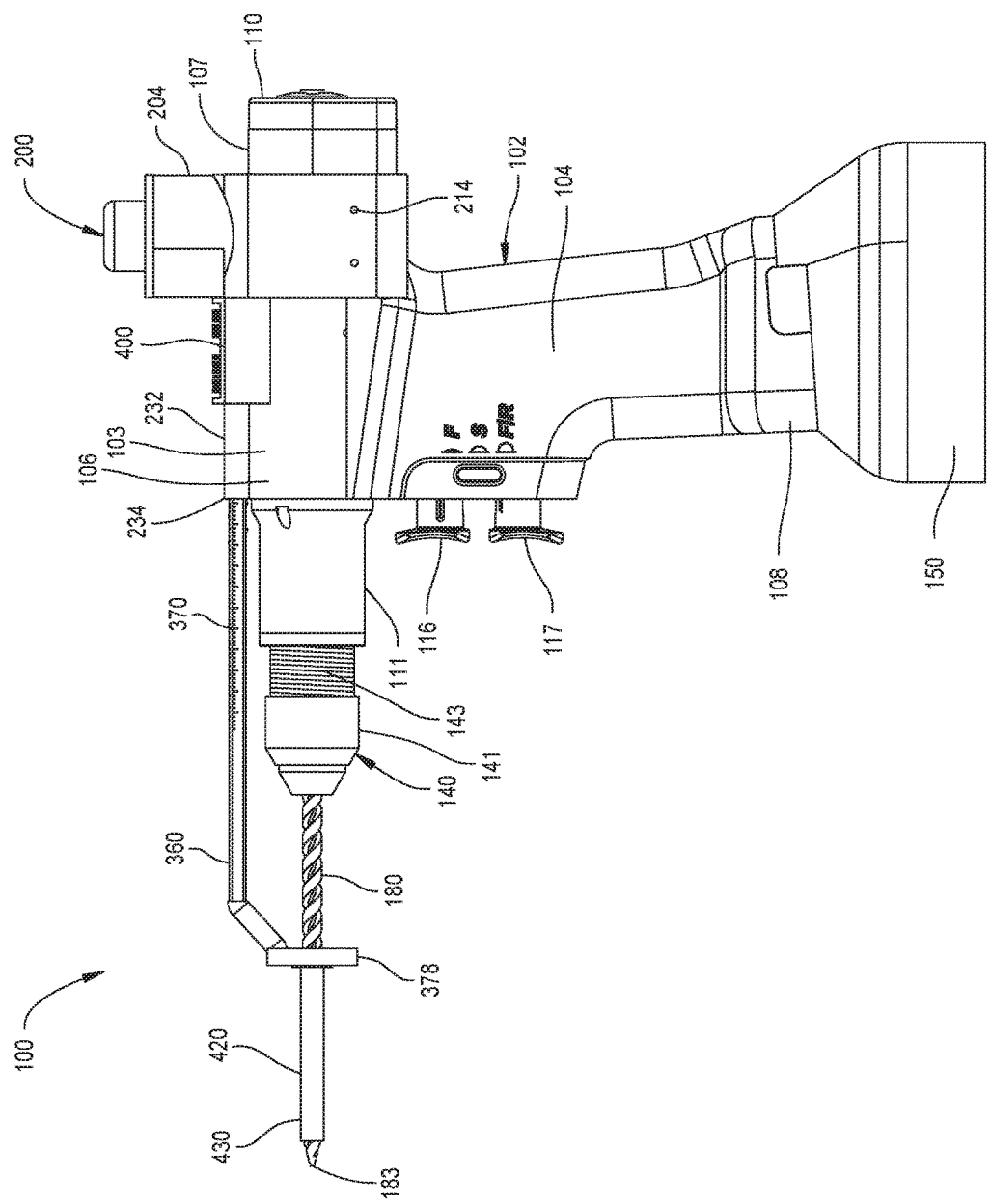
FIG. 1 is an overall side view of a powered rotary surgical drill having a top mounted brake mechanism with an external telescoping rack in accordance with the present invention.
Figure 2:
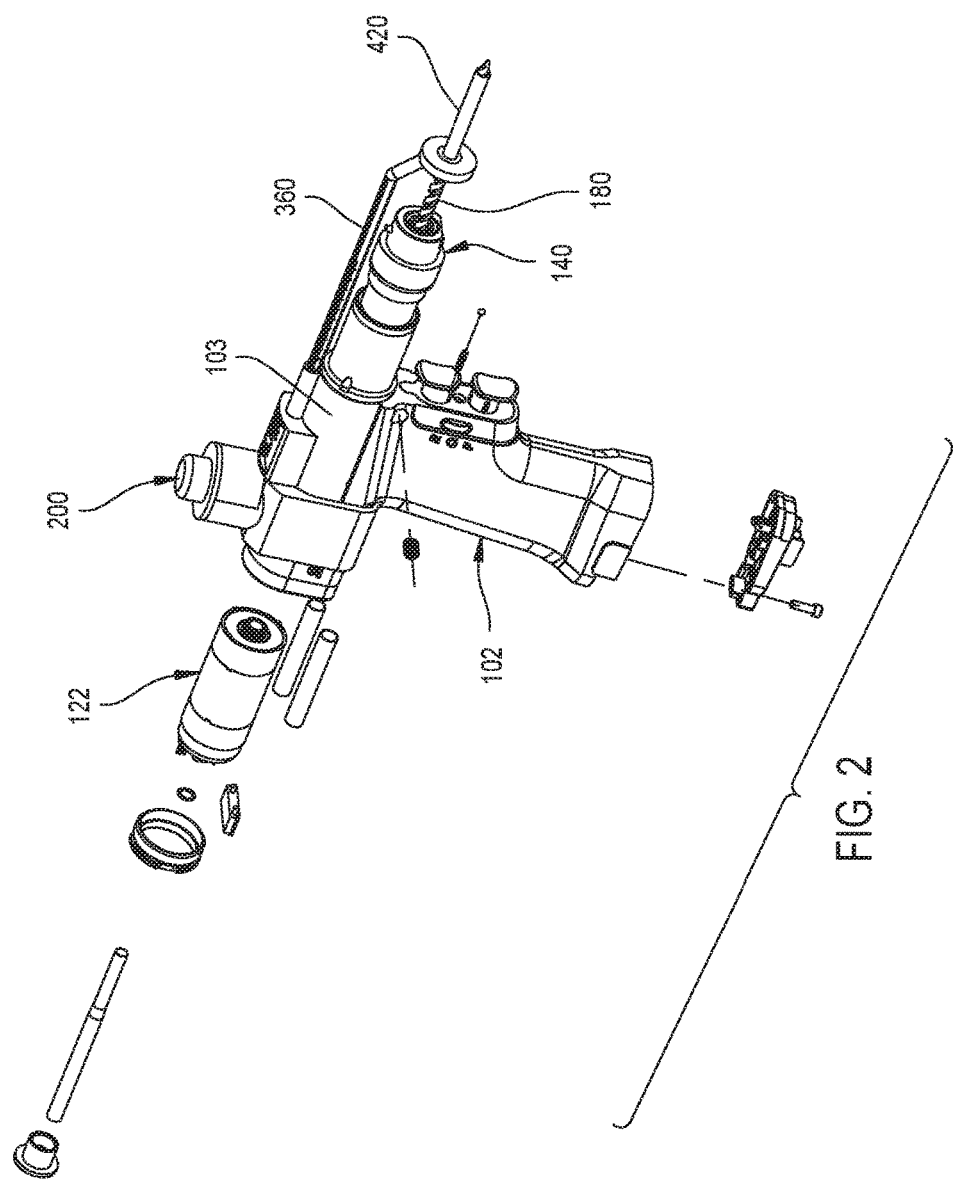
FIG. 2 is a partial exploded view of handpiece components of the rotary surgical drill of FIG. 1.
Figure 3:
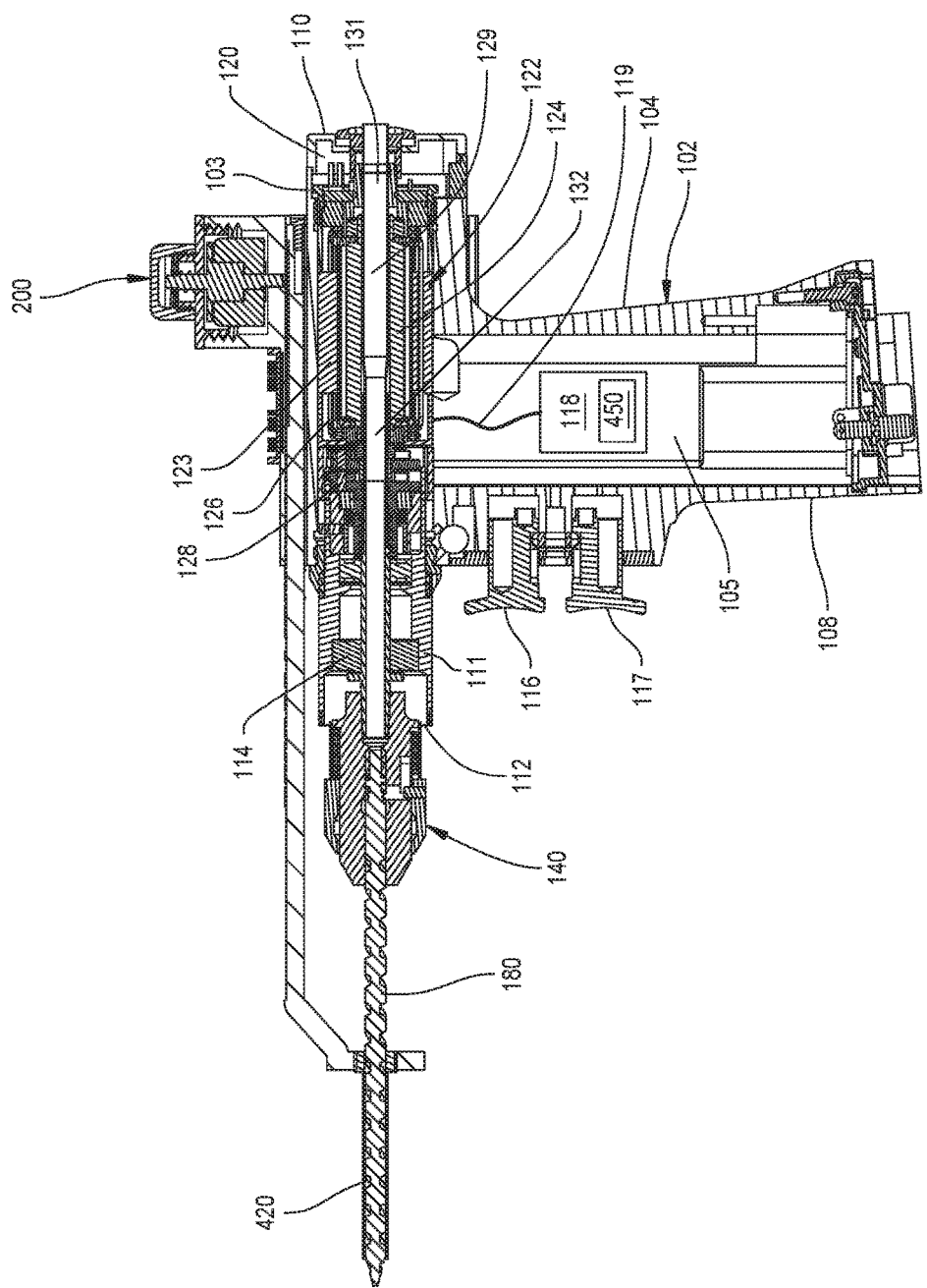
FIG. 3 is a side cross-sectional view of the rotary surgical drill of FIG. 1.

FIGS. 1, 2 and 3 illustrate a rotary surgical drill 100 in accordance with the present invention. Rotary surgical drill 100 comprises handpiece 102, chuck assembly 140, drill bit 180, controller 450 and brake mechanism 200.

Rotary surgical drill 100 includes a handpiece 102. Handpiece 102 has a case or upper housing 103 and a handle 104 that extends downwardly from the case or upper housing 103. Handle 104 is generally in the form of a pistol grip that can be grasped during use by a medical practitioner. Handle 104 has a lower end 108. The case or upper housing 103 is generally cylindrical in shape and has a distal end 106 and a proximal end 107. The case or upper housing 103 has an internal cylindrical shaped cavity 120. The upper housing 103 and handle 104 are formed from suitable materials such as metals.

In the discussion of surgical drill 100, "Distal", it shall be understood means away from the practitioner holding the drill 100; towards the surgical site to which the surgical drill 100 is directed. "Proximal", means towards the practitioner, away from the surgical site.

Figure 3A:
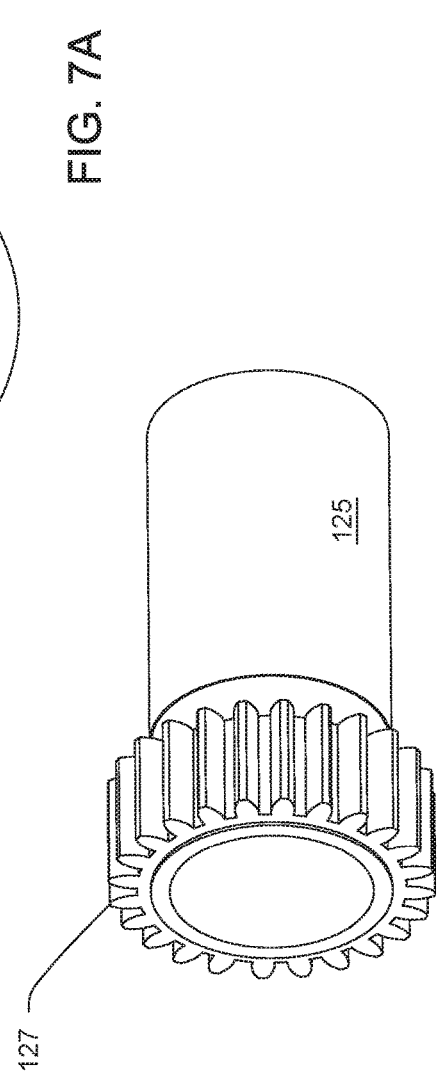
FIG. 3A is a perspective view of the head of the motor rotor depicted in FIG. 3.
Figure 3B:
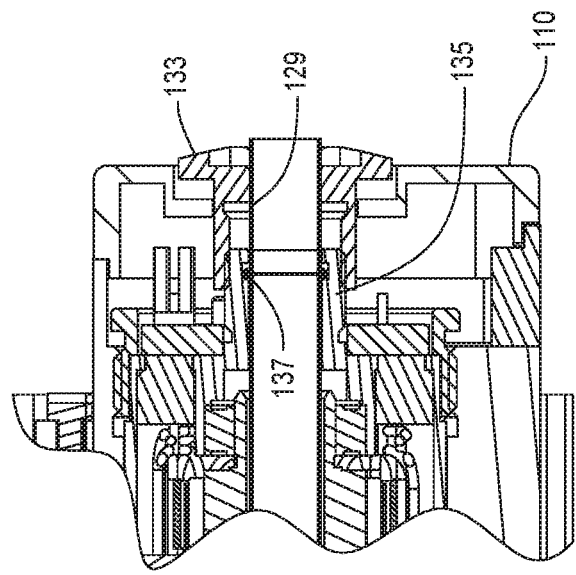
FIGS. 3B and 3C are enlarged portions of the cross sectional view of FIG. 3.

A rotary electric motor 122 is mounted in cavity 120. In one embodiment, the electric motor 122 is a brushless DC motor. In another embodiment the motor can be an AC motor, or a pneumatic or hydraulically driven motor. Electric motor 122 includes a stator 123 Also part of motor 122 are windings 126 that are wound around the stator 123. A rotor 124 is rotatably disposed in stator 123. Rotor 124 is formed so as to have an axially extending through bore, (bore not identified). Rotor 124 has head 127, seen in FIG. 3C, that is the form of a gear. In FIG. 3A a tube like sleeve 125 is shown extending proximally from head 127. When drill 100 is assembled, sleeve 127 is press fit in the open distal end of the motor rotor 124 so that the sleeve and head rotate with the rotor. This is for manufacturing purposes only. In alternative versions of the invention, head 127 may be integrally formed with the motor rotor.

Figure 36:
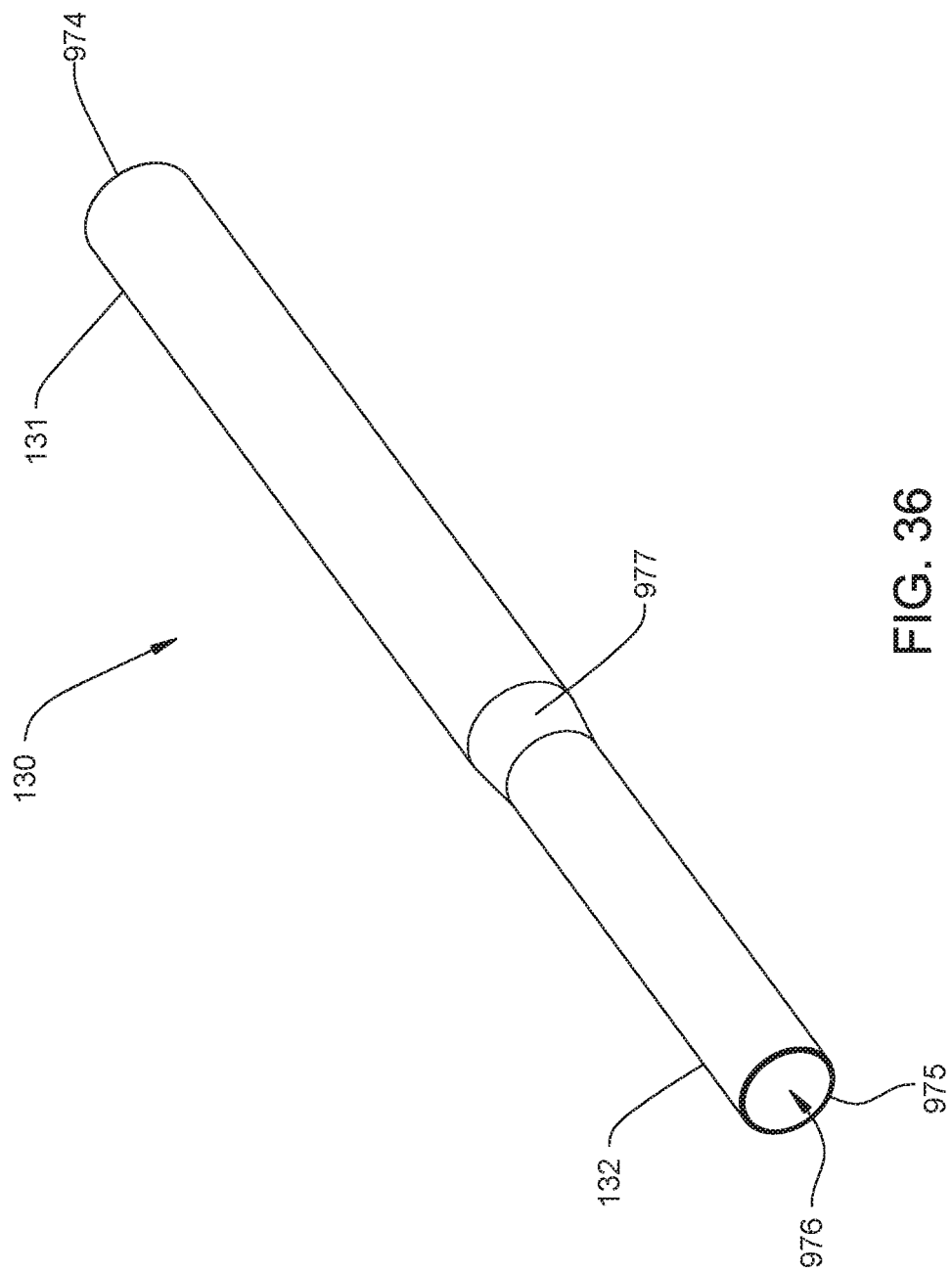
FIG. 36 is a front perspective view of the static tube that extends through the cannulated shaft of the motor.

A tube 129, seen in FIGS. 3 and 36, extends through and is statically mounted in motor rotor 124. Tube 129 has a proximal end 131 that is located proximal to motor rotor 124. The tube has a distal end 132 located distal to the motor rotor 124. In the depicted version of the invention, the distal section of tube 129 that defines the distal end 132 has inner and outer diameters that are less than the corresponding diameters of the proximal end 129. Tube 129 has a lumen 976 with a proximal opening 974 and a distal opening 975. Tube section 977 is the tapered transition section between the large proximal section of the tube and the smaller diameter distal section. When handpiece 102 is assembled sleeve 125 surrounds the distal section of tube 129.

Figure 3C:
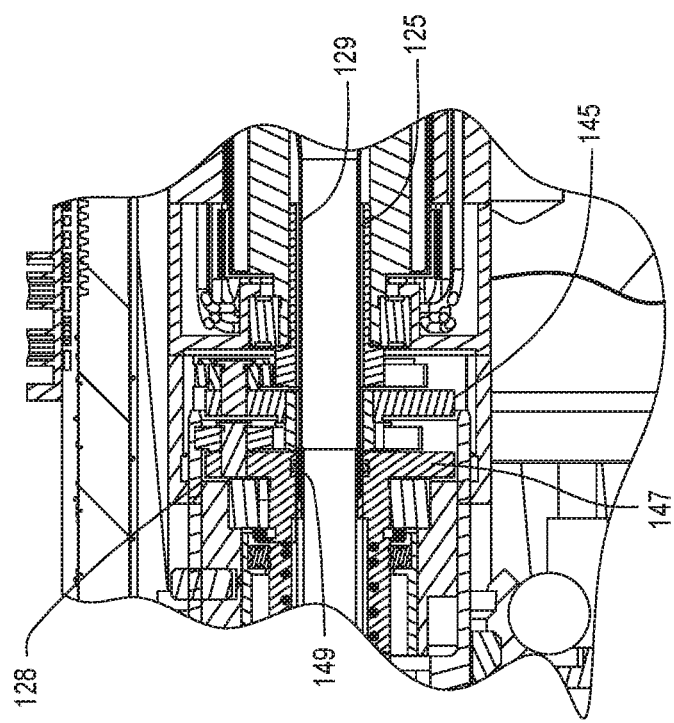

Tube proximal end 131 is disposed in an end cap 133 disposed in the proximal end face of cover 110 as seen in FIG. 3A. Forward of end cap 133, tube extends through a static sleeve 135 internal handpiece 102. An O-ring 137 forms a barrier between the outer surface of tube 129 and sleeve 135. Tube distal end 132 extends through a planetary gear assembly 128 as seen in FIG. 3C. Planetary gear assembly 128 has two carriers 145 and 147. The distal section of tube 129 extends through the proximal carrier, carrier 145 and terminates in the distal carrier, carrier 147. An O-ring 149 provides a seal between the outer surface of tube 129 and the inner surface of distal carrier 147. Tube 129 is held static in handpiece 102 by the compression fitting of the tube in cap 133 and the force exerted by O-ring 137.

Rotor head 127 is the sun gear of planetary gear assembly 128. More particularly rotor head 127 is the sun gear of the planet gears connected to carrier 145. Carrier 145 has a sun gear, (not identified). The sun gear of carrier 145 drives the planet gears attached to carrier 147. Carrier 147 is connected to chuck assembly 140. Planetary gear assembly 128 drives chuck assembly 140 at a slower rotational rate than that of motor 122. A cover 110 is mounted over the proximal end 107 of housing 103 enclosing motor 122 within cavity 120. A shroud 111 is mounted over the distal end 106 of housing 103. Shroud 111 has an opening 112 that receives one end of chuck assembly 140.

Handle 104 allows a user to grasp and manipulate the rotary surgical drill 100. The handle 104 is hollow and has an internal chamber 105. A forward trigger switch 116 and a reverse trigger switch 117 extend distally forward from the front face of handle 104. A printed circuit board (PCB) 118 is mounted in the chamber 105 internal to handle 104. The PCB 118 is electrically connected to the motor 122 and to the trigger switches 116 and 117 by one or more wires 119. PCB 118 contains a controller 450 that monitors the actuation of the trigger switches 116 and 117. Based on the extent to which the trigger switches 116 and 117 are depressed, the controller 450 selectively energizes the motor 122 to cause the motor shaft 130 to rotate at the desired speed. A rechargeable battery 150 is removably attached to the bottom end of handle 104 and is electrically connected to PCB 118 and motor 122. Battery 150 supplies power to rotary surgical drill 100.

Surgical drill 100 further comprises a drill bit 180. A brake mechanism 200, also part of drill 100, limits or stops the forward movement of drill bit 180. The chuck assembly 140 removably retains drill bit 180 for rotary motion at a surgical site. Drill bit 180 can be selectively attached to and detached from the chuck assembly 140 by the medical practitioner. Chuck assembly 140 has a release collar 141. Manual movement of the release collar 141 in a proximal direction causes the chuck assembly to release an inserted drill bit 180. Releasing the release collar 141 causes a coil spring 143 to bias the release collar in a distal direction resulting in the inserted drill bit 180 being locked in chuck assembly 140.

A more detailed understanding one version of how the motor internal to handpiece 102 operates is found in the Applicant's Assignee's U.S. Pat. No. 7,638,958, issued 29 Dec. 2009, the contents of which are explicitly incorporated herein by reference. It should be understood that the exact structure of the portions of the motor that produce the rotational power is not part of this or the other versions of this invention. The structure of the motor in this version and the other versions of the invention is relevant in so far as certain motor components are features of this invention that facilitate the selective stopping of penetration of bone by drill bit 180.

II. Rotary Surgical Drill with Top Mounted Brake Mechanism Having an External Telescoping Rack A. Brake Mechanism With reference to FIG. 4, brake mechanism 200 mounted to the top side of handpiece 102 is shown. The brake mechanism 200 comprises a linear actuator 250 and a telescoping rack, bar or rod 360 that are mounted in an actuator housing 204. Actuator housing 204 is mounted to handpiece 102. Specifically, the actuator housing 204 is mounted to case 103 toward proximal end 107 and rearward of handle 104. The actuator housing 204 extends upwardly above case 103.

Turning to FIGS. 6A-6D, details of the actuator housing 204 are illustrated. The actuator housing 204 has a C-shaped body 206 that is formed with a pair of generally parallel opposed arms 208 that extend away from a central body 206. Body 206 and arms 208 define a passage 209 that extends through housing 204. The bottom side of body 206 has a surface 207 that faces passage 209. The arms 206 terminate in opposed ribs 210 that angle inwardly into passage 209. Apertures 212 are formed in the lower most portion of each arm 208. The apertures 212 are dimensioned to receive screws 214. The screws 214 hold the housing 204 to handpiece 102. A cylindrical shaped boss 216 is attached to body 206 and extends perpendicularly in an upward direction away from body 206. The boss 216 is formed with a bore 218 that is defined by an inner annular surface 220. Internal threads 222 are defined in inner annular surface 220. The actuator housing 204 can be formed from suitable materials such as a metal.

The bore 218 extends downwardly into boss 216 and terminates in a bottom wall 224. A cable slot 225 is defined in bottom wall 224 and extends through the bottom wall 224. Two spaced apart circular holes 226 also extend through bottom wall 224 and are contiguous with passage 209. A D-shaped aperture 228 extends through bottom wall 224 and is contiguous with passage 209. A counter-bore 230 surrounds each of the holes 226 and extends from surface 207 partially into body 206.

An elongated tube 232 has a proximal end 233 that is connected to a distal face of body 206 and a distal terminal end 234. A square shaped lumen 236 extends entirely through tube 232 and also entirely through body 206. The lumen 236 is defined by four orthogonal inner walls 238 that extend along the length of lumen 236. A projection 239 (FIG. 5B) extends upwardly from the bottom wall 238 slightly into lumen 236 towards the proximal end of the housing.

Figure 4:
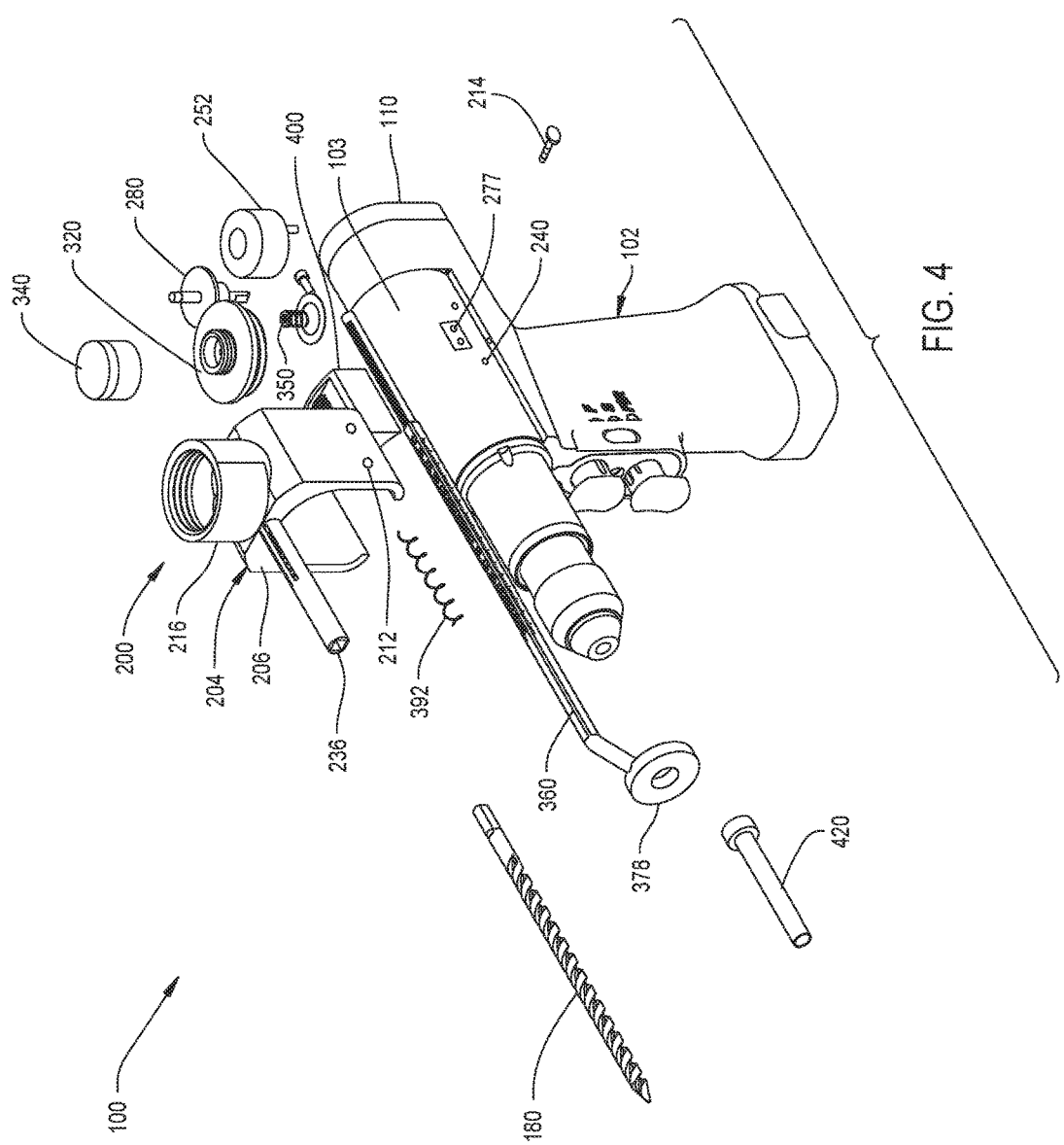
FIG. 4 is an exploded view of the brake mechanism of the rotary surgical drill of FIG. 1.

The actuator housing 204 is mounted to handpiece 102. Housing 204 is placed over upper housing 103 with arms 208 surrounding upper housing 103 and housing inner surface 207 resting against upper housing 103. The upper housing 103 includes threaded holes 240 (FIG. 4). The screws 214 (FIG. 4) extend through housing apertures 212 and are received by threaded holes 240 thereby securing actuator housing 204 to handpiece 102.

Figure 7A:
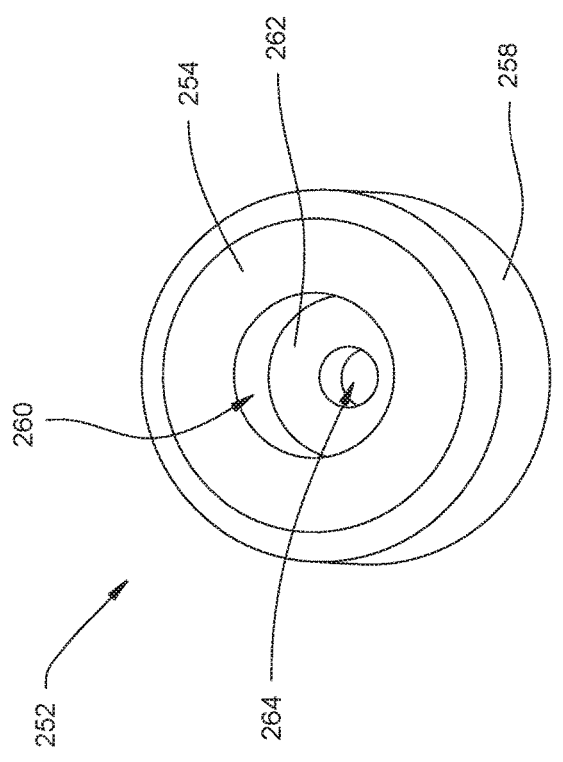
FIG. 7A is a top perspective view of a solenoid.
Figure 7B:
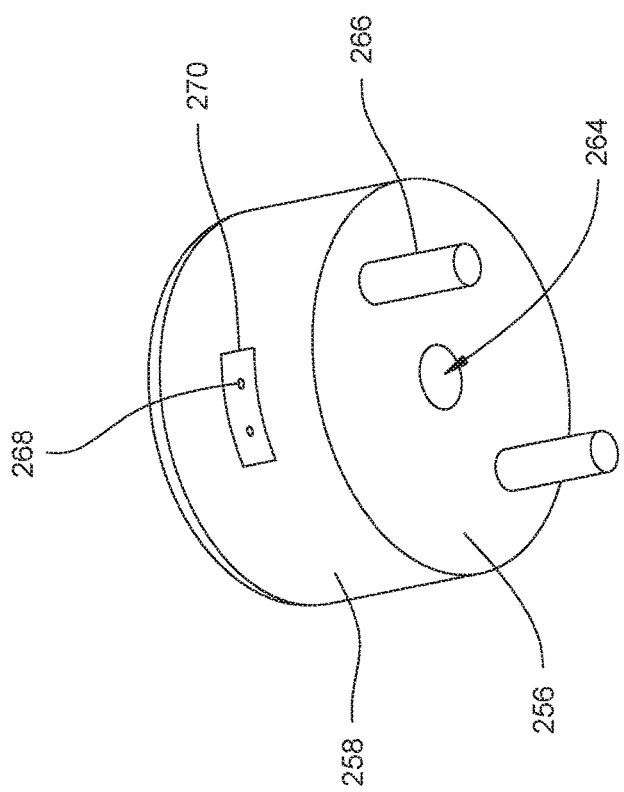
FIG. 7B is a bottom perspective view of the solenoid.

The linear actuator 250 comprises an actuator or solenoid 252 and a piston or plunger 280. Solenoid 252, described with reference to FIGS. 7A and 7B, is generally cylindrical in shape and has a top surface 254, a lower surface 256 and a circumferential outer surface 258. A counter-bore 260 extends downwardly from top surface 254 into solenoid 252 and terminates in a bottom wall 262. A bore 264 is defined through wall 262. Bore 264 extends between bottom wall 262 and lower surface 256. A pair of cylindrical pins 266 extend perpendicularly away from lower surface 256 and are located on opposite sides of bore 264. The solenoid 252 has internal wire windings (not shown) that, when energized by an electrical current, create a magnetic field. The wire windings are connected to terminals 268 that are mounted in a connector 270 on the outer surface 258. The terminals 270 are connected to respective circuit lines at end 275 of a flexible cable 274 (FIG. 5A) using suitable techniques such as soldering.

Figure 5A:
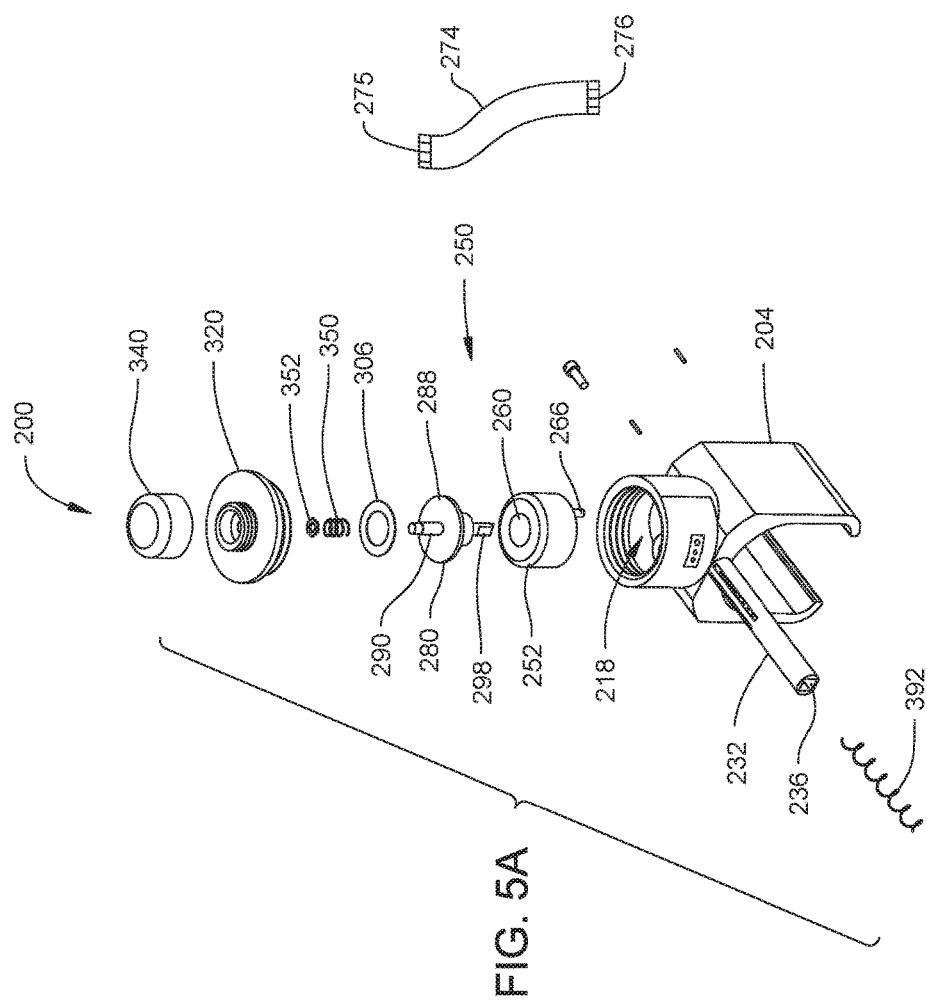
FIG. 5A is an exploded perspective view of the brake mechanism in accordance with the present invention.
Figure 5B:
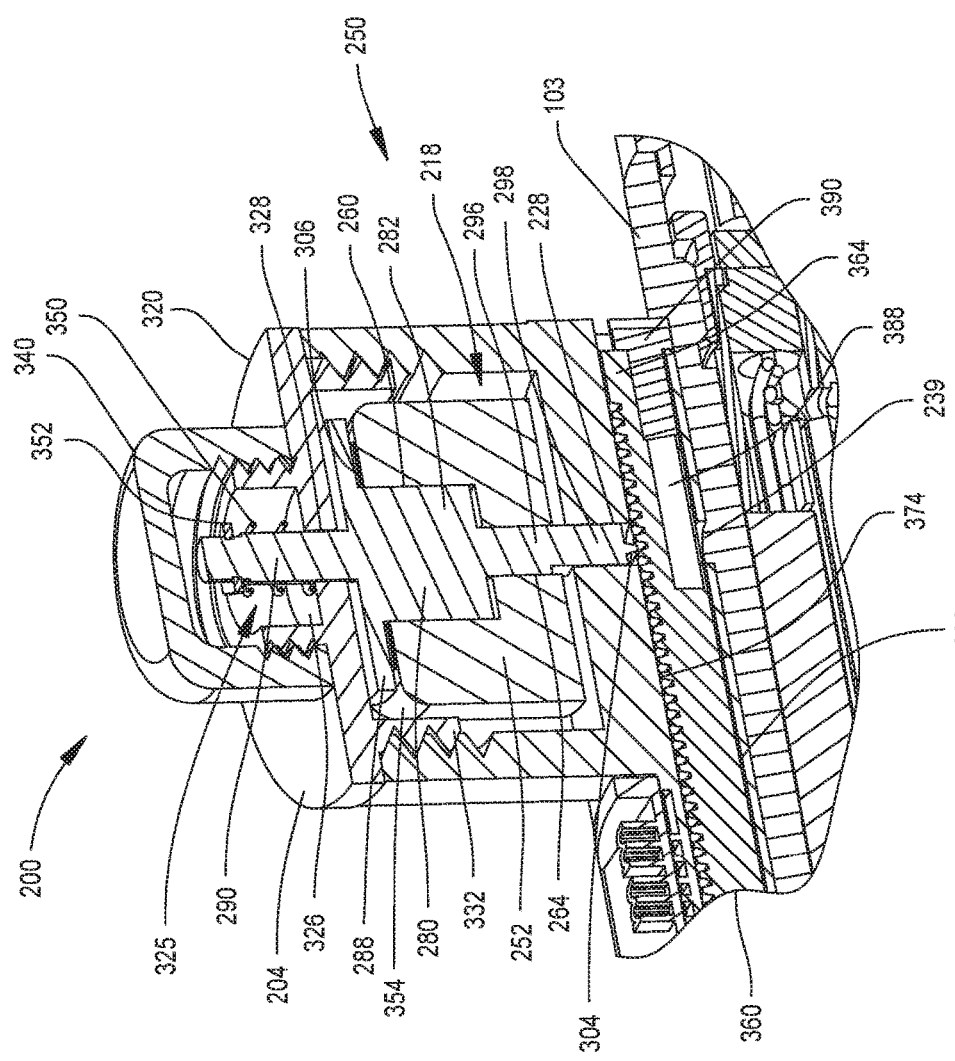
FIG. 5B is an enlarged cross-sectional view of the brake mechanism mounted to the handpiece.
Figure 6D:
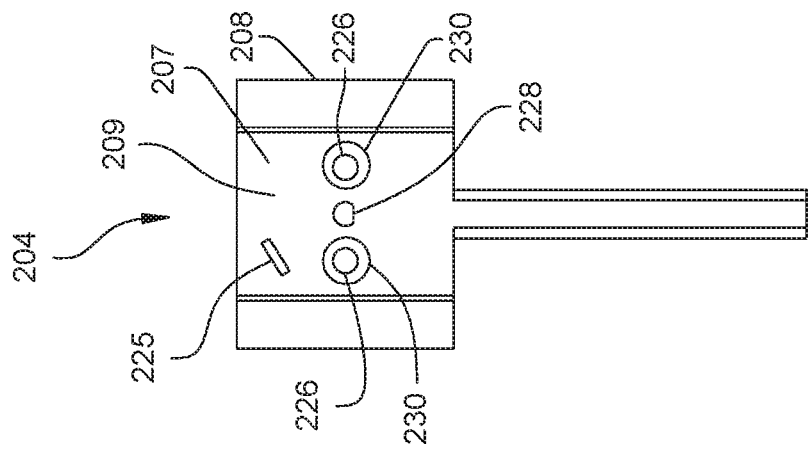
FIG. 6D is a bottom view of the brake mechanism housing.
Figure 6C:
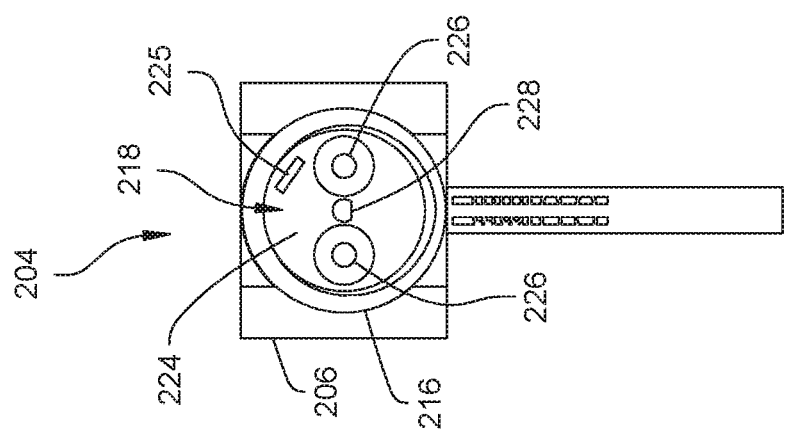
FIG. 6C is a top view of the brake mechanism housing.
Figure 6B:
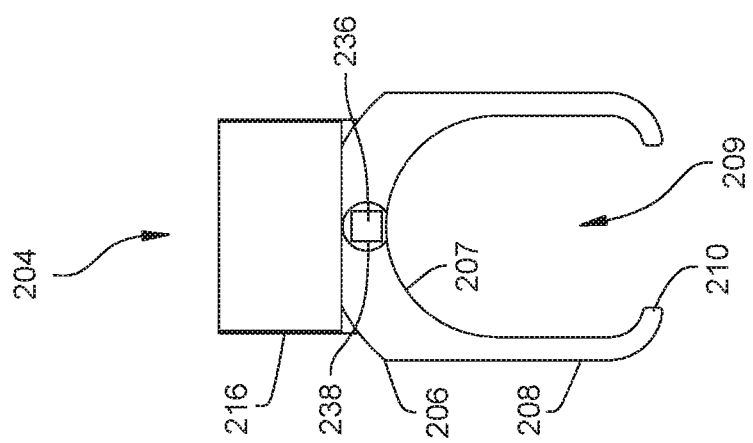
FIG. 6B is a rear view of the brake mechanism housing.

With additional reference to FIGS. 5A and 5B, the solenoid 252 is mounted into the bore 218 of the housing such that the solenoid bottom surface 256 is adjacent to and resting on bottom wall 224 (FIG. 6C) and the pins 266 extend into and are retained in housing holes 226. In one embodiment, holes 226 and pins 266 are dimensioned such that pins 266 are press fit into holes 226. The solenoid circumferential outer surface 258 is surrounded by the housing inner surface 224. The flexible cable 274 extends from solenoid 252 and is routed through cable slot 225 (FIG. 6C) in bottom wall 224. The other end 276 of flexible cable 274 is electrically connected to terminals 277 (FIG. 4) located on handpiece upper housing 103. Terminals 277 are electrically connected to PCB 118 (FIG. 3). Solenoid 252 is therefore electrically connected to PCB 118 via flexible cable 274.

Figure 8B:
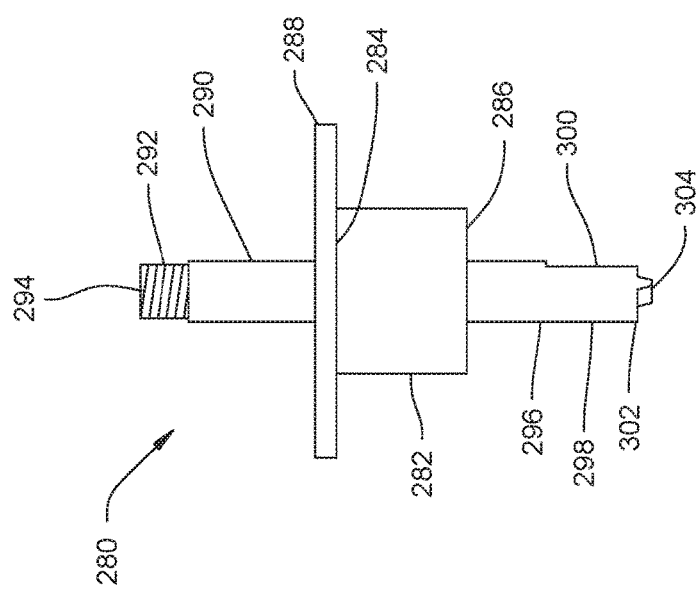
FIG. 8B is a left side view of the brake mechanism plunger.

Referring now to FIGS. 8A and 8B, the plunger 280 includes a central cylindrical shaped hub 282 that has an upper end 284 and a lower end 286. A disc shaped flange 288 extends outwardly from the upper end 284. A cylindrical shaped post 290 extends perpendicularly away from the flange 288. Post 290 has a terminal section 292 that has a diameter that is less than the remainder of post 290. External threads 294 are defined on terminal section 292. A cylindrical shaped shaft 296 extends perpendicularly away from the hub lower end 286. The shaft 296 has a D-shaped terminal section 298 that is partially defined by a flat surface 300. D-shaped terminal section 298 terminates at an end 302. A gear tooth 304 extends outwardly from end 302. Gear tooth 304 is shaped to engage with teeth in telescoping rack 360 as will be described later. In one embodiment, the plunger 280 is formed from a Ferro-magnetic material such as steel that is attracted to a magnetic field.

With additional reference to FIGS. 5A and 5B, plunger 280 is mounted within solenoid 252. The plunger hub 282 is received into the solenoid bore 260 with the cylindrical shaft portion 296 extending through bore 264. The D-shaped section 298 further extends into and is received by the D-shaped aperture 228 of housing 204. A washer 306 is mounted over plunger hub 282 and rests against the bottom face of flange 288. The plunger flange 288 extends over the top surface 254 of solenoid 252 and is slightly spaced from top surface 254.

Turning to FIGS. 9A and 9B, features of cover 320 are illustrated. Cover 320 is cylindrical in shape and has a top side 321 and a bottom side 322. A circular collar 324 extends perpendicularly away from top side 321. A bore 325 is defined in collar 324. Bore 325 terminates in a wall 326. External threads 327 are defined on the outer surface of collar 324. An aperture 328 is defined through the center of wall 326 and is contiguous with bore 325. Another circular collar 330 extends perpendicularly away from the bottom side 322. Collar 330 has a larger diameter than collar 324. A bore 331 is defined in collar 330. The bore 331 terminates at bottom side 322. External threads 332 are defined on the outer surface of collar 330. Cover 320 can be formed from injection molded plastic or metal.

Referring to FIGS. 10A and 10B, features of cap 340 will now be described. The cap 340 is cylindrical in shape and has a top side 342 and a lower side 344. A bore 346 extends from lower side 344 partially into cap 340. Internal threads 348 are defined on the inner surface of bore 346.

With additional reference to FIGS. 5A and 5B, cover 320 is attached to actuator housing 204. Cover 320 encloses the linear actuator 250 of solenoid 252 and plunger 280. The cover 320 is screwed into housing 204 such that the cover external threads 332 are mated with the housing internal threads 222. The cover 320 extends over the top side of flange 288 such that flange 288 is juxtaposed to the bottom side 322 of cover 320. The cylindrical post 290 of plunger 280 extends upwardly through the cover aperture 328.

A coil spring 350 is located in cover bore 325 and surrounds the plunger post 290. A nut 352 is threaded onto the threads 294 (FIG. 8B) of post 290 in order to retain coil spring 350 to post 290. The coil spring 350 is compressed between nut 352 and wall 326 of cover 320. The coil spring 350 biases the plunger 280 in an upward direction away from solenoid 252. The cap 340 is screwed onto cover 320 such that the cover external threads 327 are mated with the cap internal threads 348. The cap 340 completes a sealed enclosure for linear actuator 250.

A space or gap 354 (FIG. 5B) is defined between the bottom side 322 of cover 320 and the top surface 254 of solenoid 252. The flange 288 of plunger 280 can move in gap 354 between a first position when solenoid 252 is de-energized or turned off and coil spring 350 biases the flange 288 into contact with the bottom side 322 of cover 320. When solenoid 252 is energized or turned on, the magnetic field generated by solenoid 252 attracts the steel flange 288 and overcomes the spring force of coil spring 350, thereby moving flange 288 into contact with the top surface 254 of solenoid 252.

Figure 11:
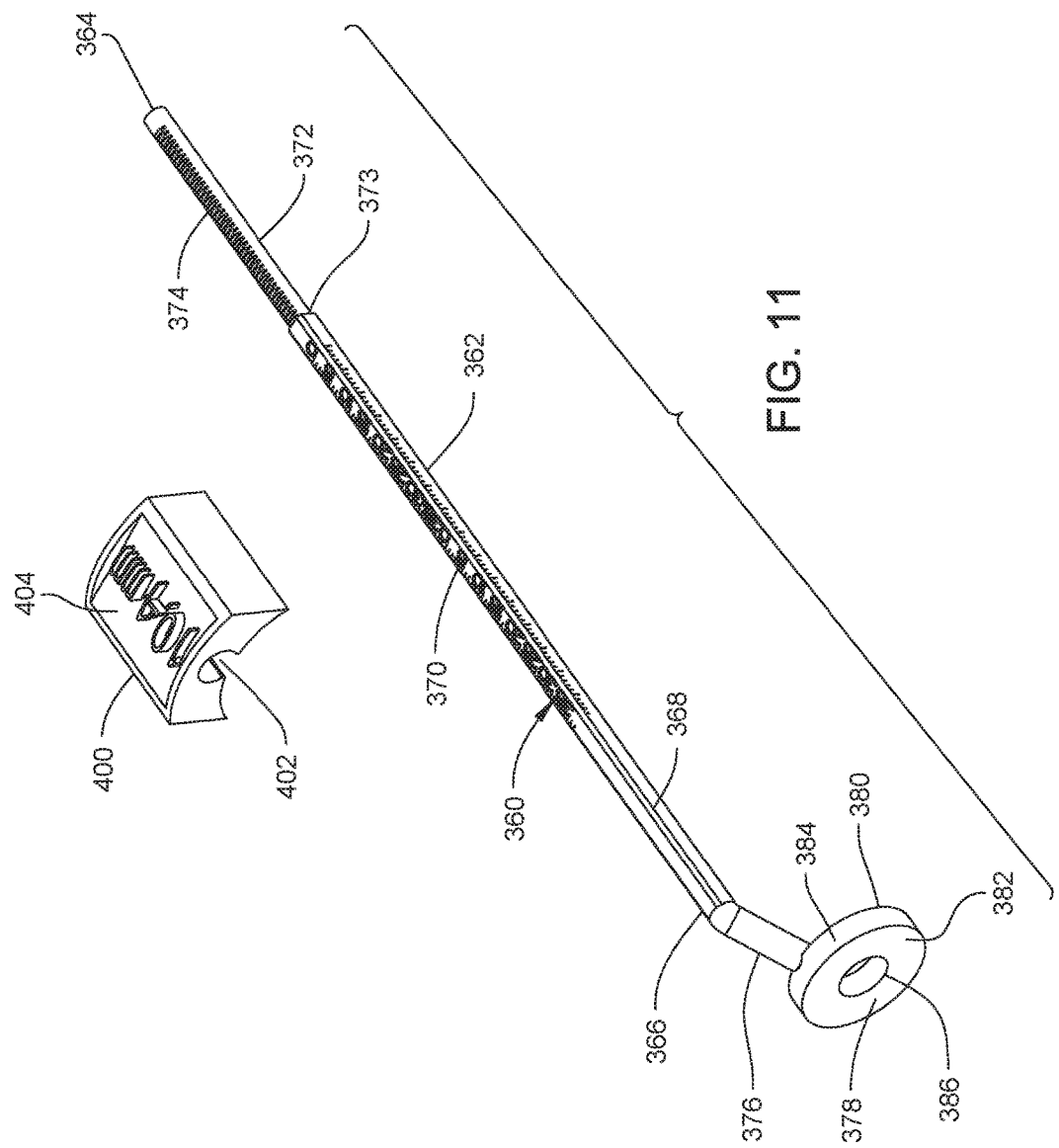
FIG. 11 is a top perspective view of a rack and digital caliper.

FIG. 11 illustrates features of telescoping rod or rack 360. Telescoping rack 360 can be formed from suitable materials such as metal. Rack 360 is generally elongated in length and has a center section 362, a proximal end 364 and a distal end 366. Rack 360 has a square cross-sectional profile that is defined by four orthogonal sides 368. A linear measurement scale or depth gauge 370 is affixed to one or more sides 368 of rack 360 within center section 362. The linear measurement scale 370 can include graduated marks and indicia such as numbers. Marks on the linear measurement scale correspond to the length of the drill bit that extends beyond the end of the tissue protector. The depth gauge 370 is used to measure the length of drill bit 180 that is inserted into a bore. In one embodiment, measurement scale 370 can be graduated in millimeters. Depth gauge 370 is read where rack 360 enters tube 232 at the intersection of depth gauge 370 and the tube distal end 234.

The rack 360 further has a proximal section 372 with a round cross-sectional shape that is located toward the proximal end 364. A step 373 is defined where center section 362 and proximal section 372 intersect.

A set of gear teeth 374 are formed in the upper side of the proximal section 372 and extend along the length of proximal section 372 between center section 362 and proximal end 364. The teeth 374 are dimensioned such that tooth 304 (FIG. 8B) can mate with and be engaged with teeth 374. An arm 376 is attached to the distal end 366 of rack 360. The arm 376 angles downwardly and away in a distal direction from distal end 366. An annular ring 378 is attached to arm 376. The ring 378 has a proximal face 380, a distal face 382 and a circumferential outer side surface 384. The arm 360 is attached to proximal face 380. A circular opening 386 extends through ring 378.

Turning to FIG. 5B, the rack 360 is further formed with a threaded bore 388 that extends from proximal end 364 partially into proximal section 372. The bore 388 receives a screw 390. The head of screw 390 abuts the proximal face of housing 204. Screw 390 prevents the removal of rack 360 from housing 204 after the rack is inserted into lumen 236.

Referring additionally to FIGS. 4, 5A, 5B and 6A, rack 360 is mounted in lumen 236 for telescoping or sliding movement. Rack 360 can slide or telescope in a linear manner in proximal and distal directions relative to actuator housing 204. A coil spring 392 is located in lumen 236 partially surrounding the center section 362 of rack 360. The distal end of the coil spring 392 rests against step 373 and the proximal end of coil spring 392 rests against a projection 239 (FIG. 5B) that extends into lumen 236. The coil spring 392 biases rack 360 in a distal direction away from handpiece 102.

Returning to FIG. 11, a digital caliper or second depth gauge 400 is mounted to upper housing 103. Digital caliper 400 can be attached to upper housing 103 using fasteners (not shown). Digital caliper 400 is commercially available. Digital caliper 400 has U-shaped groove that receives and is mounted over a portion of tube 232. Digital caliper 400 has a digital display 404 that is calibrated to the position of rack 400 relative to handpiece 102. Digital caliper 400 can sense the position of rack 360 and provide a numerical readout of a distance that rack 360 is extended from or inserted into digital caliper 400 which corresponds to a measure of the length of drill bit 180 that is inserted into a bone bore.

Figure 12A:
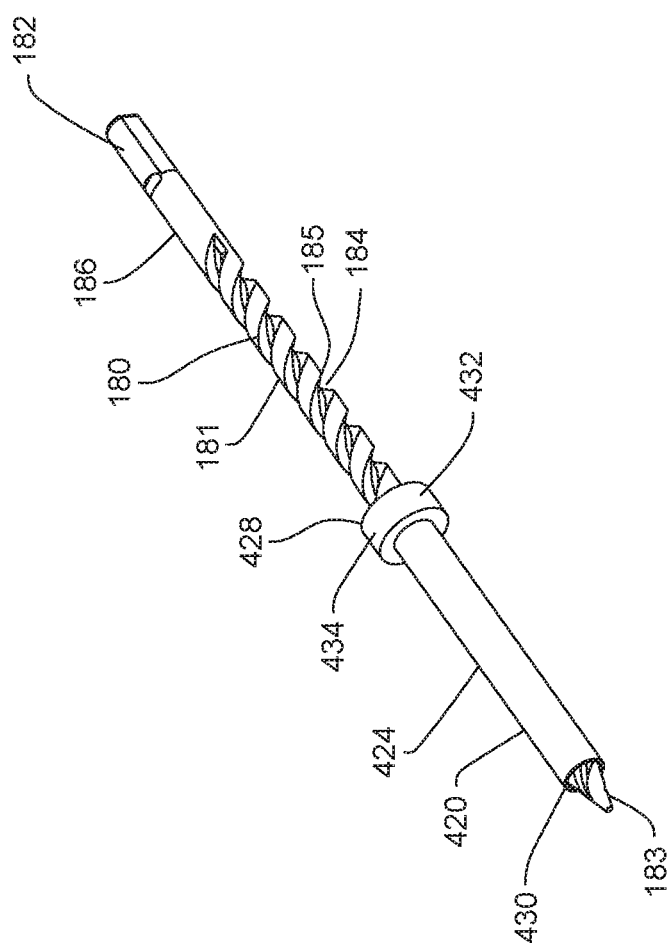
FIG. 12A is a top perspective view of a drill bit mounted in the tissue protector in accordance with the present invention.

With reference to FIGS. 12A and 12B, a tissue protector 420 positioned around drill bit 180 is shown. Drill bit 180 has a center section 181, a square shaped proximal drive head 182, and a distal pointed cutting tip 183. The square shaped proximal drive head 182 is clamped within chuck assembly 140 holding drill bit 180 to chuck assembly 140. Drive head 182 receives rotary torque from chuck assembly 140 in order to rotate drill bit 180. Grooves 184 are defined in the center section 181 of drill bit 180 by edges 185. The drill bit 180 has an outer circumferential surface 186.

The tissue protector 420 is generally cylindrical in shape. Tissue protector 420 is formed with a hollow sleeve 424 that defines an interior passage 426. The sleeve 424 has an outer surface 425. The passage 426 extends through the entire length of tissue protector 422. The tissue protector 420 has a proximal end 428 and a distal end 430. A flange 432 extends outwardly and surrounds the proximal end 428 of tissue protector 420. Flange 432 has an outer annular surface 434.

The tissue protector 420 is attached into the opening 386 (FIG. 11) of ring 378 (FIG. 11). Specifically, flange 432 has external threads (not shown) on the outer annular surface 434 that mate with internal threads (not shown) that face into ring opening 386. The tissue protector 420 is coupled to rack 360 via ring 378. The tissue protector 420 is slid over the outer circumference of drill bit 180. The interior diameter of passage 426 is larger than the diameter of drill bit 180 such that tissue protector 420 can slide relative to drill bit 180 along the length of dill bit 180. Sleeve 424 is dimensioned to have an interference fit to the outer circumference surface 186 of drill bit 180. Drill bit 180 can slide along the inner circumference of sleeve 424 in a distal direction as a bore is formed by drill bit 180.

During the operation of rotary surgical drill 100, as the drill bit 180 moves in a distal direction relative to the static tissue protector 420 during drilling, the length of the drill bit exposed or extending beyond distal tip 430 increases. During formation of a bore by drill bit 180, the distal end 430 of the tissue protector 420 is in contact with a proximal surface of the tissue (bone) adjacent the bore being formed and remains static. When the tissue protector 420 is moved in a distal direction relative to drill bit 180, the length of the drill bit exposed or extending beyond the distal end 430 of the tissue protector decreases.

B. Controller

Figure 13:
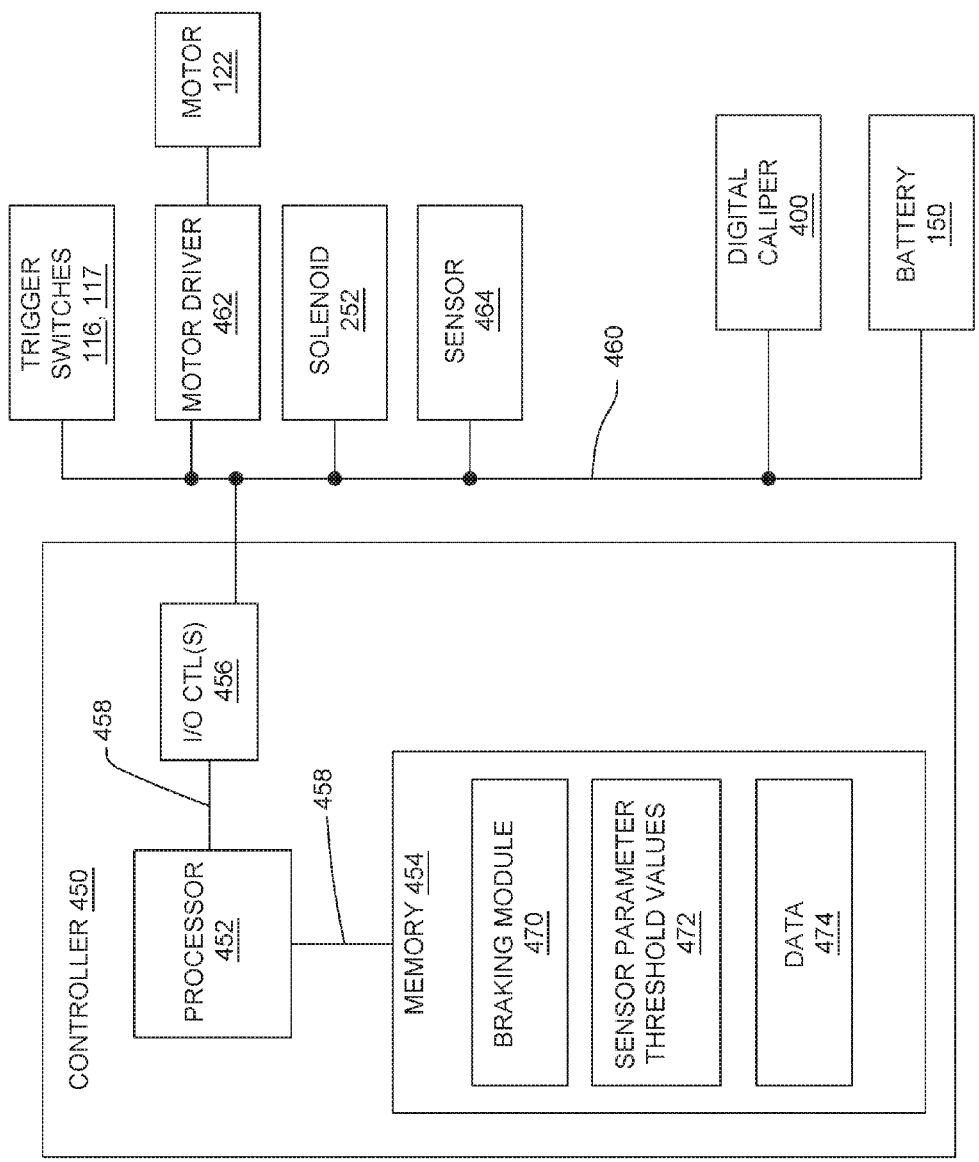
FIG. 13 is a electrical schematic diagram view of the controller and associated components of the rotary surgical drill of FIG. 1 in accordance with the present invention.

FIG. 13 illustrates a schematic diagram of the electrical components within surgical drill 100 that are connected to controller 450. Controller 450 controls the operation of rotary surgical drill 100. Controller 450 also controls the operation of braking mechanism 200. The controller 450 comprises a processor 452, memory 454 and input/output (I/O) interface or controller 456. Processor 452 is in communication with memory 454 and input/output interface 456 via one or more communication buses 458. Controller 450 is mounted to PCB 118 (FIG. 3) within handpiece 102.

Processor 452 is a suitable microprocessor, field programmable gate array or an application specific integrated circuit. One or more sets of instructions or software are stored on a machine-readable medium or memory 454 that embodies any one or more of the methods or functions described herein. Memory 454 is a random access memory (RAM) or a nonvolatile random access memory such as NAND flash memory or any other suitable memory. Processor 452 can also contain memory that least partially stores programs within processor 452 during execution thereof. Memory 454 stores firmware/software/programs that at least partially control the operation of rotary surgical drill 100. In one embodiment, the controller 450 is a single integrated circuit.

The term "memory or machine-readable medium" shall also be taken to include any medium that is capable of storing, encoding or carrying out a set of instructions for execution by the processor and that cause the processor to perform any one or more of the methodologies shown in the various embodiments of the present invention. Machine-readable medium or memory shall accordingly be taken to include, but not be limited to, solid-state memories, optical and magnetic media, and carrier wave signals.

The I/O interface or controller 456 provides the required timing, signal levels and protocols to allow processor 452 to communicate with components external to controller 450. I/O interface 456 is in communication with external components through several electrical cables or wires 460. I/O interface 456 is in communication with trigger switches 116, 117 and a motor driver 462. The motor driver 462 is a circuit that provides the proper current and voltage levels to power electric rotary motor 122. The electric rotary motor 122 is a variable speed electric motor that rotates chuck assembly 140 and drill bit 180.

A sensor 464 is in communication with I/O interface 456. Sensor 464 can be one of a variety of sensors that sense operating conditions and parameters of rotary surgical drill 100. In one embodiment, sensor 464 is a Watt and current sensor that senses the Watts consumed and current drawn by motor 122 and provides an electrical signal that corresponds to the voltage and current drawn by motor 122. In another embodiment, sensor 464 is a rotation sensor that senses the number or revolutions per minute (RPM) that motor 122 turns. The rotation sensor can be a Hall effect sensor that counts the number of revolutions of rotor 124. The rotation sensor provides an electrical signal that corresponds to the RPM of motor 122. In one more embodiment, sensor 464 is a torque or force sensor that senses torque on one or one or more components of rotary surgical drill 100 and provides an electrical signal that corresponds to the torque reading. For example, sensor 464 can be a strain gauge that is mounted to motor shaft 130 and is in electrical communication with I/O interface 456.

I/O interface 456 is also in communication with solenoid 252. Processor 452 can cause solenoid 252 to turn on (energized) or turn off (de-energized). Processor 450 is further in communication with digital caliper 400 and with a power supply or battery 150 through I/O interface 456. Digital caliper 400 can transmit a digital signal to processor 452 that indicates the depth of the drill bit in a bone bore. Battery 150 provides the electrical power necessary to power controller 450 and motor 122. In one embodiment, controller 450 is mounted to PCB 118 (FIG. 3) within chamber 105 (FIG. 3) of handle 104 (FIG. 3).

The memory 454 can store a variety of data, sets of instructions, software, firmware, modules, programs or utilities for execution by processor 452 and that cause processor 452 to perform any one or more of the functions and methods herein described. Memory 454 comprises a braking module 470, sensor parameter threshold values 472 and data 474. Braking module 470 is a program that determines when to stop the forward travel of drill bit 180 via the actuation of solenoid 252 based on input from sensor 464. Braking module 470 controls the operation of braking mechanism 200. The sensor parameter threshold values 472 are predetermined values of sensor parameters that processor 452 uses to determine when to turn solenoid 252 on and off. In one embodiment, threshold values 472 can be when the motor current drops below a pre-determined level within a pre-determined time period. For example, if the motor current drops below 20 milli-amps within a 15 milli-second period, processor 452 can turn on solenoid 252 causing the engagement of braking mechanism 200. Data 474 can store various operating parameters and conditions of rotary surgical drill 100 such as the number of RPMs and the total usage time of the drill. Data 474 can also keep a log of sensor values over time as detected by sensor 464.

FIG. 13 and the accompanying discussion are intended to provide a general description of an exemplary controller or processor adapted to implement the described embodiments. While embodiments will be described in the general context of instructions residing on memory stored within a controller, those skilled in the art will recognize that embodiments may be implemented in a combination of program modules running in an operating system. Generally, program modules include routines, programs, components, and data structures, which perform particular tasks or implement particular abstract data types.

C. Operation

The rotary surgical drill 100 is used at a surgical site by a medical practitioner. The medical practitioner grasps handle 104 and directs the drill bit tip 183 to the surgical site. Drill bit 180 is used to drill one or more bores into a bone. In one embodiment, a screw can be inserted into the bore.

With reference to FIGS. 1 and 5B, initially, solenoid 252 is turned off by controller 450 such that spring 350 biases plunger 280 to an upper most position where tooth 304 is disengaged from the teeth 374 of rack 360. In this position, rack 360 is free to telescope or slide within lumen 236. Because rack 360 is coupled to tissue protector 420, displacement of tissue protector 420 relative to drill bit 180 causes a like displacement of rack 360. Initially, the tissue protector 420 is manually positioned by a medical practitioner so the distal end 430 of the tissue protector is slightly drawn back from the drill bit distal tip 183. Only the bit distal tip 183 is exposed as seen in FIG. 1. The medical practitioner slides tissue protector 420 relative to drill bit 180 by overcoming the interference fit between tissue protector sleeve 424 and drill bit 180. Also initially, the drill bit 180 is not subjected to any axial loading. Axial loading is defined as a force acting along the same axis as the longitudinal axis of drill bit 180.

In the following discussion of FIGS. 14A-14C, reference is also made to components shown in FIGS. 1, 11, 12A, 12B and 13. Turning to FIG. 14A, surgical drill 100 is used at a surgical site 488 to form a bore in a bone. The drill bit 180 is positioned against the proximal side 492 of the bone 490 where the bone bore 498 is to be formed. The drill bit 180 is forced downwardly by the medical practitioner in an axial direction. After the drill bit 180 is so positioned, the rotary surgical drill 100 is actuated in a forward or clockwise rotation (as viewed from behind the handpiece) by the depression of trigger switch 116. Trigger switch 116 causes controller 450 to rotate motor 122 within handpiece 102 and to rotate the chuck assembly 140 and drill bit 180. The combination of the rotating drill bit and the axial load placed on the drill bit results in the cutting edges of the drill bit tip 183 cutting the bone 490 so as to form a bore 498. During formation of the bone bore, the motor 122 will draw a relatively high level of current in order to keep a desired number of revolutions per minute (RPM) of the drill bit 180. The motor 122 uses the relatively high level of current in order to overcome the frictional force created by the drill bit 180 rubbing against the bone 490. The current and voltage levels drawn by motor 122 is measured by sensor 464 and transmitted as an electrical signal to controller 450.

Referring to FIG. 14B, as the drill bit tip 183 enters the bone, the distal end 430 of tissue protector 420 abuts the proximal side 492 of bone 490 limiting the forward movement of tissue protector 420. As the drill bit 180 continues to rotate, the combination of the rotating drill bit and the axial load placed on the drill bit by the medical practitioner overcomes the interference fit between tissue protector 420 and the outer circumference 186 of the drill bit resulting in the tissue protector 420 remaining static against the bone 490 while the drill bit slides through the interior passage 426 of sleeve 424. As the bone bore 498 is formed, the length of the drill bit 180 exposed or extending beyond the distal end 430 of tissue protector 430 increases. Stated another way, as the drill bit and by extension the handpiece 102 advance, the distance between the distal end of the tissue protection 420 and the handpiece decrease. Continued rotation of the drill bit and axial loading causes the drill bit tip 183 to penetrate through the bone and bone marrow 496 and to approach the distal side 494 of bone 490.

With reference to FIG. 14C, eventually, the drill bit tip 183 bores through the distal side 494 of bone 490 in which the bone bore 498 is being formed. When the drill bit bores through the distal side 494 of bone 490, the frictional force created by the drill bit 180 rubbing against the bone 490 suddenly decreases. The current drawn by motor 122 also rapidly decreases and the RPM of the drill bit 180 rapidly increases. The sudden drop in the current drawn by the motor over a time period is measured or sensed by sensor 464 and the current information is transmitted as an electrical signal to controller 450. In one embodiment, the change in current or current drop over a time period can have units of milliamps per second. Processor 452, which is executing braking module software 470, compares the received change in current data from sensor 464 to a pre-determined threshold change in current or current drop level that is stored in sensor parameter threshold values 472.

In response to the received change in current from sensor 464 being greater than the stored threshold change in current level, processor 452 triggers the engagement of braking mechanism 200 by turning on solenoid 252. When solenoid 252 is turned on, the magnetic field generated by solenoid 252 attracts the steel flange 288 and overcomes the spring force of coil spring 350, thereby moving flange 288 and the attached plunger 280 downwardly until flange 288 contacts with the top surface 254 of solenoid 252. At the same time, the downward movement of plunger 280 forces gear tooth 304 into engagement with gear teeth 374 of rack 360, thereby locking rack 360 to handpiece 102. When gear tooth 304 is engaged with gear teeth 374, handpiece 102 is no longer able to advance towards tissue protector 420. By extension this prevents further advancement of the drill bit 180 beyond the distal side 494 of the bone 490. Any additional rotation of drill bit 180 or application of axial force does not result in further advancement of drill bit 180 due to the abutment of tissue protector 420 against the proximal side 492 of the bone. Drill bit 180 is thus prevented from further advancement beyond distal side 494 thereby avoiding the cutting any tissue 497 adjacent to the distal side 494 of the bone 496.

The length of the drill bit inserted into the bone bore 498 is equal to the distance between the distal end 430 of tissue protector 420 and the distal tip 183 of drill bit 180. This length is the approximate length that is required for a bone screw that is to be inserted into the bone bore by the medical practitioner. The linear measurement scale or depth gauge 370 that is affixed to one or more sides 368 of rack 360 is calibrated to correspond to the length of the drill bit 180 that extends beyond the distal end 430 of tissue protector 420. The length of the drill bit in the bone bore can be read by the medical practitioner where rack 360 enters tube 232 at the intersection of depth gauge 370 and tube distal end 234.

The length of the drill in the bone bore 398 can also be read from digital caliper 400. Digital caliper 400 is calibrated to correspond to the length of the drill bit 180 that extends beyond the distal end 430 of tissue protector 420. The length of the inserted drill bit can be read by a medical practitioner on digital display 404 of digital caliper 400. Therefore, the length of a bone screw required for insertion into bone bore 498 can be read from either depth gauge 370 or from digital caliper 400. Depth gauge 370 and digital caliper 400 allow for the correct length of bone screw to be selected by the medical practitioner to match the depth of the bone bore. Depth gauge 370 and digital caliper 400 can assist in preventing bone screws that are too long or too short from being selected for use.

The medical practitioner may elect to pull the drill bit 180 out from the bone bore before reading depth gauge 370 or digital caliper 400. However, if the bone bore is deep, the fit between the drill bit and the bone bore can be a particularly tight fit. The medical practitioner can rotate drill bit 180 in a reverse (counterclockwise) direction using reverse trigger switch 117 in order to disengage drill bit 180 from the bone bore. Alternatively, with the drill bit 180 removed from the bone bore, the medical practitioner can place bone screws adjacent the drill bit portion that extends beyond the tissue protector 420. The practitioner then visually selects the bone screw that matches the depth of the bone bore.

Before the medical practitioner uses rotary surgical drill 100 to form another bore, braking mechanism 200 is disengaged. In one embodiment, processor 452 turns off solenoid 252 after sensing the depression of reverse trigger switch 117. In another embodiment, processor 452 turns off solenoid 252 after detecting a certain sequence of depression of the trigger switches 116, 117. For example, processor 452 can turn off solenoid 252 after detecting the simultaneous depression of both trigger switches 116 and 117. In an additional embodiment, a separate switch (not shown) can be provided to turn off solenoid 252. After solenoid 252 is turned off, spring 350 biases plunger 280 to move in an upward direction causing disengagement of gear tooth 304 from teeth 374. The rack 360 is now free to slide relative to handpiece 102 and drill bit 180.

The braking mechanism 200 of the present invention using solenoid 252, plunger 280, rack 360 and tissue protector 420 allows a drill bit 180 forming a bone bore to stop further penetration beyond the bone after the initial penetration through the bone, thereby preventing damage to any tissue adjacent the distal side of the bone.

The depth gauge 370 and digital caliper 400 allow for the correct length of bone screw to be selected by the medical practitioner to match the length of the bone bore.

Figure 15:
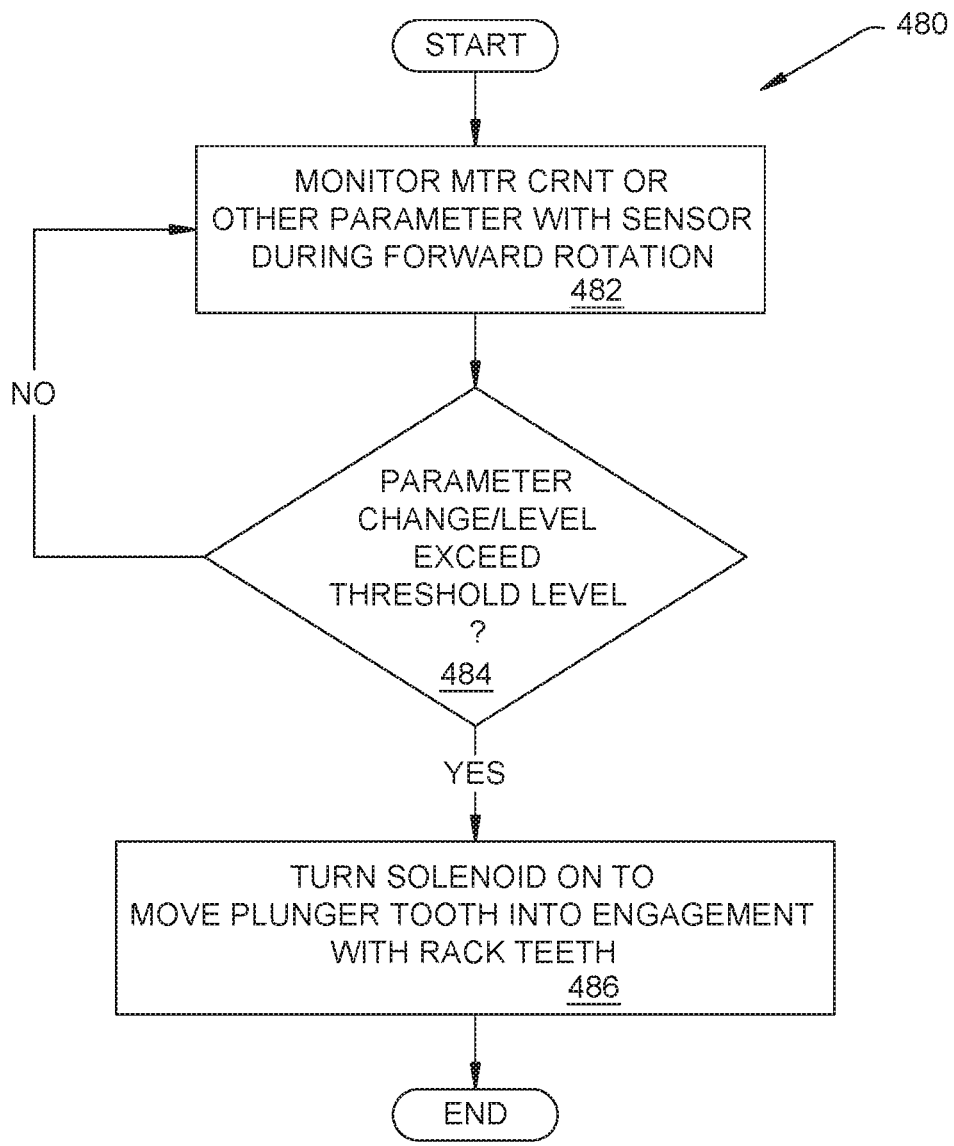
FIG. 15 is a flow chart of a method of operating the rotary surgical drill of FIG. 1 in accordance with the present invention.

Referring to FIG. 15, a flowchart of a method 480 of operating rotary surgical drill 100 (FIG. 1) is shown. Method 480 illustrates an exemplary method by which the rotary surgical drill 100 presented within the preceding figures performs different aspects of the processes that enable one or more embodiments of the disclosure. Method 480 is described specifically as being performed using rotary surgical drill 100 and controller 450. The description of method 480 is provided with general reference to the specific components illustrated within the preceding figures.

Method 480 begins at block 482 where processor 452 executing braking module 470 monitors in real time the voltage and current drawn by rotary electric motor 122 during forward rotation of motor 122. As the drill bit 180 is being rotated by motor 122, the current drawn by motor 122 will vary depending upon the load on motor 122. Processor 452 monitors the voltage and current drawn over time via an electrical signal transmitted from one or more sensors 464.

At decision step 484, processor 452 compares the change in the present current value for a period of time from sensor 464 to a pre-determined threshold value stored in sensor parameter threshold values 472 and determines if the change in current for a period of time is greater than the stored threshold value 472. A sudden drop or change in the current drawn by the motor 122 during a time period indicates that the drill bit has completed cutting through the bone.

In response to the change in current for a period of time not being greater than the stored threshold value 472, method 480 returns to block 482 where processor 452 continues to monitor the voltage and current drawn by rotary electric motor 122 during forward rotation of motor 122.

In response to the change in current for a period of time being greater than the stored threshold value 472, processor 452 triggers the engagement of braking mechanism 200 by turning on solenoid 252 at block 486. When solenoid 252 is turned on, the magnetic field generated by solenoid 252 attracts the steel flange 288 and overcomes the spring force of coil spring 350, thereby moving flange 288 and the attached plunger 280 downwardly until flange 288 contacts with the top surface 254 of solenoid 252. At the same time, the downward movement of plunger 280 forces gear tooth 304 into engagement with teeth 374 of rack 360, locking rack 360 to handpiece 102. When gear tooth 304 is engaged with teeth 374, drill bit 180 cannot be advanced relative to tissue protector 420, thereby preventing any further advancement of drill bit tip 183 beyond the distal side 494 of bone 490. Any additional rotation of drill bit 180 or application of axial force by the medical practitioner does not result in further advancement of drill bit 180.

The actuation of solenoid 252 stops the movement of rack 360 relative to handpiece 102 and also results in a like cessation of the axial advancement of drill bit 180. Therefore, after the drill bit 180 has cut through the bone 290, drill bit 180 is prevented from further advancement beyond distal side 494 thereby avoiding cutting any tissue adjacent to the bone bore. Method 480 then ends.

III. Rotary Surgical Drill with End Mounted Brake Having an External Telescoping Rack FIGS. 16-19 illustrate another embodiment of a rotary surgical drill 500 that has an end mounted brake mechanism 520. Rotary surgical drill 500 comprises a handpiece 102, chuck assembly 140, drill bit 180, controller 450 and brake mechanism 520. Rotary surgical drill 500 shares many of the same components as rotary surgical drill 100 of FIG. 1. In the discussion of rotary surgical drill 500, components that are common to rotary surgical drill 100 will be referred to using the same reference numbers.

Rotary surgical drill 500 includes handpiece 102 that contains the rotary electric motor 122. Handpiece 102 of FIGS. 16-19 is the same as the previously described handpiece 102 of FIG. 1, except that an elongated sleeve 502 has been added to the top of case or upper housing 103. In one embodiment, sleeve 502 is integrally formed with case or upper housing 103. Sleeve 502 is parallel to the axis of case 103 and has a proximal end 504 and a distal end 506. An elongated round lumen 508 is defined within the interior of sleeve 502 and extends the entire length of sleeve 502. Lumen 508 is dimensioned to receive the proximal end of rack 360. A V-shaped opening 510 is formed toward the center of sleeve 502. The V-shaped opening 510 is dimensioned to receive a magnifying lens 512 that includes a measurement line or indicator line 514. The measurement line 513 is oriented perpendicular to the axis of sleeve 502.

A. Brake Mechanism

Figure 18:
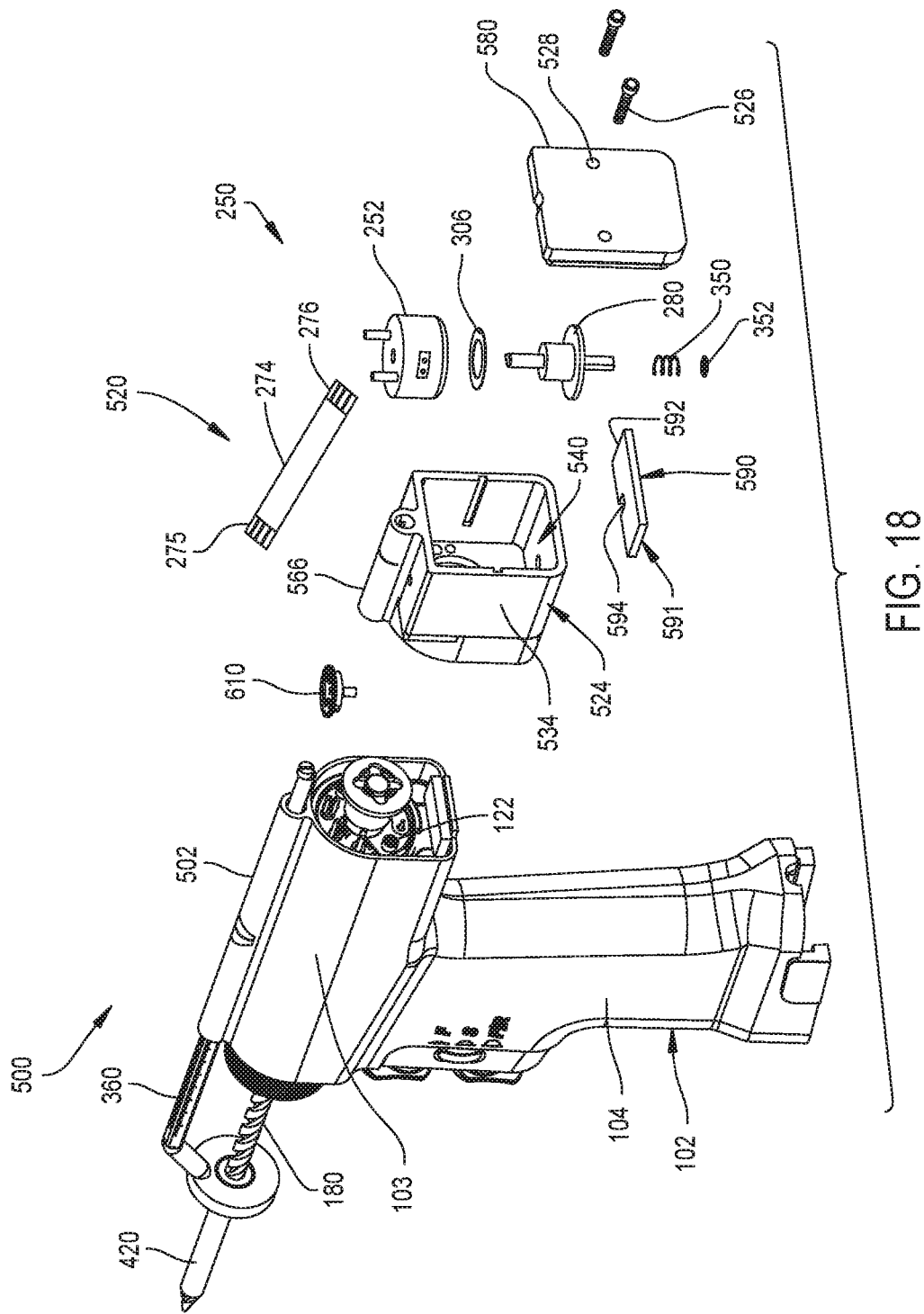
FIG. 18 is a partial rear perspective exploded view of components of the rotary surgical drill of FIG. 16.
Figure 19:
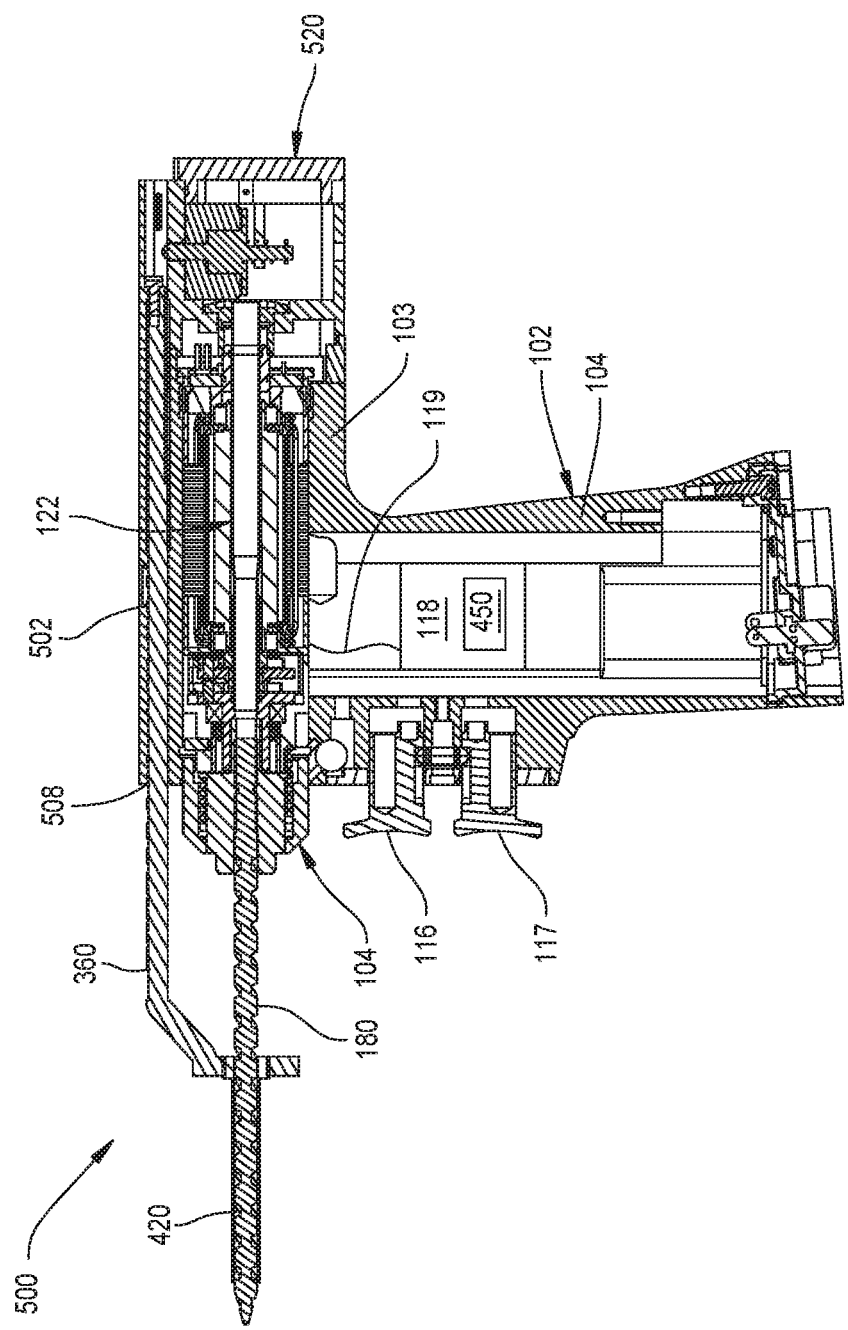
FIG. 19 is a side cross-sectional view of the rotary surgical drill of FIG. 16.

End mounted brake mechanism 520 is mounted to the proximal end 107 of case or upper housing 103. End mounted brake mechanism 520 comprises a linear actuator 250 and a telescoping rack or rod 360 that are mounted in an actuator housing 524. Actuator housing 524 is mounted to handpiece 102. Specifically, the actuator housing 524 is mounted to upper housing 103 adjacent to proximal end 107 by screws 526 (FIG. 18).

Figure 21:
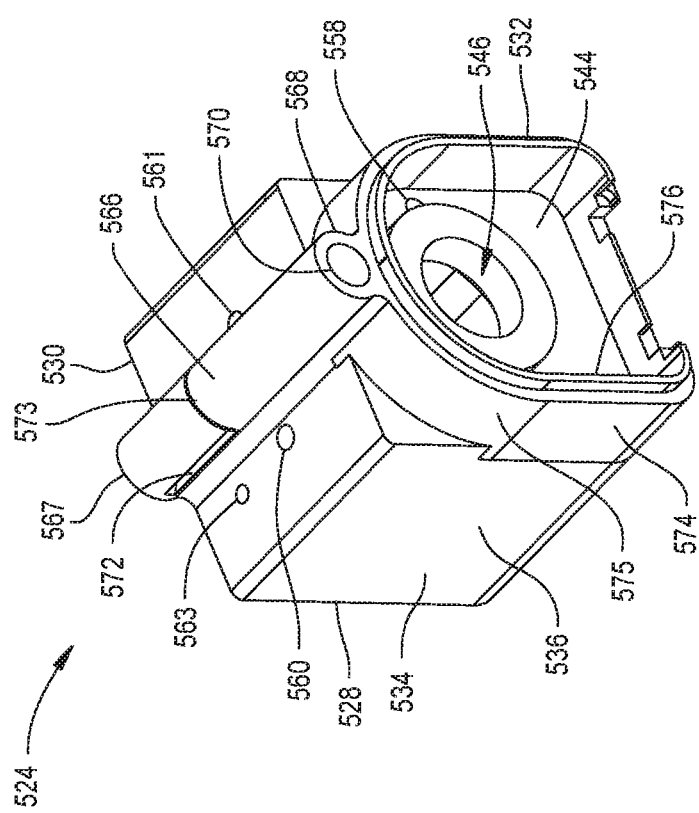
FIG. 21 is a front perspective view of the brake mechanism housing.
Figure 22:
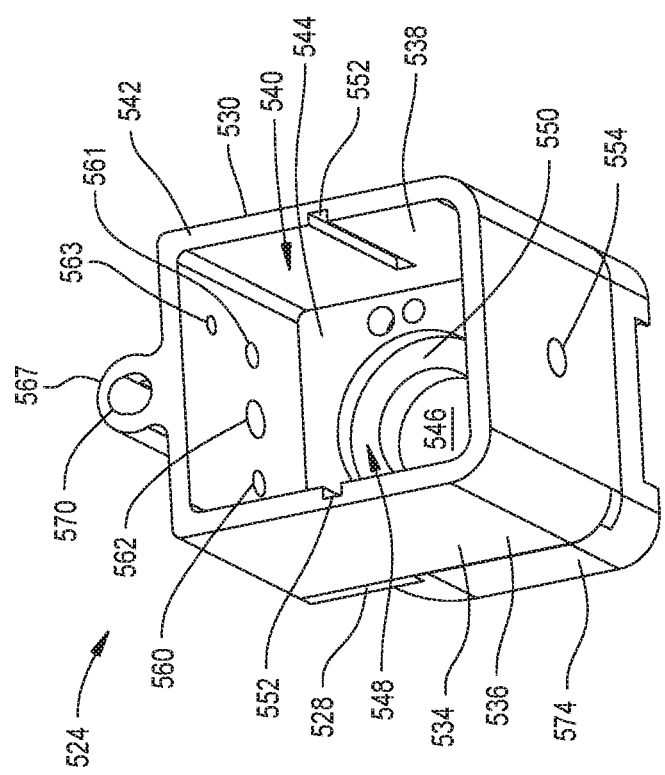
FIG. 22 is a rear perspective view of the brake mechanism housing.
Figure 23:
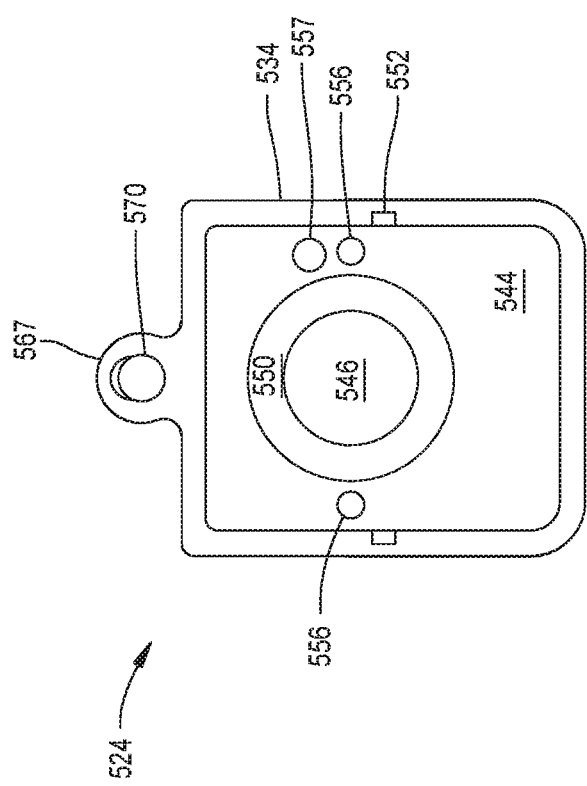
FIG. 23 is a rear view of the brake mechanism housing.

Turning to FIGS. 21, 22 and 23, details of the actuator housing 524 will now be described. The actuator housing 524 can be formed from suitable materials such as machined metal. Actuator housing 524 is generally rectangular in shape and has a central body 528. Housing 524 has a proximal end 530 and a distal end 532. Central body 528 is defined by four orthogonal sides 534 that have orthogonal outer surfaces 536 and orthogonal inner surfaces 538. Inner surfaces 538 define an interior actuator cavity 540 that opens in a proximal direction. A proximal face 542 is located on the proximal end of sides 534. The actuator cavity 540 terminates at a dividing wall 544. Wall 544 has a center thru bore 546 and a counter bore 548 that is defined by a step 550. Counterbore 548 faces into actuator cavity 540.

A pair of diametrically opposed grooves 552 are formed on the inner surfaces 538 of opposed vertical sides 534. Grooves 552 extend from proximal face 542 partially towards wall 544. An aperture 554 is defined in the horizontal bottom side 534. A pair of diametrically opposed holes 556 are defined through wall 544 on opposite sides of counterbore 548. Another hole 558 is defined through wall 554 above one the holes 556. Four apertures 560, 561, 562 and 563 are formed through horizontal top side 534.

An elongated tube 566 is formed with and located above the top horizontal side 534. Tube 566 extends the length of actuator housing 524 and has a proximal end 567 and a distal end 568. A lumen 570 extends entirely through tube 566. A projection 571 (FIG. 20) extends downwardly from the upper inner surface defined by lumen 570 slightly into lumen 570. Lumen 570 is dimensioned so as to receive the proximal end of rack 360. The hole 562 is contiguous with lumen 570 such that an opening is formed between interior cavity 540 and lumen 570. A gear slot 572 is defined in the base of tube 566 towards distal end 567.

A D-shaped wall 574 extends perpendicularly away from the distal face of dividing wall 544. Wall 574 has an outer surface 575. The terminal end of wall 574 has a protruding lip 576 that extends away therefrom.

The actuator housing 524 is mounted to proximal end 107 of upper housing 103. The D-shaped wall 574 is positioned within the interior of upper housing 103 in an overlapping relationship with proximal end 107. With additional reference to FIG. 18, a cover 580 is mounted over actuator cavity 544 and the proximal face 542 of actuator housing 524. Cover 580 can be formed from injection molded plastic or machined metal. Cover 580 has a pair of diametrically opposed holes 582 that extend through cover 580. Screws 526 hold cover 580 and actuator housing 524 to upper housing 103 of handpiece 102. Screws 526 extend through holes 582, actuator cavity 540, holes 556 and are received in threaded bores (not shown) in the proximal end 107 of upper housing 103.

Figure 20:
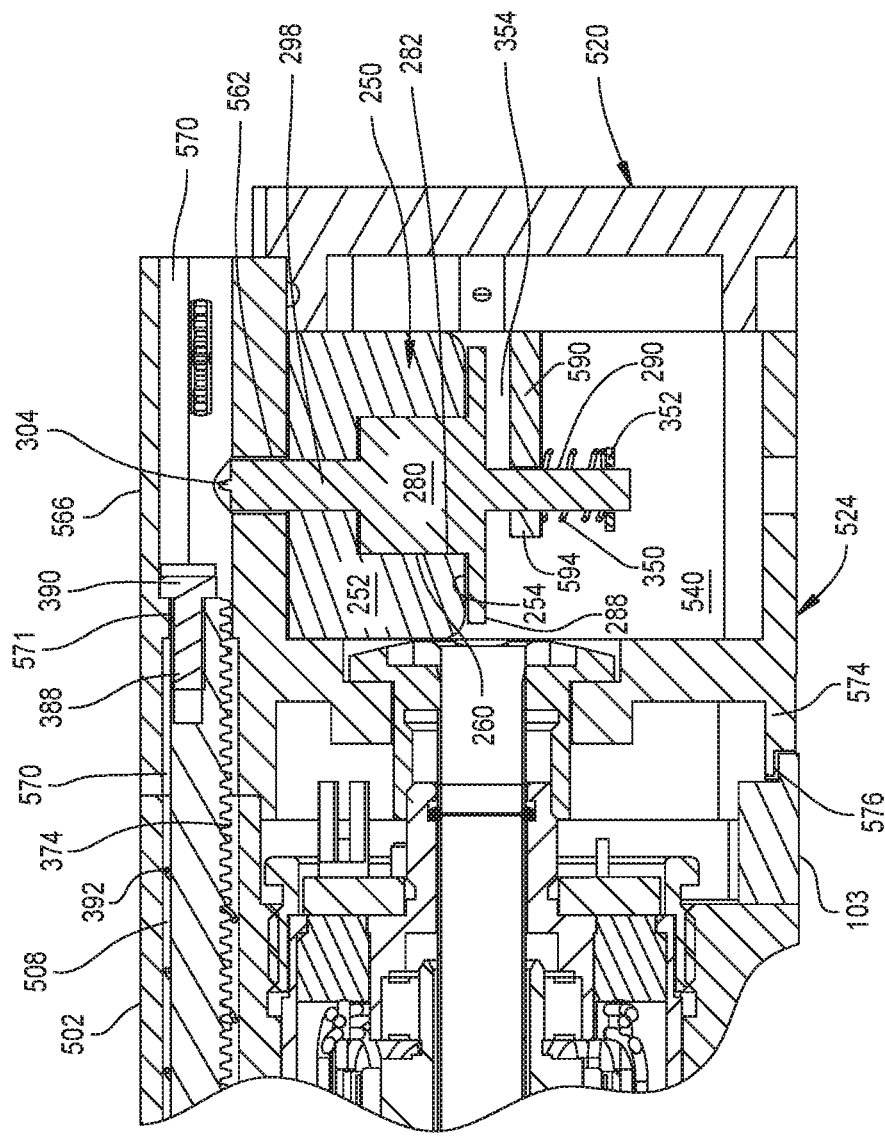
FIG. 20 is an enlarged cross-sectional view of the brake mechanism of FIG. 16.

Turning to FIGS. 18, 20 and 22, the linear actuator 250 is mounted within actuator cavity 540. Solenoid 252 is mounted in cavity 540 such that the solenoid bottom surface 256 is adjacent and resting on the inner surface of top side 534 and pins 266 extend into and are retained in apertures 560 and 561. In one embodiment, apertures 560, 561 and pins 266 are dimensioned such that pins 266 are press fit into holes 560, 561. The flexible cable 274 extends from solenoid 252 and is routed through bore 546. The other end 276 of the flexible cable 274 is electrically connected to terminals (not shown) located in handpiece upper housing 103. The terminals on end 276 are electrically connected to PCB 118. The plunger 280 is mounted in solenoid 252. Plunger hub 282 is mounted in solenoid bore 260 with the cylindrical shaft portion 298 extending through bore 562. A washer 306 is mounted over plunger hub 282 and rests against the bottom face of flange 288. The plunger flange 288 extends over the surface 254 of solenoid 252.

A planar rectangular spring plate 590 has ends 591 and 592 and a center recess 594. Ends 591 and 592 rest in and are supported by housing grooves 552. The spring plate 590 spans across the width of cavity 540 extending between the interior faces of vertical side walls 534. A coil spring 350 surrounds plunger post 290. A nut 352 is threaded onto the threads 294 (FIG. 8B) of post 290. The coil spring 350 is compressed between nut 352 and the bottom side of spring plate 590. Coil spring 350 biases plunger 280 in a downward direction away from solenoid 252.

A space or gap 354 (FIG. 20) is defined between the top side of spring plate 590 and the bottom surface 254 of solenoid 252. The flange 288 of plunger 280 can move in gap 354 between a first position when solenoid 252 is de-energized or turned off and coil spring 350 biases flange 288 into contact with the top side of spring plate 290. When solenoid 252 is energized or turned on, the magnetic field generated by solenoid 252 attracts the steel flange 288 and overcomes the spring force of coil spring 350, thereby moving flange 288 into contact with the bottom surface 254 of solenoid 252.

Figure 24:
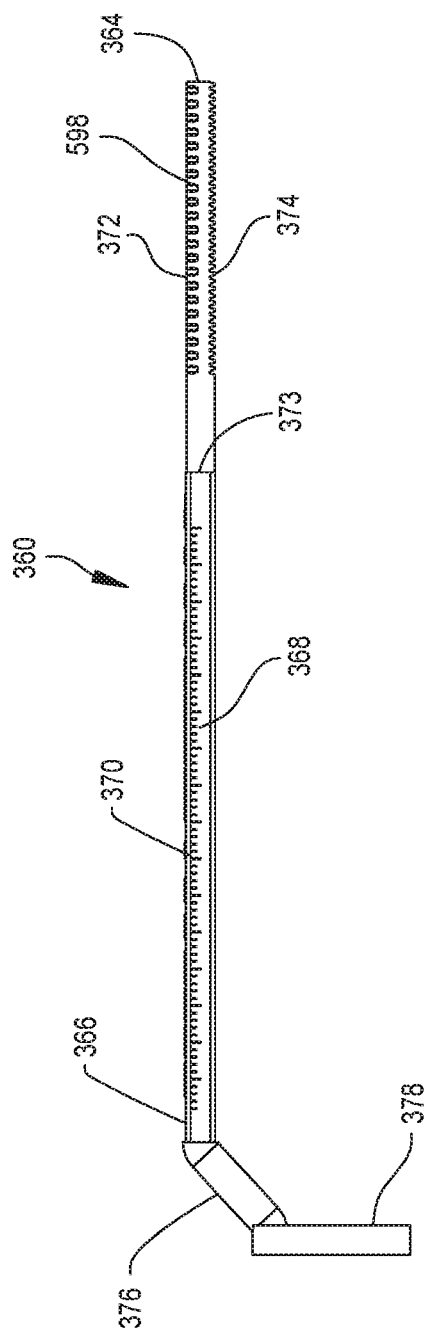
FIG. 24 is a side view of the rack used with the rotary surgical drill of FIG. 16.

With reference to FIG. 24 additional features of telescoping rod or rack 360 used with rotary surgical drill 500 are shown. Telescoping rack 360 is the same as previously described with reference to rotary surgical drill 100 except that gear teeth 374 have been moved from the top horizontal side 368 of proximal section 372 to the bottom horizontal side 368 of proximal section 372 and depth gauge teeth 598 have been added to one of the vertical sides 368 of proximal section 372. Depth gauge teeth 598 are positioned above gear teeth 374.

Figure 16:
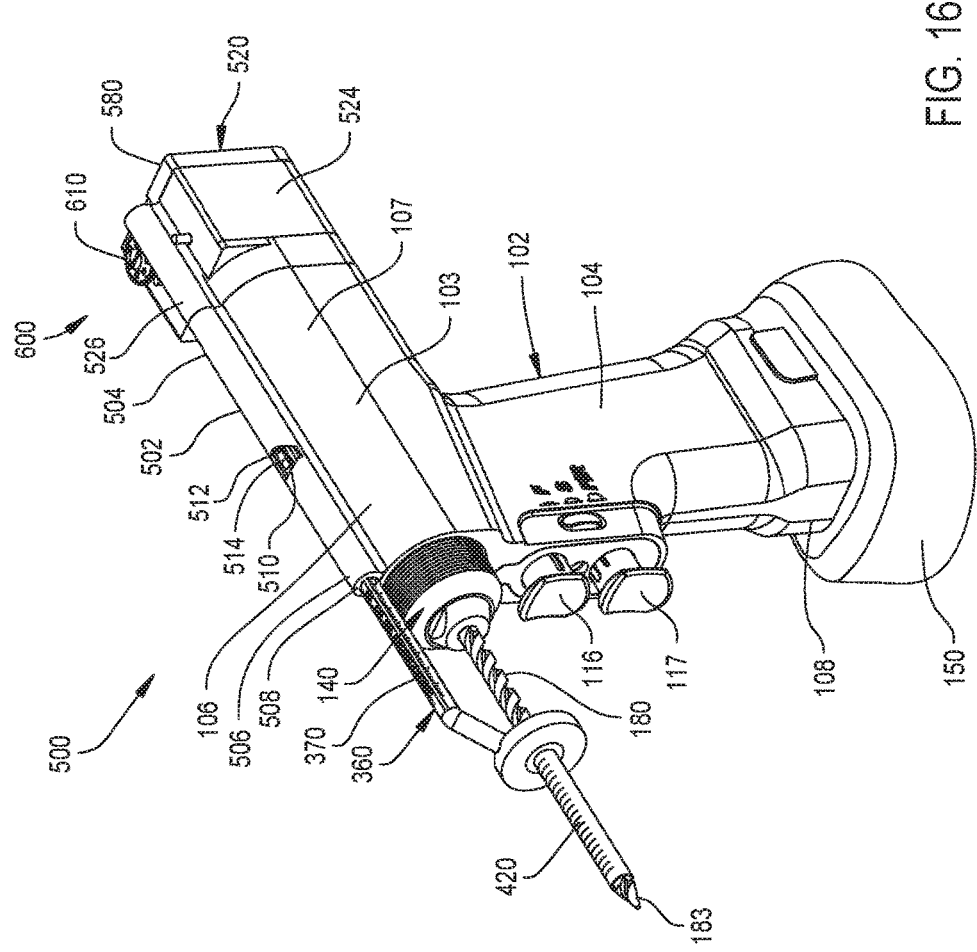
FIG. 16 is an overall perspective view of another embodiment of a powered rotary surgical drill having an end mounted brake mechanism with an external telescoping rack in accordance with the present invention.
Figure 17:
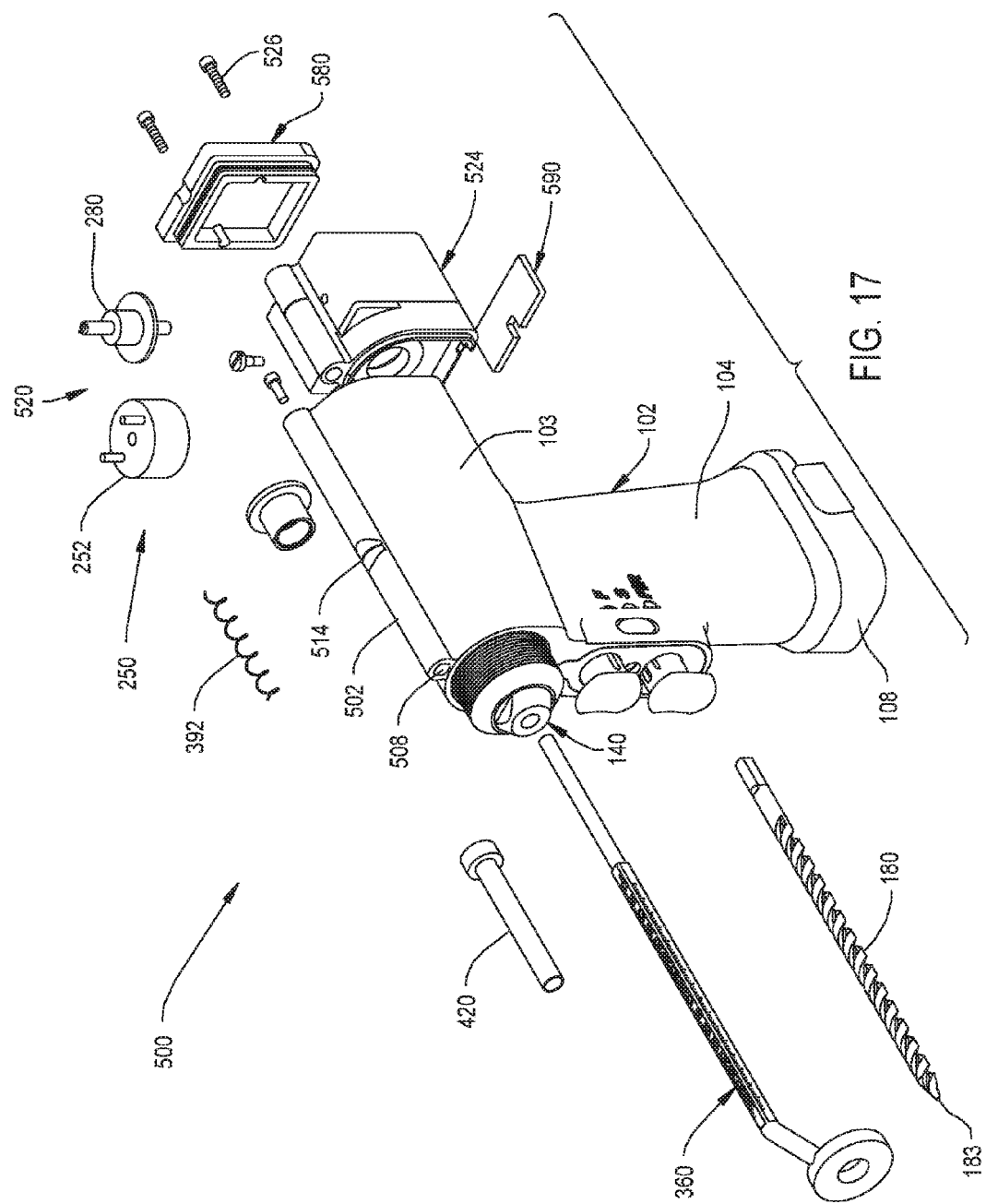
FIG. 17 is a partial front perspective exploded view of components of the rotary surgical drill of FIG. 16.

Rack 360 is mounted in lumen 508 within sleeve 502 and in lumen 570 within tube 566 for telescoping or sliding movement. With reference to FIGS. 16, 17 and 20, rack 360 can slide or telescope in a linear manner in proximal and distal directions relative to upper housing 103 and actuator housing 524. A coil spring 392 is located in lumen 508 partially surrounding the center section 362 of rack 360. The distal end of the coil spring 392 rests against step 373 (FIG. 24) and the proximal end of the coil spring 362 rests against projection 571 (FIG. 20) that extends into lumen 570. Coil spring 392 biases rack 360 in a distal direction away from handpiece 102. During assembly, coil spring 392 is placed over proximal end 364 and the proximal end 364 is inserted into the distal opening of lumen 508. Rack 360 is formed with a threaded bore 388 that extends from proximal end 364 partially into proximal section 372. Bore 388 receives a screw 390 after rack 360 has been inserted into lumen 570. When rack 360 moves in a distal direction, eventually the head of screw 390 will abut the projection 571 within lumen 570. Screw 390 prevents the removal of rack 360 from housing 524 and lumen 508.

Referring to FIGS. 16 and 24, a linear measurement scale 370 is affixed to one or more sides 368 of rack 360 within center section 362. Linear measurement scale 370 can include graduated marks and indicia such as numbers. Measurement scale 370 can be used to measure the length of the drill bit 180 that is inserted into a bone bore. Measurement scale 370 is read through magnifying lens 512. Measurement scale 370 is read at the intersection of measurement line or indicator line 514 with measurement scale 370. Magnifying lens 512 magnifies the indicia on measurement scale 370 for easier reading by the medical practitioner.

Figure 25:
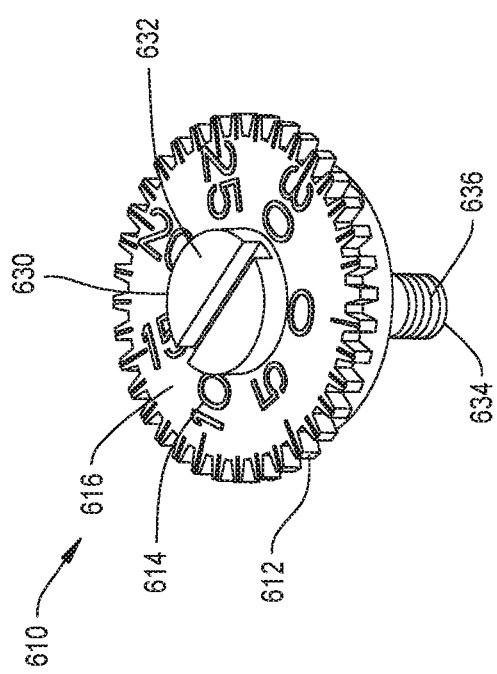
FIG. 25 is a perspective view of a depth gauge gear.
Figure 26:
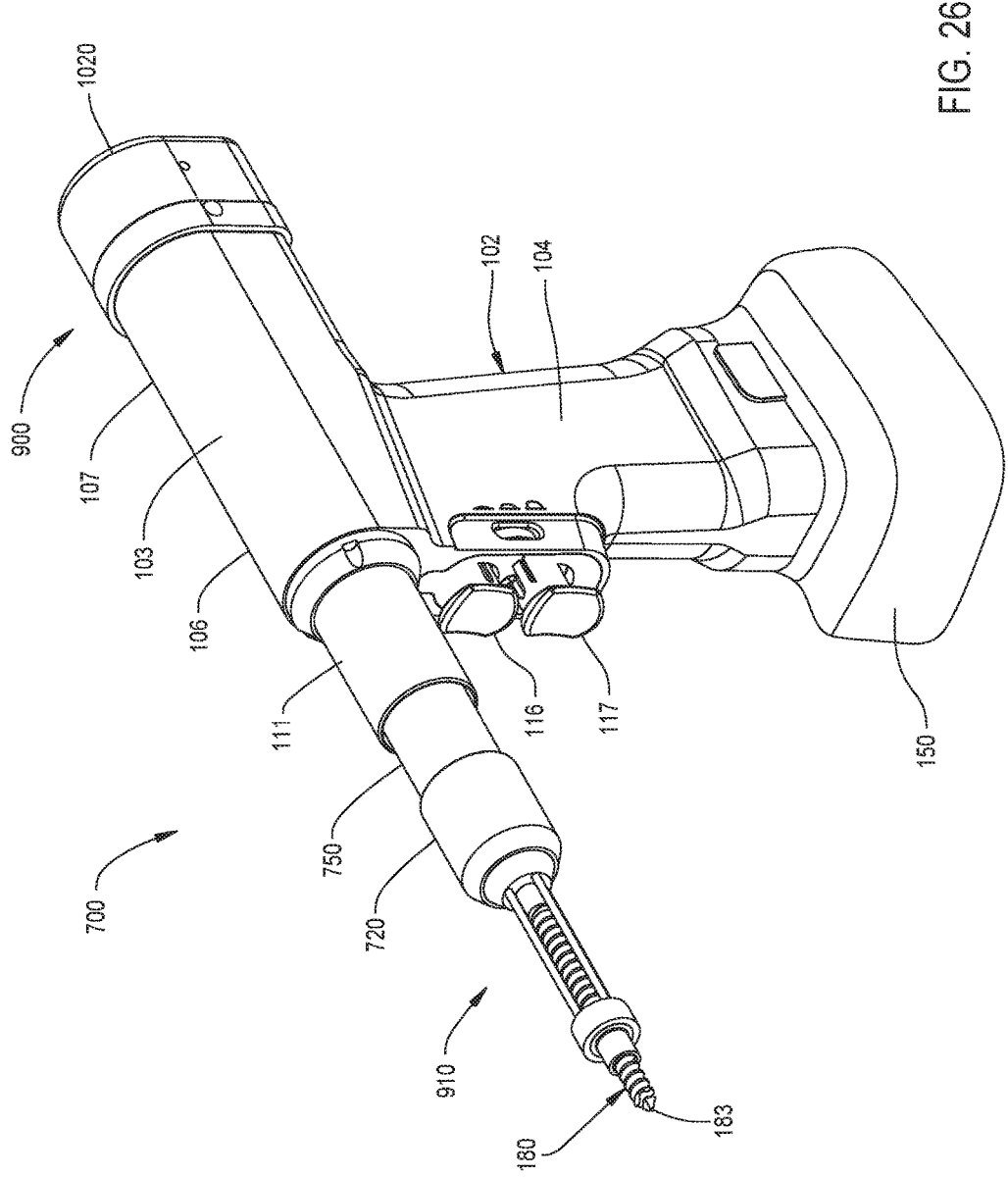
FIG. 26 is an overall perspective view of another embodiment of a powered rotary surgical drill having an end mounted brake mechanism with an internal telescoping rack in accordance with the present invention.

An additional or second depth gauge 600 is positioned on the top side 534 of actuator housing 524. Depth gauge 600 comprises gear 610 and rack 360. Turning to FIGS. 16, 24 and 25, depth gauge 600 includes a depth gauge gear 610 and a shoulder screw 630. Depth gauge gear 610 has teeth 612 formed on the outer circumference of gear 610. Measurement indicia 614 such as numbers are disposed on the top surface 616 of gear 610. Shoulder screw 630 has a head 632 and a shaft 634 with external threads 636. Gear 610 is mounted above the top side 534 of actuator housing 524. Shoulder screw 630 extends through a hole in gear 610 and into threaded hole 563 (FIG. 21). Threads 636 mate with the threads of hole 563. Gear 610 is free to rotate about shoulder screw 630.

The gear teeth 612 extend into and through housing slot 572 (FIG. 21) and into engagement with the depth gauge teeth 598 on the side of rack 360. The linear movement of rack 360 causes depth gauge teeth 598 to rotate gear 610. The indicia 614 are calibrated to the position of rack 360 relative to handpiece 102. An alignment mark 573 (FIG. 21) can be placed on tube 566. The depth gauge 600 is read from the indicia 614 where indicia 614 align with alignment mark 573. Depth gauge 600 is calibrated to correspond to the position of rack 360 and provide a numerical readout of a distance that rack 360 is extended from or inserted into tube 566 which corresponds to a measure of the length of the drill bit 180 that is inserted into a bone bore.

The remaining components of rotary surgical drill 500 including controller 450 and the electrical connections shown in the electrical schematic (FIG. 13) are the same as previously described for rotary surgical drill 100. Controller 450 controls the operation of braking mechanism 520.

B. Operation

The operation of rotary surgical drill 500 is substantially similar as previously described in FIGS. 14A-14C for the operation of rotary surgical drill 100. When drill bit 180 is drilling into bone 490, as shown in FIGS. 14A and 14B, rotary surgical drill 500 operates in the same manner as rotary surgical drill 100.

With reference to FIGS. 13, 14C, 17 and 20, eventually, the drill bit tip 183 cuts through the distal side 494 of bone 490 in which the bore 498 is being formed. When the drill bit cuts through the distal side 494 of bone 490, the frictional force created by the drill bit 180 rubbing against the bone 490 rapidly decreases. The current drawn by motor 122 will rapidly increases. The speed of drill bit 180 also increases. The sudden drop in the current drawn by the motor over a time period is measured or sensed by sensor 464 and transmitted as an electrical signal to controller 450. In one embodiment, the change in current or current drop over a time period can have units of milliamps per second. Processor 452, which is executing braking module software 470, compares the received change in current data from sensor 464 to a pre-determined threshold change in current or current drop level stored in sensor parameter threshold values 472.

In response to the received change in current being greater than the threshold change in current level, processor 452 triggers the engagement of braking mechanism 520 by turning on solenoid 252. When solenoid 252 is turned on, the magnetic field generated by solenoid 252 attracts the steel flange 288 and overcomes the spring force of coil spring 350. Flange 288 and the attached plunger 280 move upwardly until flange 288 contacts with the surface 254 of solenoid 252. At the same time, the upward movement of plunger 280 forces gear tooth 304 into engagement with gear teeth 374 of rack 360, locking rack 360 to handpiece 102. When gear tooth 304 is engaged with gear teeth 374, handpiece 102 is prevented from advancing distally forward towards the drill stop 420. By extension this prevents the advancement of the drill bit 180. Thus, the like first embodiment of the invention this embodiment of the invention reduces the likelihood that an advancing drill bit will damage tissue 497 adjacent to the distal side 494 of the bone bore.

After braking mechanism 520 has stopped advancement of the drill bit 180, the length of the drill in the bone bore 498 is equal to the distance between the distal end 430 of tissue protector sleeve 424 and the distal tip 183 of drill bit 180. This length is the approximate length that is required for a bone screw that is to be inserted into the bone bore. The linear measurement scale or depth gauge 370 that is affixed to one or more sides 368 of rack 360 is calibrated to correspond to the length of the drill bit 180 that extends beyond the distal end 430 of tissue protector 420. Measurement scale 370 is read by the medical practitioner through magnifying lens 512 at the intersection of measurement line 514 with measurement scale 370.

The length of the drill in the bone bore 498 can also be read from depth gauge 600. Depth gauge 600 is calibrated to correspond to the length of the drill bit 180 that extends beyond the distal end 430 of tissue protector 420. The depth gauge 600 is read by the medical practitioner from the indicia 614 (FIG. 25) where indicia 614 align with alignment mark 573 (FIG. 21).

Depth gauges 370 and 600 allow for the correct length of bone screw to be selected by the medical practitioner to match the depth of the bone bore. Depth gauges 370 and 600 can assist in preventing bone screws that are too long or too short from being selected for use.

IV. Rotary Surgical Drill with End Mounted Brake Having an Internal Telescoping Mechanism FIGS. 26-29 illustrate another embodiment of a rotary surgical drill 700 that has an end mounted brake mechanism 900. Rotary surgical drill 700 comprises a handpiece 102, chuck assembly 720, drill bit 180, controller 450 and brake mechanism 900. Rotary surgical drill 700 shares many of the same components as rotary surgical drill 100 of FIG. 1. In the discussion of rotary surgical drill 700, components that are common to rotary surgical drill 100 will be referred to using the same reference numbers. Rotary surgical drill 700 has a handpiece 102 that contains the rotary electric motor 122. Handpiece 102 of FIGS. 26-29 is substantially similar to the previously described handpiece 102 of FIG. 1. Chuck assembly 720 of FIGS. 26-30 is different than chuck assembly 140 of FIG. 1.

A. Chuck and Drill Bit Retainer Assemblies

Figure 27:
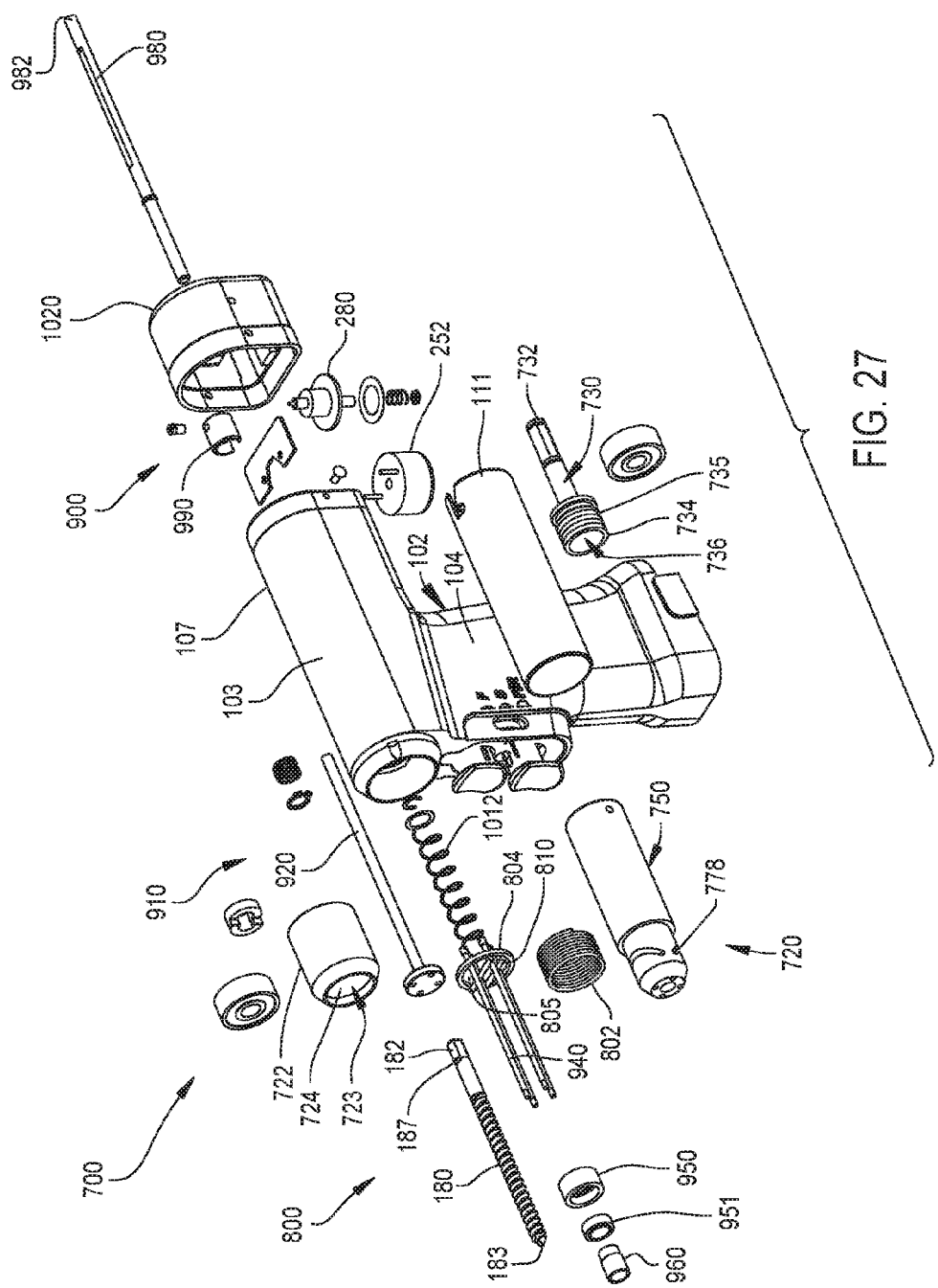
FIG. 27 is a front perspective exploded view of components of the rotary surgical drill of FIG. 26.
Figure 28:
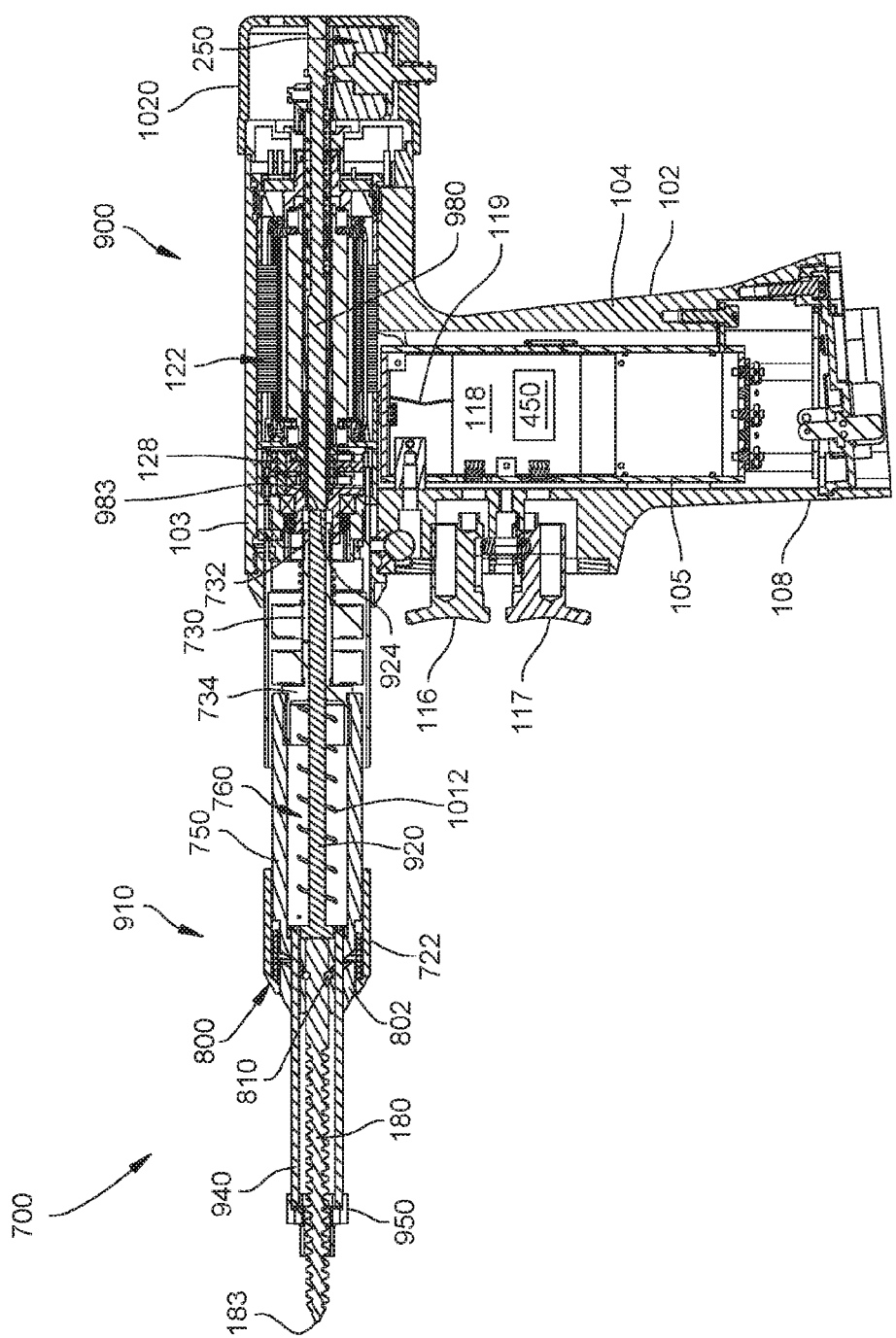
FIG. 28 is cross-sectional view of the powered rotary surgical drill of FIG. 26.

As seen in FIG. 27, chuck assembly 720 comprises a release collar 722, an inner coupler 730 and an outer coupler 750. The inner coupler 730 has a proximal end 732 affixed to planetary gear assembly 128 (FIG. 28) and a distal end 734 affixed to outer coupler 750 (FIG. 28). External threads 735 are defined on the outer annular surface of the inner coupler distal end 734. A bore 736 extends entirely through the center of inner coupler 730. Inner coupler 730 is formed from a single piece of metal. As the motor 122 rotates, planetary gear assembly 128 drives inner coupler 730 causing a like rotation of outer coupler 750. The release collar 722 is coupled to the distal end of outer coupler 750.

Figure 30:
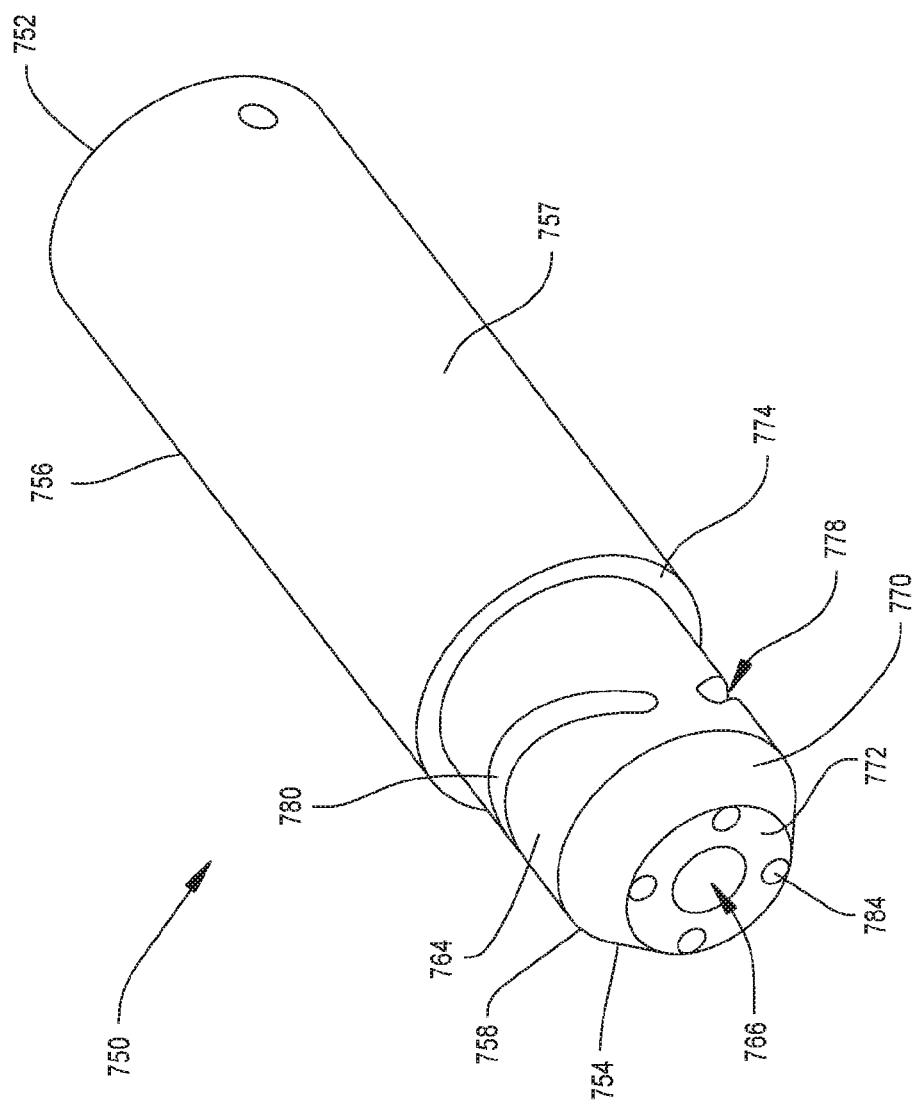
FIG. 30 is front perspective view of the outer coupler.
Figure 31:
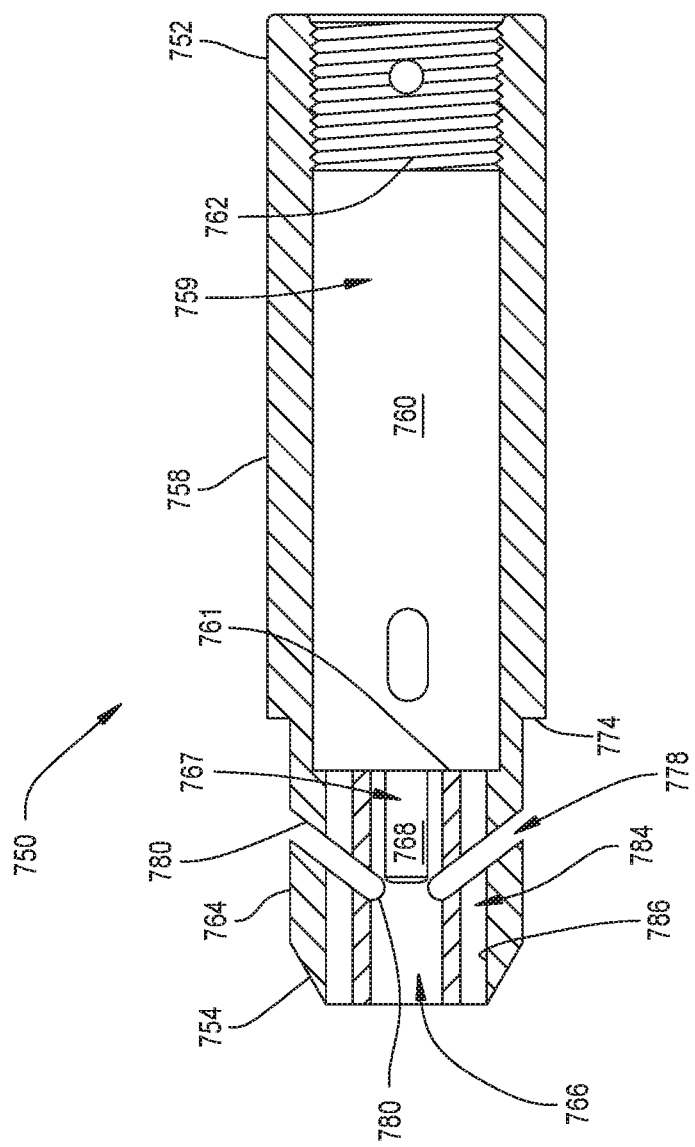
FIG. 31 is a side cross-sectional view of the outer coupler.

Referring to FIGS. 30 and 31, details of the outer coupler 750 are shown. The outer coupler 750 is formed from a single piece of metal. Outer coupler 750 is generally cylindrical in shape. The outer coupler 750 has a proximal end 752 and a distal end 754. Outer coupler 750 has two adjacent cylindrical sections, a base section 756 and a head section 758. The head section 758 has a diameter that is less than the diameter of base section 756.

Base section 756 has an outer annular surface 757 and a bore 759 that is defined by an inner annular surface 760. The bore 759 terminates at terminal wall 761. Internal threads 762 are formed on the proximal portion of inner annular surface 760. The inner coupler distal end 734 is seated in bore 759 and affixed to outer coupler 750 by the mating of inner coupler external threads 735 with the outer coupler internal threads 762.

The head section 758 has an outer annular surface 764 and a pair of coaxial bores 766 and 767. The distal most bore 766 is round and the proximal bore 767 is square. Bore 767 is defined by four opposed orthogonal surfaces 768. The head section 758 further includes an angled face 770 that extends from annular surface 764 and terminates in a distally oriented face 772 at distal end 754. An annular step 774 is defined at the junction of head section 758 and base section 756.

A pair of opposed angled arcuate slots 778 are formed on opposite sides of head section 758. Slots 778 are defined by opposed angled slot walls 780. The slots 778 begin at the outer surface 764 of head section 758, above step 774 and are angled in a distal direction inwardly toward bore 766. At the base of slot 778, an oval shaped hole 780 is defined that extends from slot 778 into bore 766.

Four spaced apart bores 784 are defined through head section 758. Bores 784 are defined by inner annular surfaces 786. The bores 784 are parallel in length to bores 766 and 768. Each of the bores 784 extend between the distal face 772 and the terminal wall 761 at the end of bore 759.

Returning to FIGS. 27 and 28 and with continued reference to FIGS. 30 and 31, a drill bit retainer assembly 800 is illustrated. The drill bit retainer assembly 800 includes outer coupler 750, release collar 722, coil spring 802, ring 804 and a pair of elongated rods or pins 810. Release collar 722 is generally cylindrical in shape and is formed from a single piece of metal. The release collar 722 has a thru bore 723 defined by an inner annular surface 724.

The drill bit retainer assembly 800 is assembled with coil spring 802 mounted over outer coupler outer annular surface 764 and the coil spring proximal end resting in contact with annular step 774. Ring 804 is placed over outer annular surface 764 and moved into contact with the coil spring distal end. The outer coupler head section 758 extends through ring hole 805. Ring 804 is moved in a proximal direction compressing spring 802 and allowing pins 810 to be inserted into outer coupler slots 778. The release of ring 804 causes coil spring 802 to bias ring 804 and pins 810 to the distal ends of slots 778 adjacent holes 780. In this position, the center of pins 810 at least partially extend through holes 780 into outer coupler bore 766.

The release collar 722 is placed over ring 804 and spring 802 such that the collar inner annular surface 724 is adjacent the spring 802 and the distal end of spring 802 rests in contact with the proximal directed surface of ring 804. The distal directed surface of ring 804 is in contact with an annular lip within release collar 722. A set screw and slot (not shown) allow release collar 722 to be movably retained to outer coupler 750.

The drill bit 180 is inserted into chuck assembly 720 by a user grasping release collar 722 and moving release collar 722 in a proximal direction such that pins 840 move away from the center axis of output coupler 750 and spring 802 is compressed. The drill bit square drive head 182 is inserted into bore 766 and moved in a proximal direction until seated in the complimentary square shaped outer coupler bore 768 (FIG. 31).

When the release collar 722 is released by the user, the spring 802 biases the release collar 722, ring 804 and pins 810 to move in a distal direction such that pins 810 move from slots 778 through holes 780 and into engagement with the complementary grooves 187 in drive head 182. With pins 810 disposed in grooves 187, the drill bit 180 is held and retained to output coupler 750. Drill bit 180 is removed from chuck assembly 720 by manually depressing release collar 722 towards case 103. This results in a like removal of pins 810 from the complementary grooves 187 allowing removal of drill bit 180 from drill bit retainer assembly 800.

B. Brake Mechanism

Figure 34:
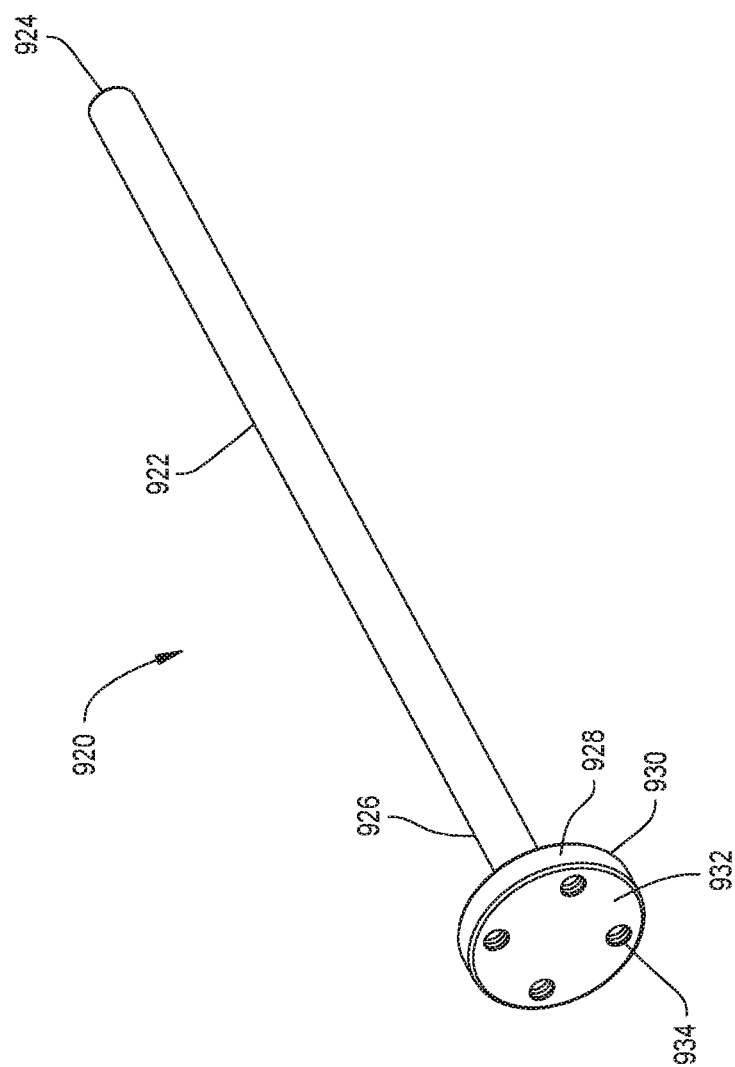
FIG. 34 is a front perspective view of the stop.

Brake mechanism 900 comprises a linear actuator 250 mounted in an actuator housing 1020 and a telescoping protector assembly 910. Telescoping protector assembly 910 is described with reference to FIG. 32. Telescoping protector assembly 910 includes an elongated stop 920, four elongated bars 940, tissue protector 950, spring cover 990 and rod or rack 980. Rack 980 is mounted for sliding movement within previously described tube 129 (FIG. 36). With specific reference to FIG. 34, stop 920 includes an elongated rod 922 with an attached head 928. Stop 920 has a proximal end 924, distal end 926 and a disk shaped head 928. Head 928 is perpendicular to rod 922 and extends over distal end 926. Head 928 further has a proximal face 930 and a distal face 932. Threaded apertures 934 are defined in head 928 and extend between the proximal face 930 and the distal face 932.

Figure 35A:
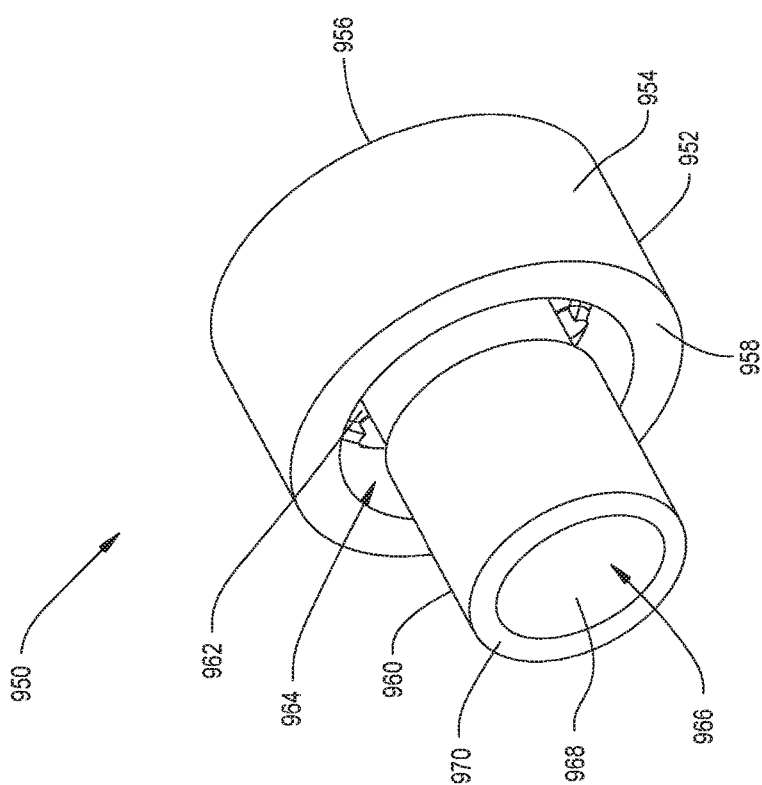
FIG. 35A is a front perspective view of the tissue protector.

Turning to FIGS. 35A and 35B, tissue protector 950 is shown. The tissue protector 950 has a tube shaped base 952. A sleeve 960 is disposed in and projects distally out of base 952. A bearing assembly 951, seen in FIG. 27, is disposed between the inner wall of the base 952 and the outer surface of the sleeve that rotatably holds the sleeve 960 to base 952. Base 952 has an outer circumferential surface 954, a proximal face 956 and a distal face 958. Sleeve 960 extends in a distal direction away from a wall 962 at the bottom of an annular slot 964 defined in distal face 958. A hole 966 extends entirely thru the base 952 and sleeve 960. Hole 966 is defined in sleeve 960 by an inner annular surface 968. Sleeve 960 terminates in a distal end 970. Four equally spaced apart apertures 972 are formed in base 952. Apertures 972 extend between proximal face 956 and distal face 958.

Figure 33:
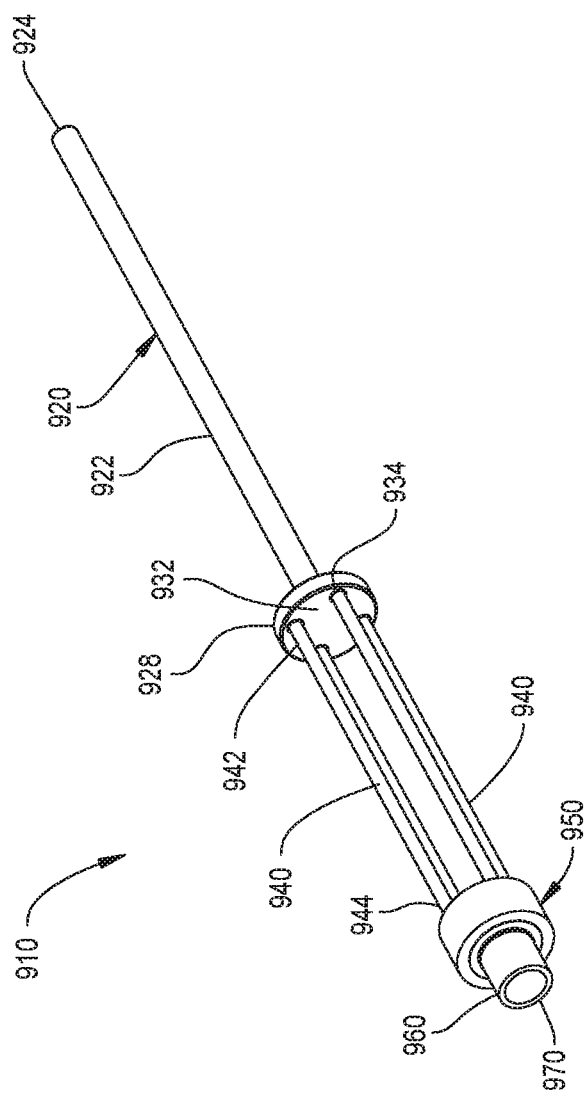
FIG. 33 is a front perspective view of the tissue protector, rods and plunger.

Referring to FIG. 33, each of the four elongated bars 940 have a threaded proximal end 942 and a distal end 944. Threaded proximal ends 942 are screwed into the threaded apertures 934 of stop head 928. The distal ends 942 are mounted thru apertures 972 (FIG. 35B) in base 952. The distal ends 972 are retained to base 952 by suitable means such as welding or swaging. The stop 920, bars 940 and tissue protector 950 can be formed from suitable materials such as metal.

Figure 37A:
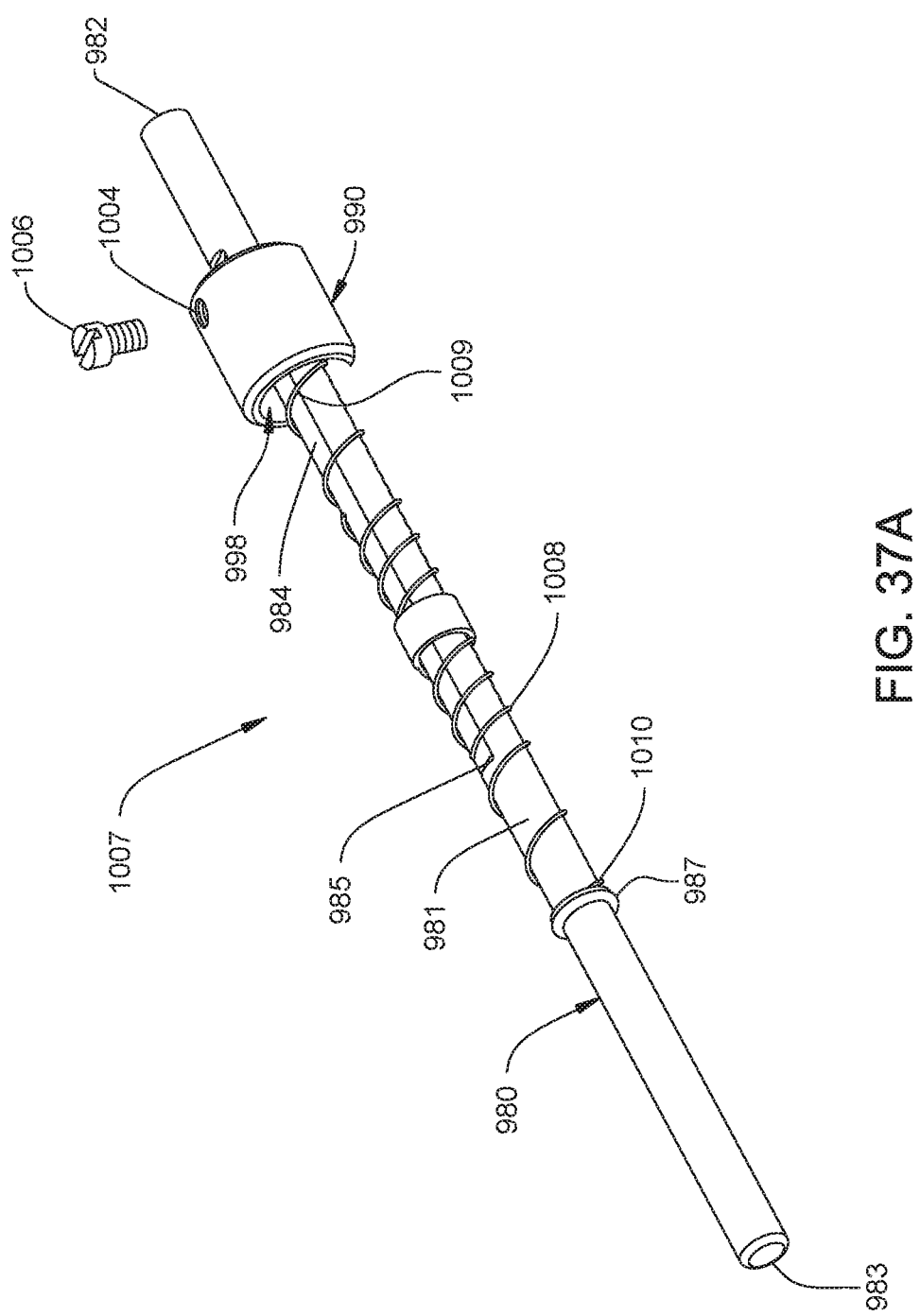
FIG. 37A is a front perspective view of the rack and coil springs.
Figure 37B:
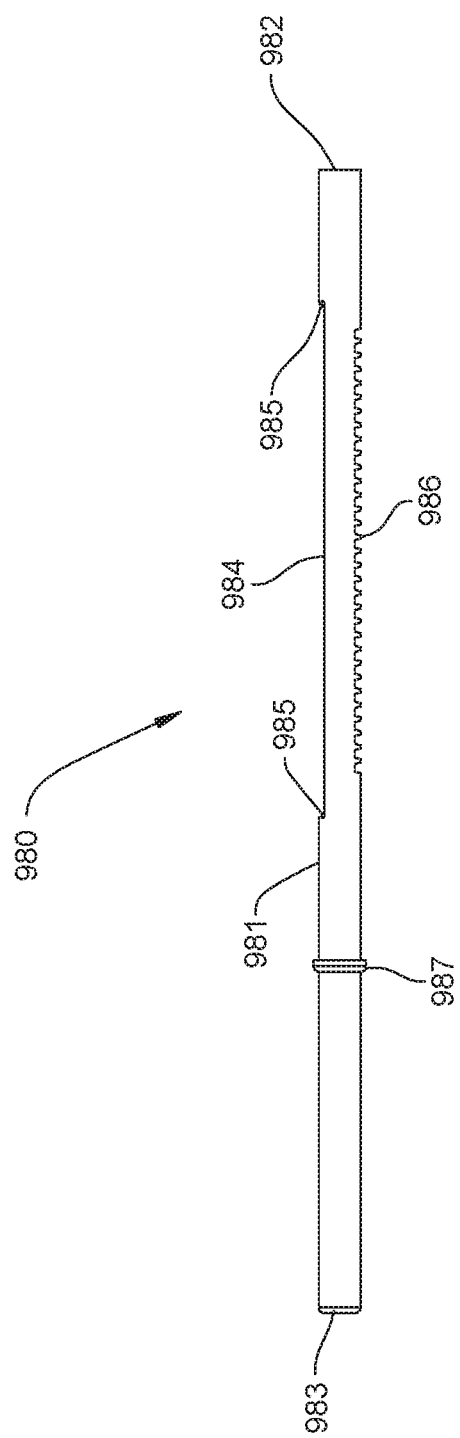
FIG. 37B is a side view of the rack.

Rack 980 is shown in FIGS. 37A and 37B. Rack 980 has an elongated shape with a round cross-sectional profile. Rack 980 can be formed from suitable materials such as metal. Rack 980 has a center section 981, a proximal end 982 and a distal end 983. A recess 984 is defined in the upper side of rack 980 between the center section 981 and the proximal end 982. Recess 984 terminates at opposed end walls 985. A set of gear teeth 986 are formed in the lower side of rack 980 between the center section 981 and the proximal end 982. Teeth 986 are dimensioned such that tooth 304 (FIG. 8B) can be engaged between two teeth 986. A flange 987 encircles rack 980 toward the center section 981.

Figure 38:
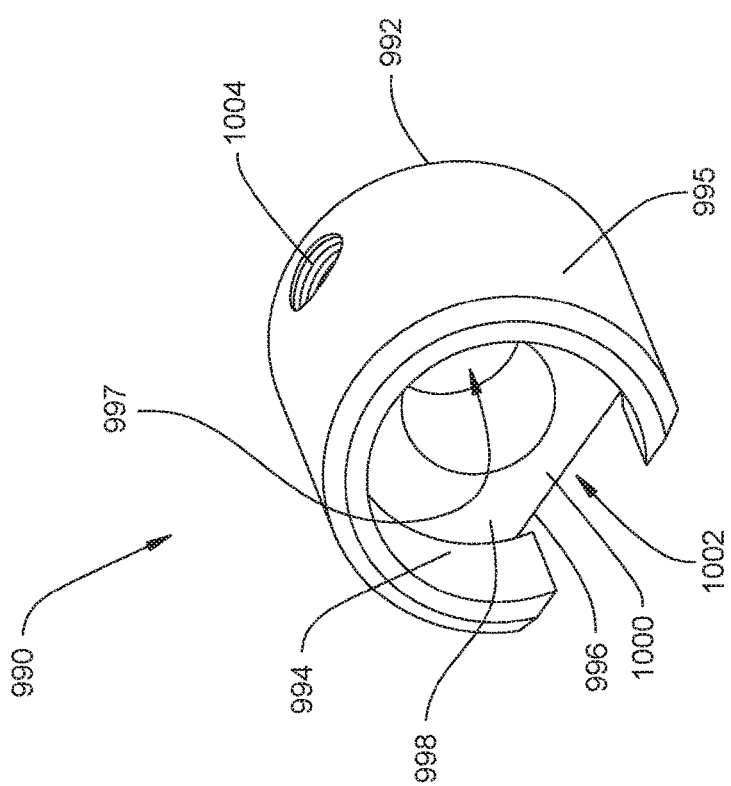
FIG. 38 is a front perspective view of the spring retainer.

Turning to FIG. 38, the spring cover 990 has a truncated cylindrical shaped with one flat side 996. Spring cover 990 has an outer circumferential surface 995, a proximal face 992 and a distal face 994. A bore 997 extends thru spring cover 990. A counter-bore 998 extends from distal face 994 in a proximal direction terminating at end wall 1000. A rectangular shaped opening 1002 is defined at the bottom of wall 1000. A threaded aperture 1004 extends from the top of outer surface 995 downwardly and ends at bore 997. Threaded aperture 1004 is dimensioned to receive a set screw 1006 (FIG. 37A).

With continued reference to FIG. 37A, rack sub-assembly 1007 is shown. A coil spring 1008 is mounted over the proximal end 982 of rack 980. Coil spring 1008 has a proximal end 1009 and a distal end 1010. Distal end 1010 abuts flange 987. The coil spring 1008 surrounds the recess 984. The spring cover 990 slides over the proximal end 982 of rack 980. The proximal end 982 extends thru bore 997. The spring cover 990 is positioned toward the proximal end of recess 984 and is coupled to rack 980 for sliding movement by set screw 1006. Rack 980 can slide in proximal and distal directions relative to spring cover 990. The set screw 1006 is screwed into threaded aperture 1004 until the terminal end of set screw 1006 extends slightly into recess 984 between the recess end walls 985. The proximal end 1009 of the coil spring abuts the end wall 1000 of spring cover 990.

Figure 29:
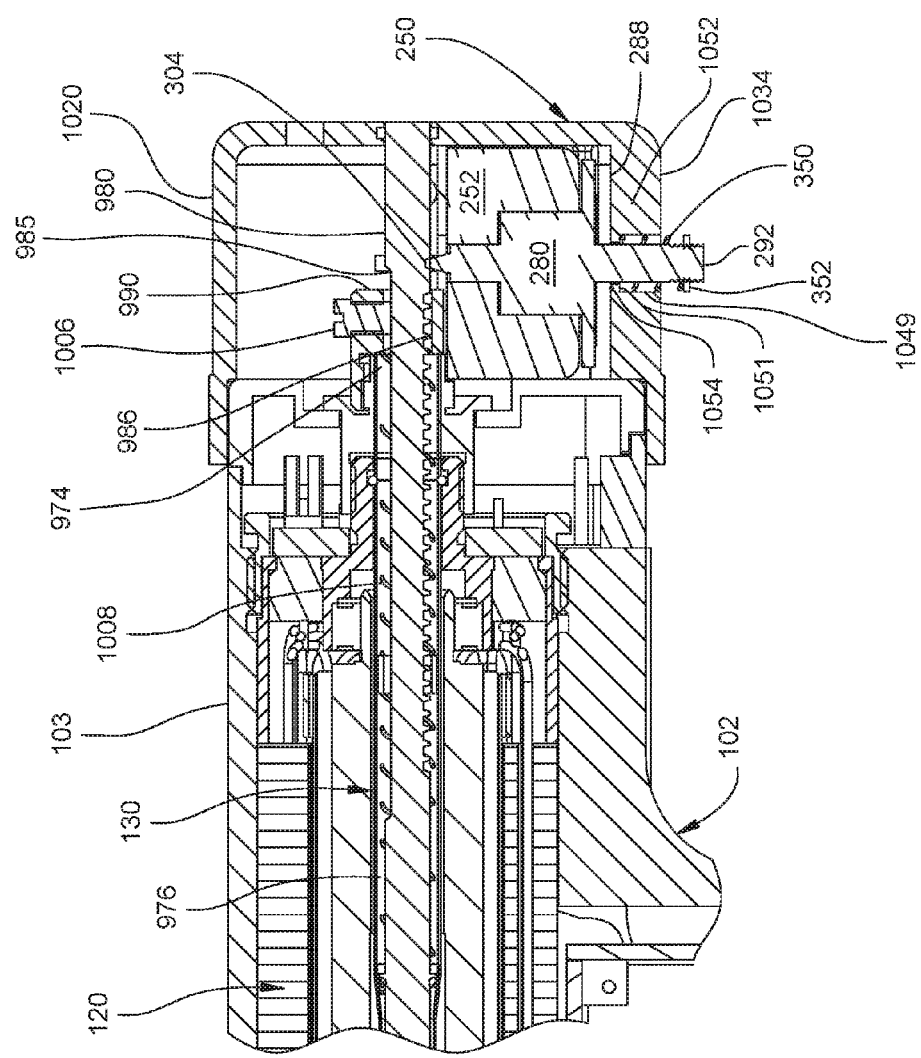
FIG. 29 is an enlarged cross-sectional view of the brake mechanism of FIG. 26.
Figure 32:
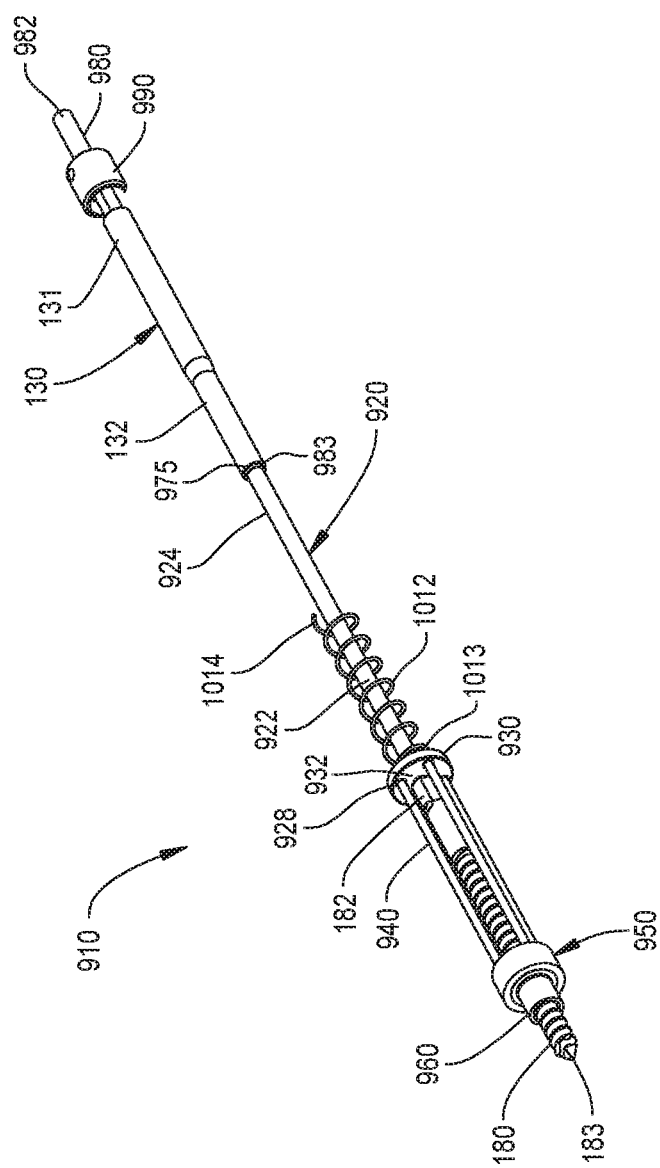
FIG. 32 is a front perspective view of the drill bit, tissue protector, rods, plunger, rack and motor shaft showing the relative orientation of the components.

The rack sub-assembly 1007 of FIG. 37A is inserted into tube 129. Referring to FIGS. 29, 32 and 36, the distal end 983 of rack 980 is inserted into the proximal opening 974 of the motor shaft and into lumen 976. Rack 980 and coil spring 1008 move into tube 129 until flange 987 abuts the interior wall of tapered section 977. In this position, the distal end 983 of the rack is located in opening 975. Rack 980 can slide within lumen 976. The travel of rack 980 in the distal direction is limited by the abutment of set screw 1006 against the proximal wall 985 in recess 984. The travel of rack 980 in the proximal direction is limited by the compression of spring 1008 and the abutment of set screw 1006 against the distal wall 985 in recess 984. Spring 1008 biases rack 980 in a distal direction relative to motor shaft 130.

Referring to FIGS. 28, 31 and 32, the stop 920 is illustrated as being mounted within outer coupler 750. Stop 920 is inserted into bore 760 such that the distal face 932 of head 928 abuts terminal wall 761 with the four bars 940 extending thru the four bores 784 of outer coupler 750 and away from outer coupler distal face 772. The tissue protector 950 is mounted to the distal ends of the four bars 940. The outer coupler 750 is inserted into shroud 111 and attached to inner coupler 730 by the mating of the outer coupler internal threads 762 with the inner coupler external threads 735 (FIG. 27). The proximal end 924 of the stop extends through the center bore 736 of inner coupler 730 and abuts against the distal end 983 of rack 982. Stop rod 922 slides within bore 736.

Another coil spring 1012 is mounted in bore 760 surrounding the distal portion of rod 922. Coil spring 1012 has a distal end 1013 that abuts the proximal face 930 of stop head 928. Coil spring 1012 further has a proximal end 1014 that abuts the base of the bore 736 within inner coupler 730. The coil spring 1012 biases stop 920 is a distal direction away from inner coupler 730. Stop 920 can travel between an extended position where head 728 abuts the terminal wall 761 of the outer coupler and a retracted position where spring 1012 is compressed.

The drill bit 180 is inserted through tissue protector 950. Specifically, the square drive head 182 is inserted through bore 966 and through the space between bars 940 and is received by drill bit retainer assembly 800. When drill bit 180 is seated and held in drill bit retainer 800, the drill bit head 182 abuts the distal face 932 of stop 920.

Figure 39:
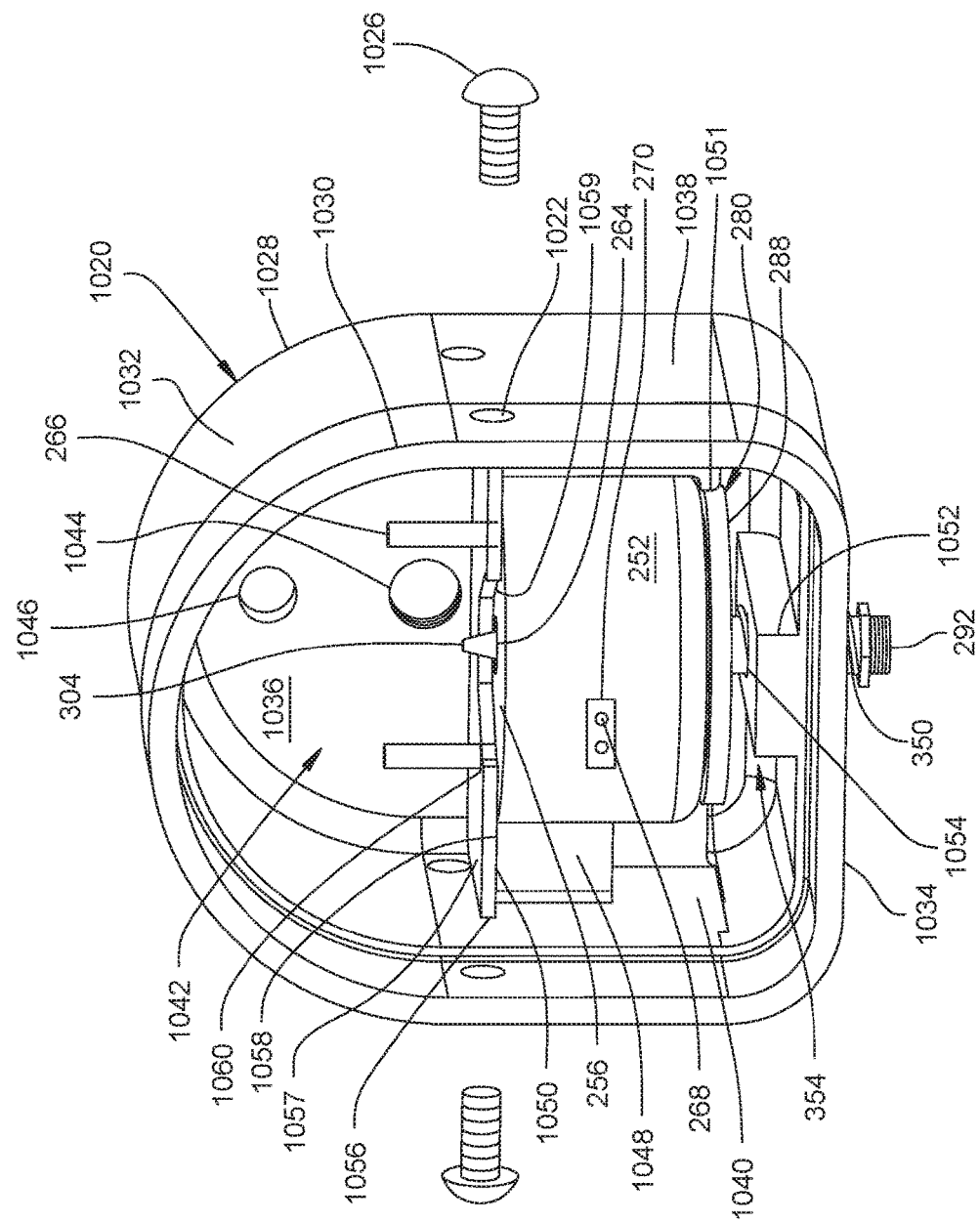
FIG. 39 is a perspective view looking into the brake housing showing the relative orientation of the components when the linear actuator is mounted in the housing.

The brake mechanism 900 further comprises a linear actuator 250 mounted in an actuator housing 1020. Referring to FIGS. 39 and 40, the actuator housing 1020 is mounted to the proximal end 107 of case or upper housing 103. Actuator housing 1020 has holes 1022 and case 103 has threaded apertures 1024. Specifically, the actuator housing 1020 is mounted to upper housing 103 adjacent to proximal end 107 by screws 1026 extending thru holes 1022 and received in threaded apertures 1024.

The actuator housing 1020 is formed from suitable materials such as machined metal. Actuator housing 1020 is generally rectangular with a D-shaped cross-section. The housing 1024 has a proximal end 1028 and a distal end 1030.

Housing 1024 is defined by a U-shaped upper wall 1032 that is attached to a planar lower wall 1034 and an end wall 1036 that covers the proximal end 1028. Housing 1024 has an outer surface 1038 and an inner surface 1040. Walls 1032, 1034 and 1036 define an interior actuator cavity 1042 that opens in a proximal direction. The end wall 1036 has two apertures, a center aperture 1044 and another aperture 1046 that is located between aperture 1044 and upper wall 1032. The proximal end 982 of rack 980 can move through center aperture 1044 when rack 980 is moved.

A pair of diametrically opposed rectangular shaped support members 1048 extend into cavity 1042 from opposite sides of U-shaped upper wall 1032. Each support member 1048 has a planar top surface 1050 and an inwardly extending lower lip 1051. A rectangular shaped block 1052 is formed on the interior facing surface of lower wall 1034 and extends upwardly into cavity 1042. A bore 1054 extends entirely thru block 1052 and lower wall 1034. A counter-bore 1049 (FIG. 29) extends from the outer surface of lower wall 1034 into block 1052. Counter-bore 1049 terminates at an end wall 1051 (FIG. 29).

A plate 1056 has ends 1055 that rest on top surface 1050 of support members 1048. Plate 1056 is attached to support members 1048 by the use of fasteners or adhesives. Plate 1056 has an upper surface 1057, lower surface 1058 and a distal facing opening 1059. A pair of apertures 1060 are defined thru plate 1056 on opposite sides of opening 1059.

The linear actuator 250 is mounted within actuator housing cavity 1042. Solenoid 252 is mounted in cavity 1042 between support members 1048 with the solenoid top surface 254 supported by lower lip 1051. The solenoid pins 266 extend into and are retained in plate apertures 1060. In one embodiment, apertures 1060 and pins 266 are dimensioned such that pins 266 are press fit into apertures 1060.

The plunger 280 is mounted in solenoid 252. Plunger hub 282 is mounted in solenoid bore 260. The D-shaped terminal section 298 of plunger 280 extends through solenoid bore 264 (FIG. 7B) with gear tooth 304 extending slightly beyond lower surface 256 and into plate opening 1059.

The plunger flange 288 extends over the surface 254 of solenoid 252. The plunger post 290 extends downwardly through the block bore 1054 and terminates at end 292 which is positioned slightly beyond the lower wall 1034. A coil spring 350 is mounted in counter-bore 1049 and surrounds plunger post 290. A nut 352 is threaded onto the threads 294 (FIG. 8B) of post 290. Coil spring 350 is compressed between nut 352 and end wall 1051. Coil spring 350 biases plunger 280 in a downward direction away from solenoid 252.

A flexible cable 274 extends from solenoid 252 and is routed into case 103. Cable end 275 is connected to terminals 268 of solenoid 252. Cable end 276 is electrically connected to terminals (not shown) located in handpiece upper housing 103 which connect with PCB 118 (FIG. 28).

A space or gap 354 is defined between the top surface of block 1052 and the bottom surface of plunger flange 288. Plunger flange 288 can move in gap 354 between a first position when solenoid 252 is de-energized or turned off and coil spring 350 biases flange 288 into contact with the top side of block 1052. When solenoid 252 is energized or turned on, the magnetic field generated by solenoid 252 attracts the steel flange 288 and overcomes the spring force of coil spring 350, thereby moving flange 288 into contact with the bottom surface 254 of solenoid 252.

The remaining components of rotary surgical drill 700 including controller 450 and the electrical connections shown in the electrical schematic (FIG. 13) are the same as previously described for rotary surgical drill 100. Controller 450 controls the operation of braking mechanism 900.

C. Operation

Figure 41A:
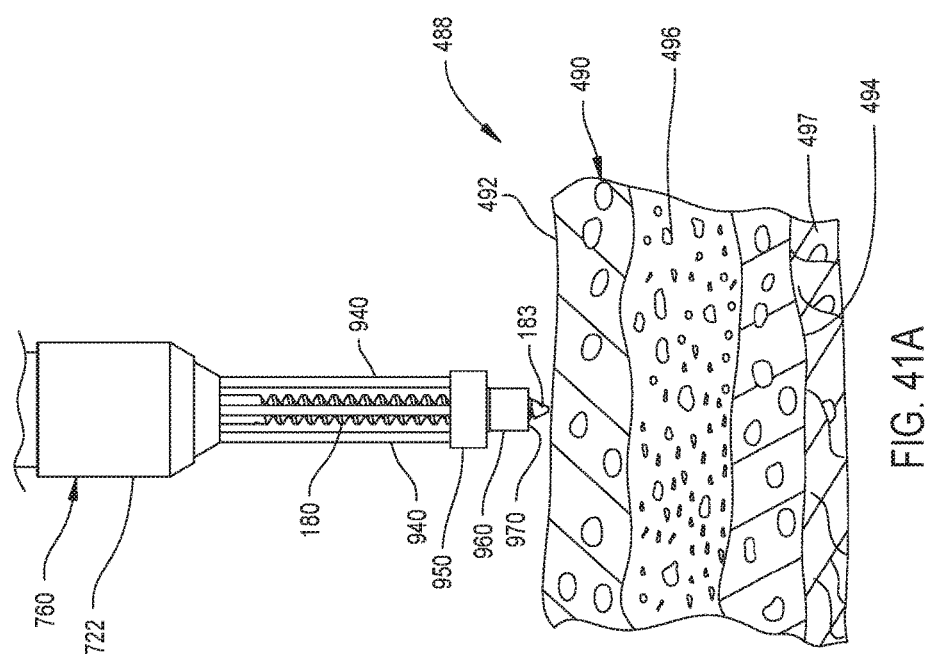
FIG. 41A is a side cross-sectional view of the tissue protector and drill bit of FIG. 26 prior to the start of drilling into a bone.

As shown in FIG. 41A, the rotary surgical drill 700 is used at a surgical site 488. The medical practitioner grasps handle 104 and directs the drill bit tip 183 to the surgical site. Drill bit 180 is used to drill one or more bores into a bone.

With further reference to FIGS. 13, 28 and 29, initially, the solenoid 252 is turned off by controller 450 such that spring 350 biases plunger 280 to a lower most position where tooth 304 is disengaged from the teeth 986 of rack 980. In this position, rack 980 is free to telescope or slide within lumen 976. Stop 920 likewise free to slide within outer coupler bore 760 and inner coupler bore 736.

Because tissue protector 950 is coupled to rods 940 which are coupled to stop 920, which is coupled to rack 980, displacement of tissue protector 950 relative to drill bit 180 causes a like displacement of rack 980. Initially, the tissue protector 950 is biased by coil springs 1012 and 1008 to a distal most position where distal end 970 is slightly drawn back from drill bit distal tip 183 causing only the distal tip 183 to be exposed as seen in FIG. 41A. In this position, the stop 920 abuts the outer coupler terminal wall 761. Also initially, the drill bit 180 is not subjected to any axial loading.

The drill bit 180 is positioned against the proximal side 492 of the bone 490 where the bone bore 498 is to be formed. The drill bit 180 is forced downwardly in an axial direction. After the drill bit 180 is so positioned, the rotary drill 700 is actuated in a forward or clockwise rotation. The combination of the rotating drill bit and the axial load placed on the drill bit results in the cutting edges of the drill bit tip 183 cutting the bone 490 so as to form a bore 498. During formation of the bone bore, the motor 122 draws a relatively high current to maintain a desired number of revolutions per minute (RPM) of the drill bit 180. The current level drawn by motor 122 is measured by sensor 464 and transmitted as an electrical signal to controller 450.

Figure 41B:
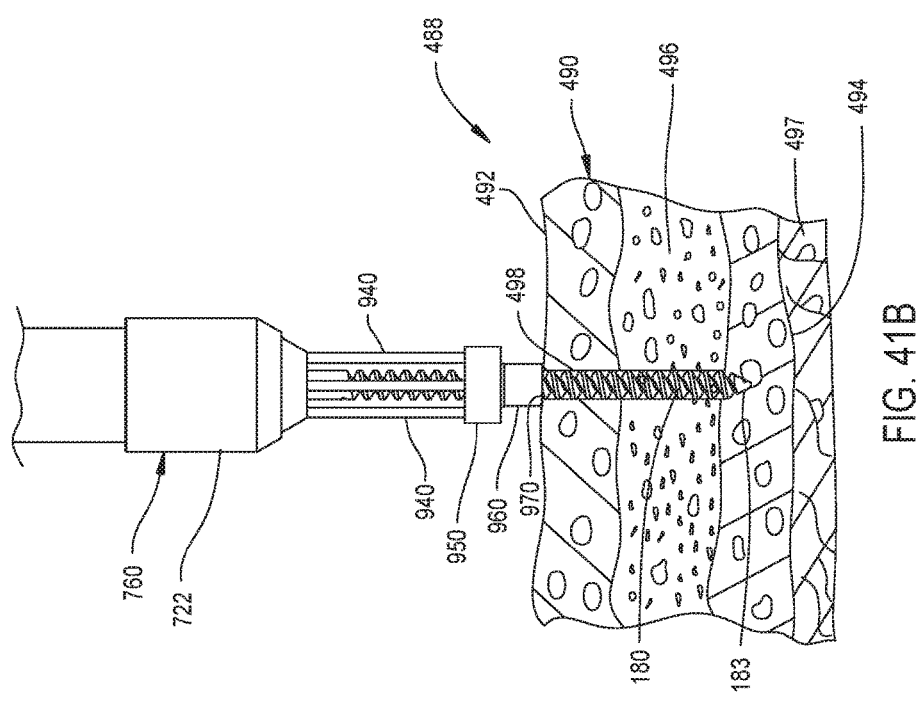
FIG. 41B is a side cross-sectional view of the tissue protector and drill bit of FIG. 26 during formation of a bone bore in a bone.

Referring to FIG. 41B, as the drill bit tip 183 enters the bone, the distal end 970 of the tissue protector abuts against the proximal side 492 of bone 490 limiting the forward movement of tissue protector 950. As the drill bit 180 continues to rotate, the combination of the rotating drill bit and the axial load placed on the drill bit by the medical practitioner overcomes the spring force of coil springs 1012 and 1008 and the interference fit between the inner surface of sleeve 960 and the outer circumference 186 of the drill bit. Handpiece 102 is therefore able to advance towards the tissue protection 950. As the bone bore 498 is formed, the length of the drill bit 180 exposed or extending beyond the distal end 970 of the tissue protector increases. Continued rotation of the drill bit and axial loading causes the drill bit tip 183 to penetrate through the bone and bone marrow 496 and to approach the distal side 494 of bone 490.

At the same time the drill bit 180 is advancing, the outer coupler 750, the inner coupler 730, the hollow motor shaft 130 and the rest of the rotary surgical drill 700 advance with the drill bit. The outer coupler slides over the static rods 940.

Stop 920 thus appears to retract into outer coupler bore 760 and inner coupler bore 736. The abutment of plunger proximal end 924 against rack distal end 983 causes rack 980 to apparently slide within motor shaft lumen 976. (It should be understood that rack is static and the handpiece advances over the rack.) The sliding movement of outer coupler 750 relative to stop 920 causes compression of coil spring 1012. The sliding movement of motor shaft 130 relative to rack 980 causes compression of coil spring 1008. As the handpiece 102 advances, the proximal end 982 of the rack extends through aperture 1044 outwardly away from actuator housing 1024.

With reference to FIG. 41C, eventually, the drill bit tip 183 cuts through the distal side 494 of bone 490 in which the bone bore 498 is being formed. For the reasons set forth above with respect to the earlier described versions of the invention, sensor 464 detects the occurrence of this event as a change in motor current draw. Processor 452, which is executing braking module software 470, compares the received change in current data from sensor 464 to a pre-determined threshold change in current or current drop level stored in sensor parameter threshold values 472.

In response to the received change in current being greater than the threshold change in current level, processor 452 triggers the engagement of braking mechanism 900 by turning on solenoid 252. When solenoid 252 is turned on, the magnetic field generated by solenoid 252 attracts the steel flange 288 (FIG. 39) and overcomes the spring force of coil spring 350, thereby moving flange 288 and the attached plunger 280 upwardly until flange 288 contacts with the surface 254 of solenoid 252. At the same time, the movement of plunger 280 forces gear tooth 304 into engagement with gear teeth 986 (FIG. 29) of rack 980, locking rack 980 to handpiece 102. When gear tooth 304 is engaged with gear teeth 980, handpiece 102 is prevented from further advancement relative to rack 980. By extension, drill bit 180 is likewise prevented from further advancement. This substantially reduces the unintended cutting of tissue 497 adjacent to the distal side 494 of the bone bore 498 by the drill bit.

After the braking mechanism 900 has stopped advancement of the drill bit 180, the length of the drill in the bone bore 498 is equal to the distance between the distal end 970 of the tissue protector and the distal tip 183 of drill bit 180. This length is the approximate length that is required for a bone screw that is to be inserted into the bone bore.

The medical practitioner will pull the drill bit 180 out from the bone bore 498. If the bone bore is deep, the fit between the drill bit and the bone bore can be a particularly tight fit. The medical practitioner can rotate drill bit 180 in a reverse (counterclockwise) direction using reverse trigger switch 117 to disengage drill bit 180 from the bone bore. With the drill bit 180 removed from the bone bore, the medical practitioner can complete the procedure for which the bore was formed.

Before the medical practitioner uses rotary surgical drill 700 to form another bore, braking mechanism 900 is disengaged. In one embodiment, processor 452 turns off solenoid 252 after sensing the depression of reverse trigger switch 117. In another embodiment, processor 452 turns off solenoid 252 after detecting a certain sequence of depression of the trigger switches 116, 117. For example, processor 452 can turn off solenoid 252 after detecting the simultaneous depression of both trigger switches 116 and 117. In an additional embodiment, a separate switch (not shown) can be provided to turn off solenoid 252. After solenoid 252 is turned off, spring 350 biases plunger 280 to move in a downward direction causing disengagement of gear tooth 304 from teeth 986. Rack 980 is now free to slide within lumen 976.

With rack 980 free to move, the compressed coil spring 1008 causes rack 980 to slide in a distal direction within motor shaft 130. At the same time, the compressed coil spring 1012 causes the stop 920 to slide in a distal direction within outer coupler bore 760 forcing tissue protector 950 to be extended over drill bit 180.

V. Rotary Surgical Drill with Telescoping Member that Retracts with the Actuation of the Drill Bit FIGS. 42-46 illustrate an additional embodiment of a rotary surgical drill 1100 that has a brake mechanism 1150. Rotary surgical drill 1100 comprises handpiece 102, brake mechanism 1150, chuck assembly 1200, drill bit 1500, controller 450 and retracting sleeve mechanism 1600. In particular, brake mechanism 1150 comprises chuck assembly 1200, drill bit 1500 and retracting sleeve mechanism 1600. The rotary surgical drill 1100 has the same handpiece 102 and controller 450 as rotary surgical drill 100 of FIG. 1. In the discussion of rotary surgical drill 1100, components that are common to rotary surgical drill 100 will be referred to using the same reference numbers.

A. Chuck Assembly

Figure 42:
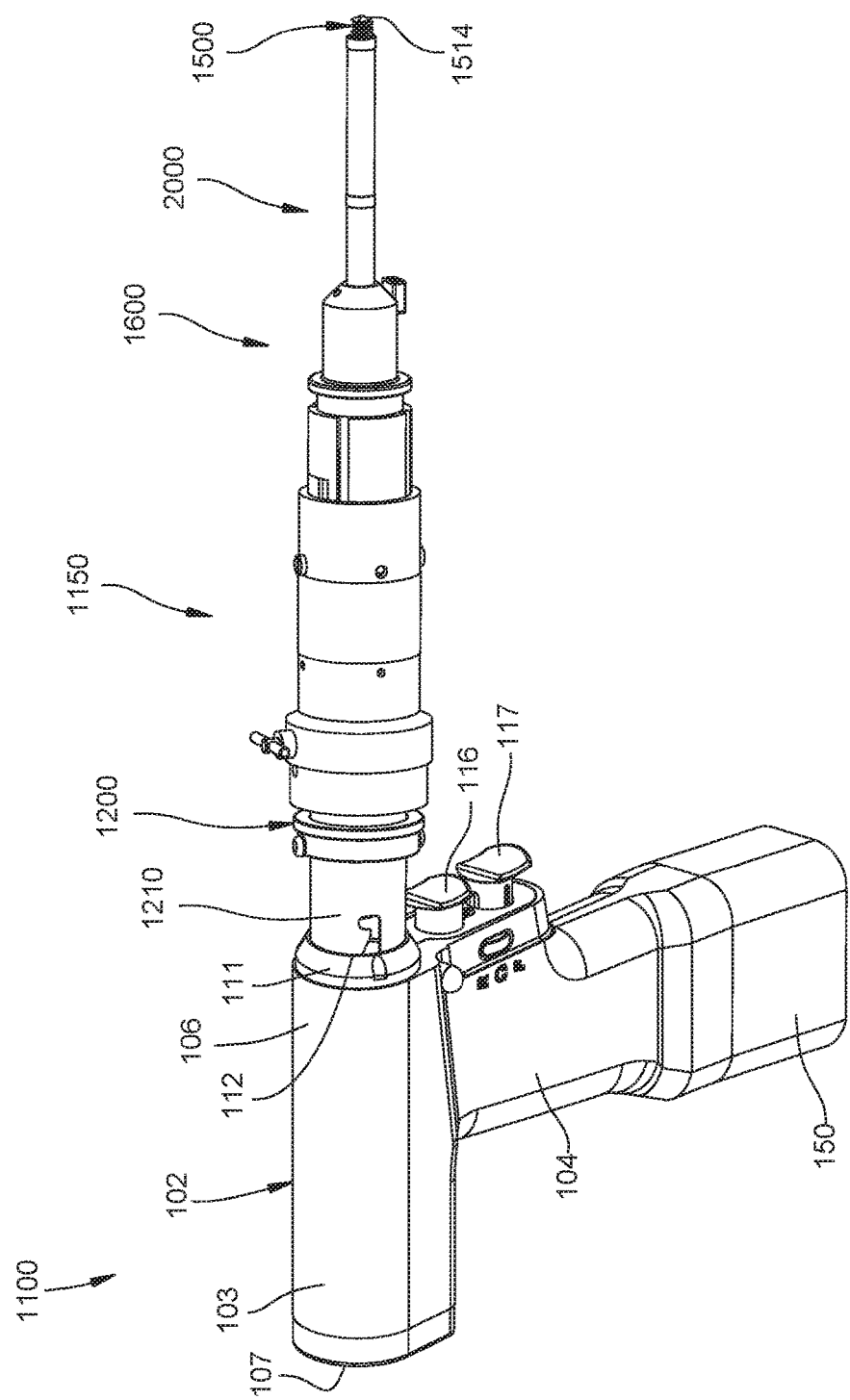
FIG. 42 is an overall perspective view of an additional embodiment of a powered rotary surgical drill having a brake mechanism with a retracting sleeve mechanism in accordance with the present invention.
Figure 47:
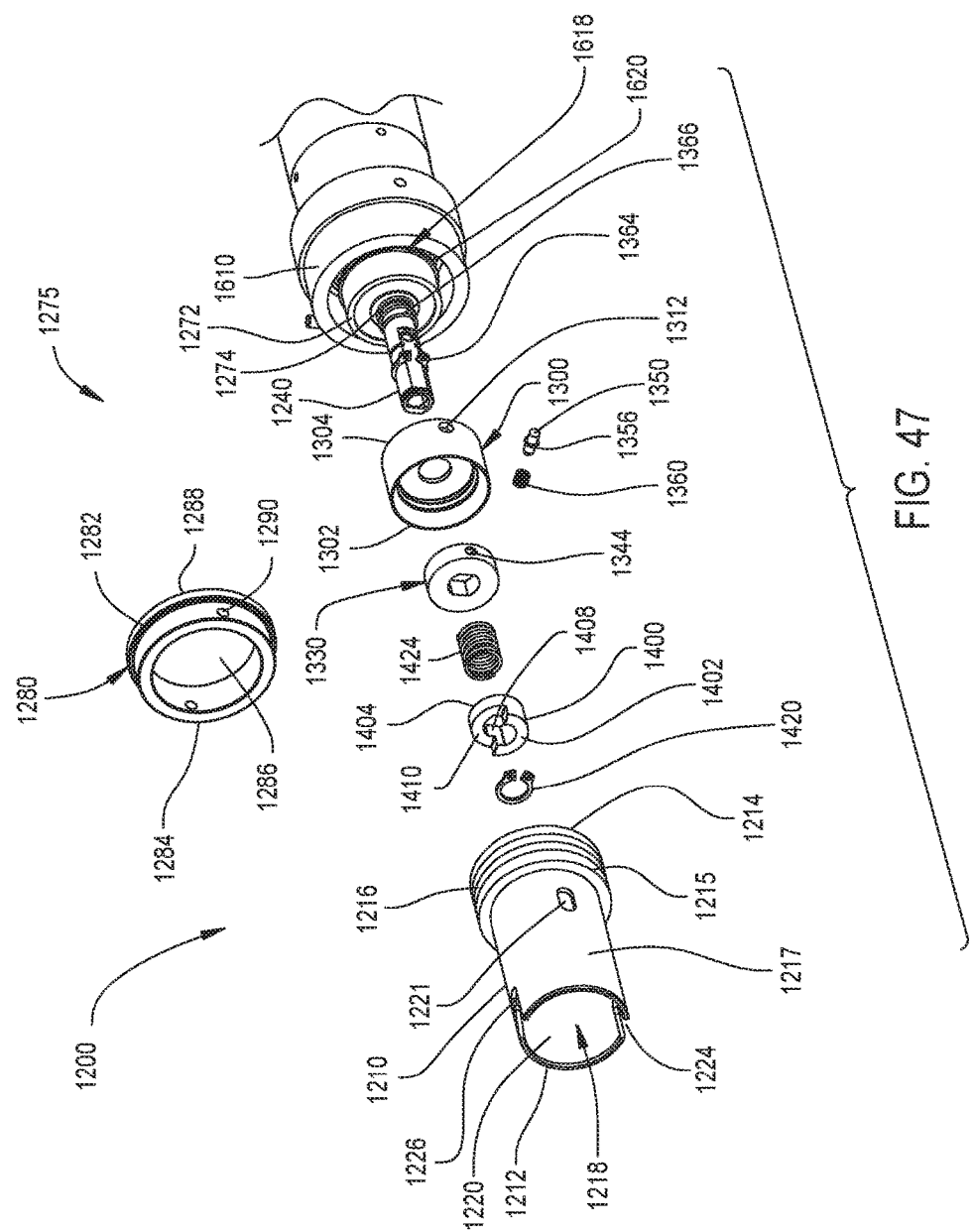
FIG. 47 is a exploded rear perspective view of the components of the chuck assembly and the drill bit retainer assembly.
Figure 51:
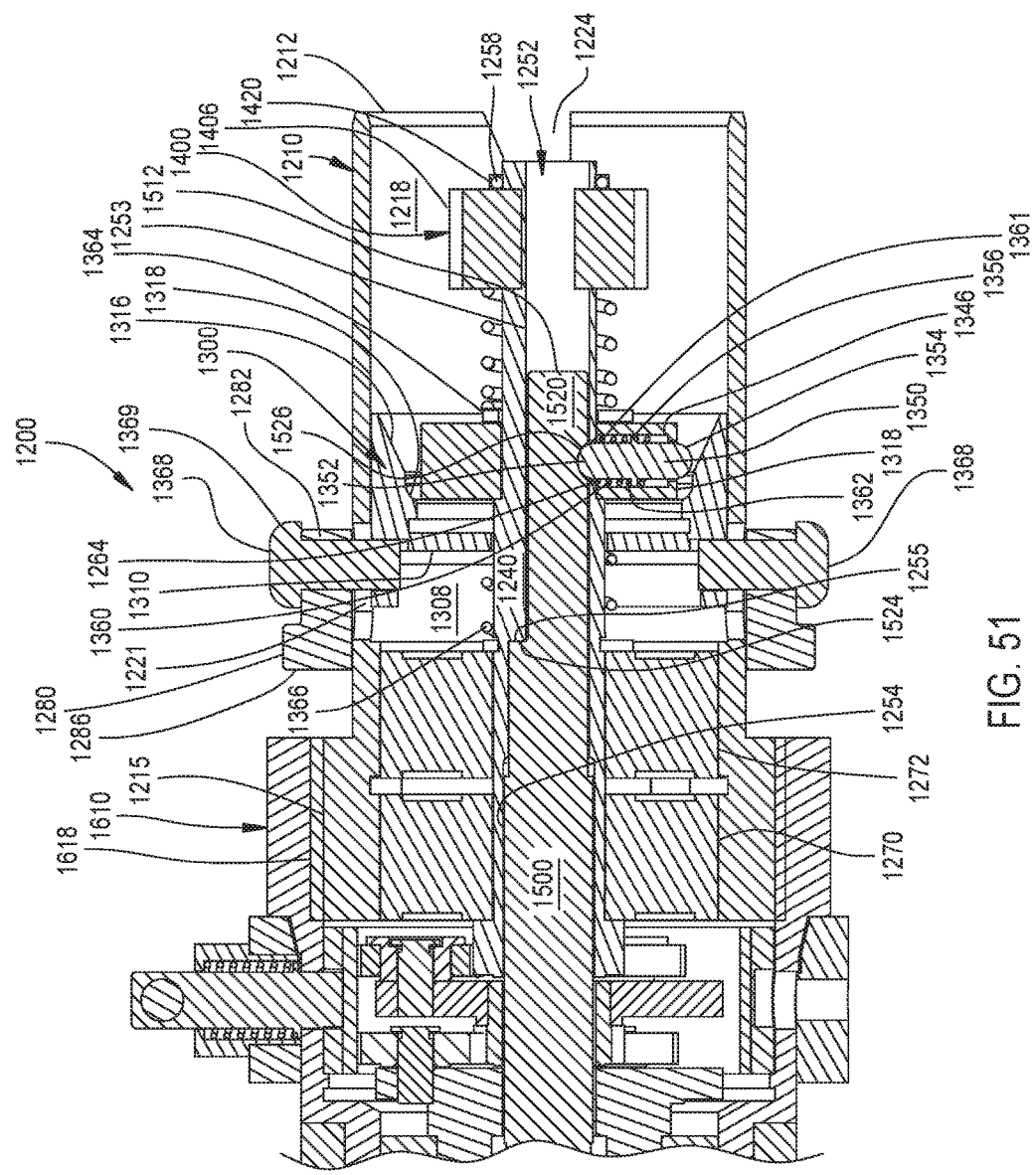
FIG. 51 is an enlarged cross-sectional view of the chuck assembly and the drill bit retainer assembly illustrating the relative orientation of the components.

With reference to FIGS. 42, 47 and 51, chuck assembly 1200 is shown mounted to handpiece 102. Chuck assembly 1200 is removably attachable to handpiece 102. The chuck assembly 1200 includes an end cap 1210 that is cylindrical in shape and has a proximal end 1212 and a distal end 1214. A flange 1215 extends circumferentially around distal end 1214. External threads 1216 are defined in the outer annular surface of flange 1215. End cap 1210 is formed from a single piece of metal. The end cap 1210 is mounted within the bore 1618 of connecting hub 1610 (FIG. 47) by the mating of external threads 1216 with internal threads 1620 in hub 1610.

End cap 1210 has an outer annular surface 1217. A bore 1218 extends through end cap 1210 and defines an inner annular surface 1220. A pair of diametrically opposed slots 1221 are defined thru opposite sides of end cap 1210 slightly spaced from the proximal wall of flange 1215. An arcuate V-shaped cutout 1224 is located in end cap 1210 and extends from proximal end 1212 towards distal end 1214 and terminates in an arcuate slot 1226. Cutout 1224 is contiguous with slot 1226.

Handpiece 102 has a pin (not shown) that extends downwardly from the top of case 103 into handpiece opening 112. Chuck assembly 1200 is attached to handpiece 102 (FIG. 42) by inserting the end cap proximal end 1212 into handpiece opening 112 with the pin aligned with the V-shaped cutout 1224. As end cap 1210 is moved in a proximal direction into opening 112, the pin will contact the base of slot 1226. End cap 1210 and the entire brake mechanism 1150 are then rotated counter clockwise causing the pin to be captured in slot 1226. The pin and slot 1226 are dimensioned such that the pin and slot 1226 form a snug interference fit. The end cap 1210 and brake mechanism 1150 are now affixed to handpiece 102.

Chuck assembly 1200 includes an input drive shaft 1240. Input drive shaft 1240 is illustrated with reference to FIGS. 47, 48 and 51. Input drive shaft 1240 is formed from a single piece of metal. Input drive shaft 1240 is generally cylindrical in shape. The input drive shaft 1240 has a center section 1241, a proximal end 1242 and a distal end 1244. Input drive shaft 1240 includes a head 1246 located at distal end 1244. Shaft head 1246 is formed with radially outwardly extending gear teeth 1248. Input drive shaft 1240 also has an outer surface 1250 and a proximal bore 1252 (FIG. 51) that extends thru the proximal end of input drive shaft 1240. The proximal bore 1252 is D-shaped such that one side 1253 (FIG. 51) of the inner surface of bore 1252 is flat. A counter bore 1254 is defined in head 1246 and extends from distal end 1244 in a proximal direction terminating at step 1255. Counter bore 1254 defines an inner surface 1255. Bore 1252 and counter bore 1254 are co-axial and contiguous.

Two annular grooves 1256 and 1257 are defined in outer surface 1250 and within center section 1251. Another annular groove 1258 is defined in outer surface 1250 slightly spaced from proximal end 1242. A pair of flat faces 1260 is defined on opposite sides of outer surface 1250. Flat faces 1260 extend from groove 1258 to slightly beyond a hole 1262. Hole 1262 extends perpendicularly thru one of the flat faces 1260 into bore 1252. A tapered conical seat 1264 surrounds hole 1262 and faces outwardly.

Bearings 1270 and 1272, both identified in FIG. 51, are press fit into the distal end of the end cap bore 1218. Bearings 1270 and 1272 are seated in bore 1218 with the outer surface of the bearings surrounded by inner annular surface 1212. Bearings 1270 and 1272 each have a central aperture that the drive shaft 1240 is extends through. Bearings 1270 and 1272 support drive shaft 1240 for rotary motion within end cap 1210 and hub 1610. Bearings 1270 and 1272 are retained between the proximal face of head 1246 and a retaining ring 1274 that is affixed in groove 1256.

Turning specifically to FIG. 47, the chuck assembly 1200 includes a drill bit retainer assembly 1275. Drill bit retainer assembly 1275 includes an outer release collar 1280, an inner release collar 1300 and a pin holder 1330. The outer release collar 1280 is generally cylindrical in shape and has a proximal face 1282, a distal face 1284 and a central passage 1286. An annular circumferential lip 1288 surrounds the distal face 1284. A pair of diametrically opposed through holes 1290 are defined thru outer release collar 1280 slightly spaced from lip 1288.

Figure 49:
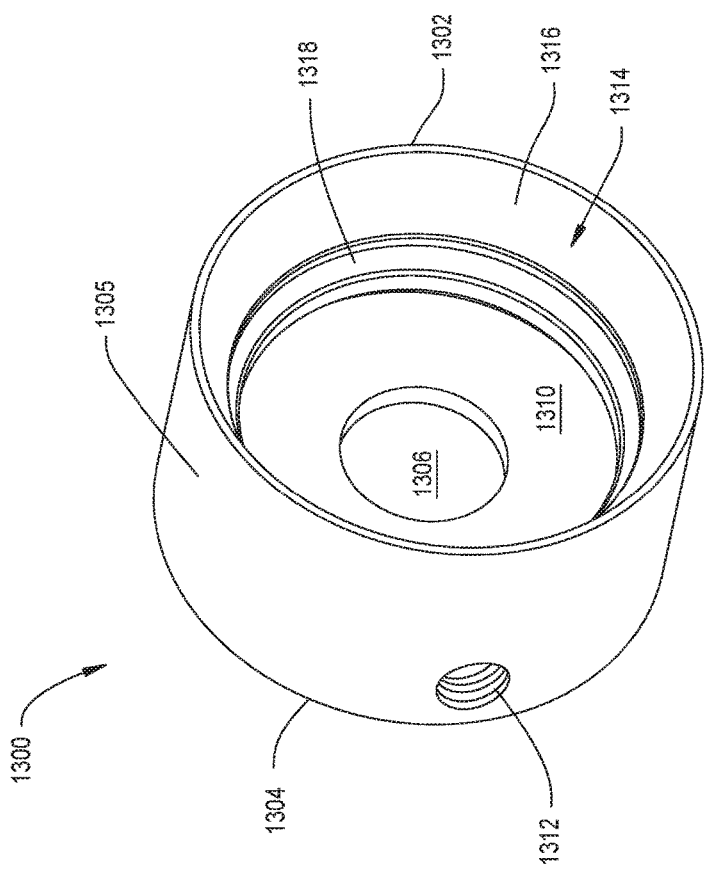
FIG. 49 is a rear perspective view of the inner release collar.

With additional reference to FIG. 49, details of the inner release collar 1300 is now described. The inner release collar 1300 is generally cylindrical in shape and has a proximal end 1302, a distal end 1304, an outer annular surface 1305 and a central passage 1306. A distal facing recess 1308 (FIG. 51) is defined in distal end 1304. The distal facing recess 1308 terminates at the distal face of a wall 1310. A pair of diametrically opposed internally threaded apertures 1312 are defined thru inner release collar 1300 between distal end wall 1304 and wall 1310. A proximal facing recess 1314 is defined in proximal end 1302. The proximal facing recess 1314 terminates at the proximal face of wall 1310. Recess 1314 is defined by an annular ramp 1316 that extends distally forward from the proximal end of collar 1300 1314. Extending distally, ramp angles inwardly toward dividing wall 1310 terminating at detent 1318.

Figure 50:
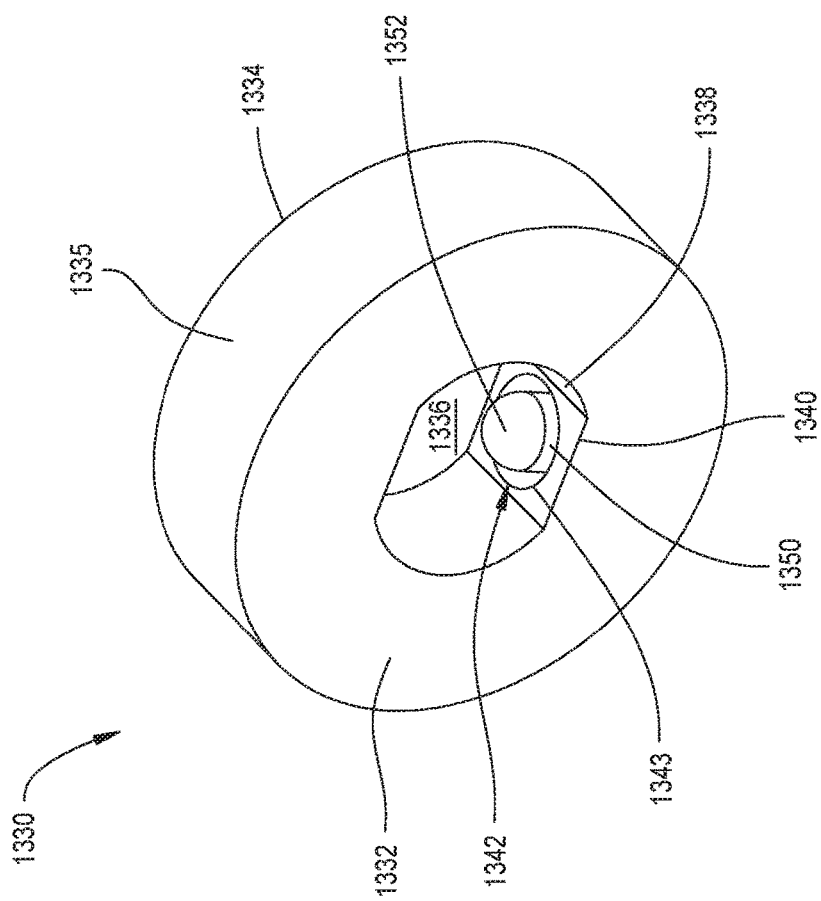
FIG. 50 is a rear perspective view of the plunger and the pin holder.

Referring to FIGS. 50 and 51, pin holder 1330 is shown. The pin holder 1330 is generally cylindrical in shape and has a proximal face 1332, a distal face 1334, an outer circumferential surface 1335 and a central passage 1336. The central passage 1336 is defined by a pair of diametrically opposed arcuate walls 1338 and by a pair of diametrically opposed flat walls 1340 that all face into passage 1336. A bore 1342 is defined thru pin holder 1330 between outer surface 1335 and one of the flat walls 1340. Bore 1342 has an interior opening 1343 adjacent flat wall 1340 and an exterior opening 1344 adjacent outer surface 1335. An annular shoulder 1346 is defined within bore 1342.

A pin 1350 and coil spring 1360 are mounted in pin holder 1330. Specifically, pin 1350 is cylindrical in shape with a rounded inner end 1352 and a rounded outer end 1354. An annular flange 1356 (FIG. 47) surrounds the central portion of pin 1350. The coil spring 1360 is mounted around the inner end 1352 of pin 1350. Coil spring 1360 has ends 1361 and 1362.

Pin 1350 is mounted in bore 1342 with the outer end 1354 extending through exterior opening 1344 and the inner end 1352 extending through interior opening 1343. Coil spring 1360 is positioned in bore 1343 with end 1361 seated against the conical seat 1264 of input drive shaft 1240 and end 1362 seated against flange 1356. Coil spring 1360 biases pin 1350 away from input drive shaft 1240.

Pin holder 1330 is received in the proximal facing inner release collar recess 1314 with the distal face 1334 abutting the proximal face of dividing wall 1310. The pin holder passage 1336 is mounted over drive shaft 1240. Pin holder 1330 is slid over drive shaft proximal end 1242 such that the drive shaft flat faces 1260 are juxtaposed to the pin holder flat walls 1340. Pin holder 1330 is retained in recess 1314 and held to input drive shaft 1240 by a retaining ring 1364. Ring 1364 is seated in drive shaft groove 1257.

With reference to FIGS. 47 and 51, the inner release collar 1300 is disposed for sliding movement within bore 1218 of end cap 1210. Outer release collar 1280 is disposed for sliding movement around the outer surface 1217 of end cap 1210. A coil spring 1366 is mounted over drive shaft 1240 around center section 1241. Coil spring 1366 has a proximal end that abuts the distal face of dividing wall 1310 and a distal end that abuts the retaining ring 1274. Coil spring 1366 biases the inner release collar 1300 in a proximal direction away from bearing 1272.

The threaded screws 1368 have a head 1369 that abuts the outer surface of outer release collar 1280. Screws 1368 extend through holes 1290, through slots 1221 of end cap 1210 and are received in threaded apertures 1312 of inner release collar 1300. Screws 1368 connect the outer release collar 1280 to the inner release collar 1300 such that movement of outer release collar 1280 results in a like movement of inner release collar 1300. The combination of the outer 1280 and inner 1300 release collars can slide longitudinally in end cap 1210. The movement of outer 1280 and inner 1300 release collars is limited by the abutment of screws 1369 with the ends of slots 1221. The outer 1280 and inner 1300 release collars are biased in a proximal direction by coil spring 1366 such that screws 1369 normally abut the proximal ends of slots 1221. In this static position, the outer end 1354 of pin 1350 abuts against and slightly into detent 1318.

Figure 52:
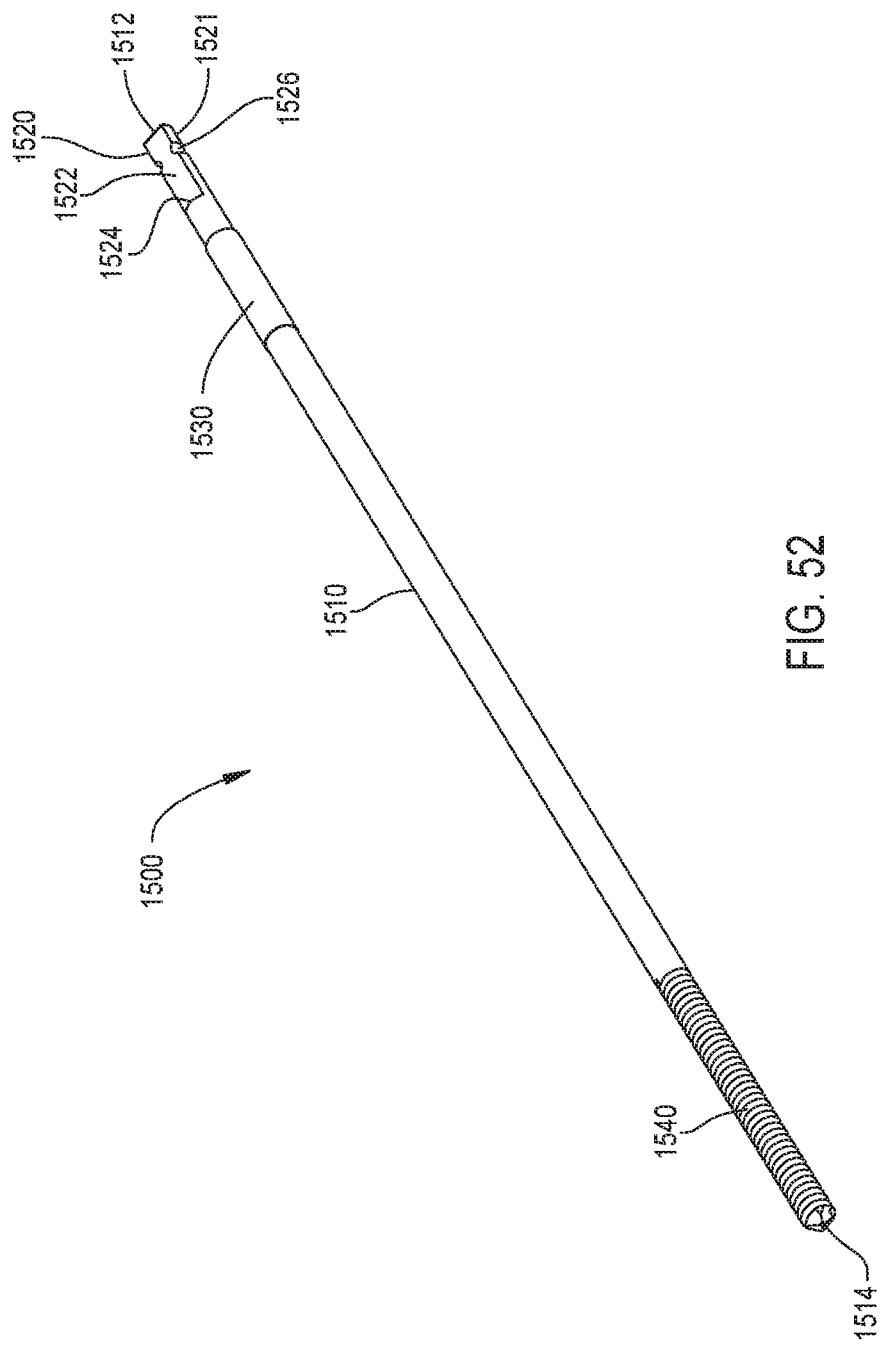
FIG. 52 is a front perspective view of the drill bit.

Turning to FIG. 52, the drill bit 1500 is shown. Drill bit 1500 has an elongated rod shape with a center shaft or section 1510, a proximal end 1512 and a distal pointed cutting tip 1514. A drive head 1520 is defined at proximal end 1512. Drive head 1520 has a D-shaped cross-section with an arcuate surface 1521 and a flat surface 1522. Flat surface 1522 extends from the proximal end 1512 in a distal direction and terminates at a step 1524. An annular raised portion 1530 is spaced from step 1524. A pair of diametrically opposed grooves 1526 are defined in the arcuate surfaces 1521.

The drill bit 1500 is retained in chuck assembly 1200 by drill bit retainer assembly 1275. Referring to FIG. 51, the drive head 1520 is received within input drive shaft D-shaped bore 1252 and bore 1254. The drill bit 1500 can move in a proximal direction relative to input drive shaft 1240 until drill bit step 1524 abuts the input drive shaft step 1255. The flat surface 1522 abuts a flat interior surface within bore 1252. As the drill bit 1500 seats into D-shaped bore 1252, coil spring 1360 biases pin end 1352 to move through hole 1262 and into engagement with groove 1526. In this position, the drill bit 1500 is clamped within chuck assembly 1200 by pin 1350.

Drill bit 1500 is removed from chuck assembly 1200 by releasing drill bit retainer assembly 1275. A medical practitioner grasps the outer release collar 1280 and moves the outer release collar in a distal direction causing compression of coil spring 1366. The movement of the outer release collar 1280 in the distal direction is limited by the abutment of screws 1369 with the distal end of slots 1221. Distal movement of the outer release collar 1280 causes a like movement of the inner release collar. More particularly the inner release collar is displaced so that the portion of the collar that defines detent 1318 moves forward of pin 1350. Spring 1360 forces pin 1350 outwardly from bore 1342 and pin outer end 1354 tracks or slides along ramp 1316. As the pin outer end 1354 reaches the proximal end of ramp 1316, the inner end 1352 of the pin withdraws from drill bit groove 1526. This allows the drill bit 1500 to be removed from inner drive shaft 1240 and chuck assembly 1200.

Referring to FIGS. 47 and 51, driving collar 1400 is now described. The driving collar 1400 is generally cylindrical in shape and has a proximal face 1402 and a distal face 1404. Driving collar 1400 has an outer annular surface 1406 and a bore 1408 with two flat sides and two arcuate sides. A cutout 1410 is located in proximal face 1402 and extends from the outer annular surface 1406 to the center of bore 1408 and from proximal face 1402 approximately half the length of collar 1400.

Driving collar 1400 is mounted over input drive shaft proximal end 1242 such that the input drive shaft extends through bore 1408. The input drive shaft flat sides 1260 (FIG. 48) are adjacent the flat sides of bore 1408 and the input drive shaft arcuate sections are adjacent the arcuate sides of bore 1408.

A retaining ring 1420 is affixed in input drive shaft groove 1258. The retaining ring 1420 holds the driving collar 1400 on input drive shaft 1240. A coil spring 1424 is mounted over input drive shaft 1240 between retaining ring 1364 and the distal face 1404 of driving collar 1400. Spring 1424 biases driving collar 1400 in a proximal direction away from pin holder 1330. When chuck assembly 1200 is attached to handpiece 102, the driving collar 1400 engages motor shaft 130 (FIG. 3) such that the rotation of the motor shaft 130 rotates driving collar 1400 causing a like rotation of input drive shaft 1240 and drill bit 1500.

B. Retracting Sleeve Mechanism

Figure 48:
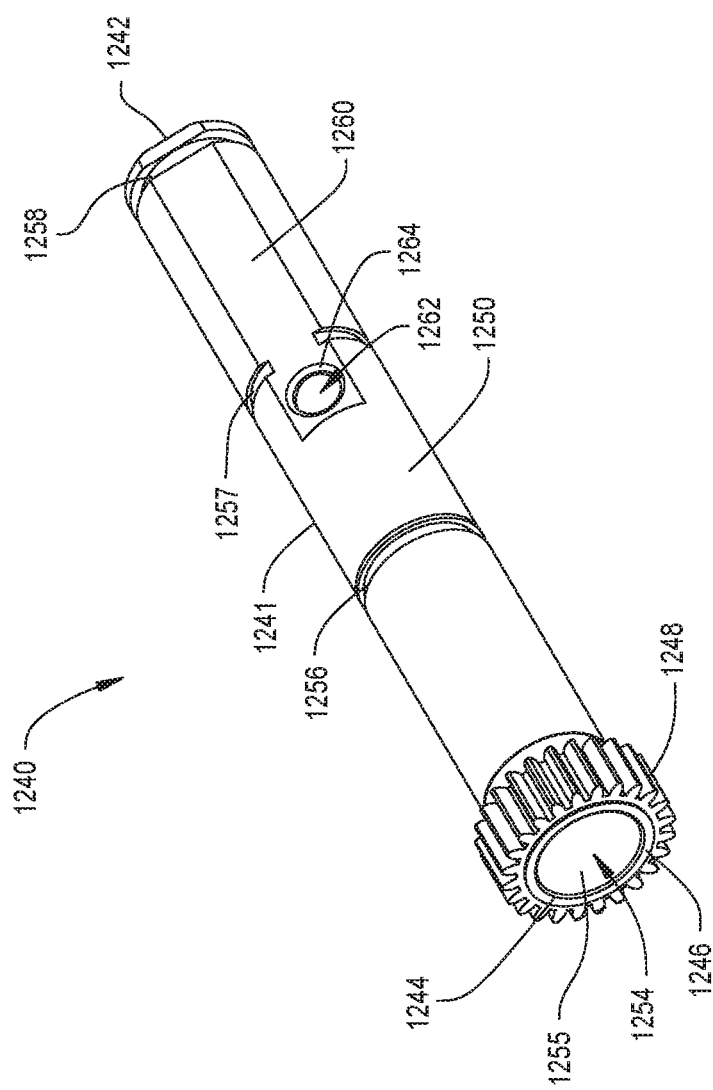
FIG. 48 is a front perspective view of the input drive shaft.

With reference to FIGS. 42, 48 and 51, the retracting sleeve mechanism 1600 will now be described and illustrated. Retracting sleeve mechanism 1600 is coupled to chuck assembly 1200. The retracting sleeve mechanism 1600 comprises a connecting hub 1610, a planetary gear assembly 1700, an output drive shaft 1800, a ball nut 1850, a coupler 1900, a tissue protector sleeve 2000, a first release mechanism 1750 and a second release mechanism 2100.

Figure 53A:
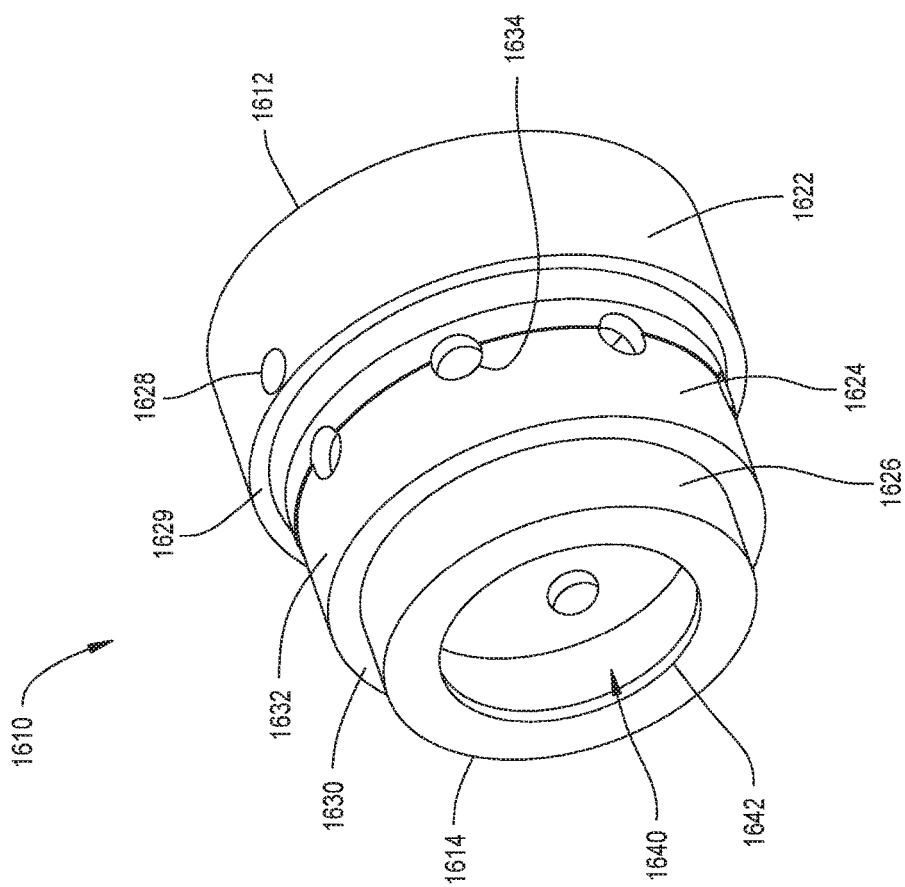
FIG. 53A is a front perspective view of the connecting hub.
Figure 53B:
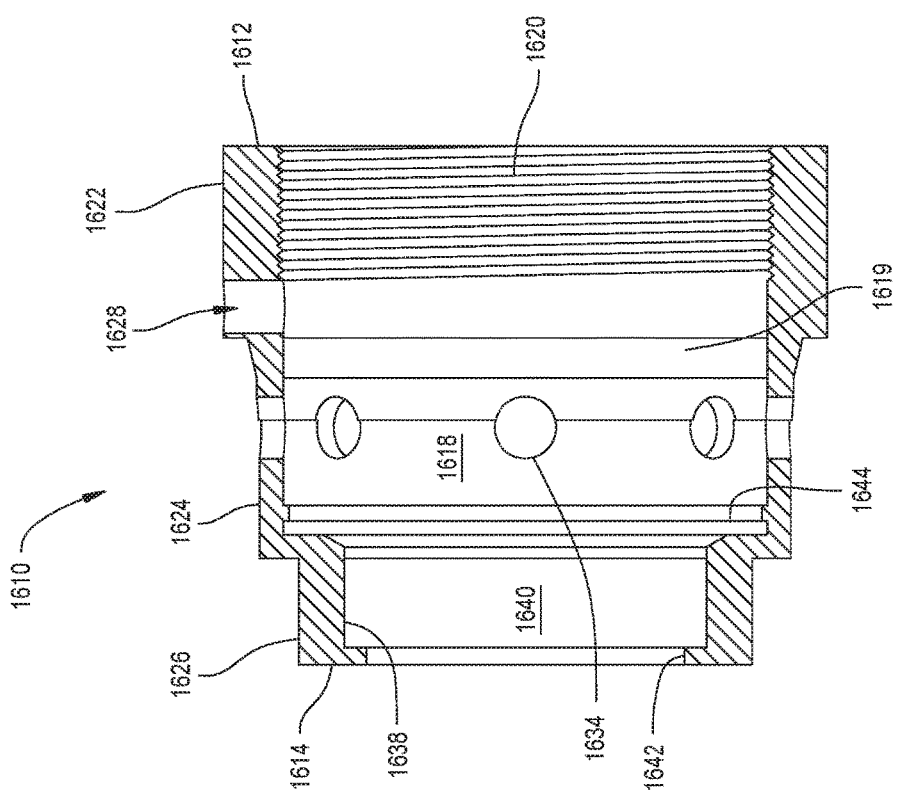
FIG. 53B is a side cross-sectional view of the connecting hub.

Referring to FIGS. 53A and 53B, connecting hub 1610 is illustrated. The connecting hub 1610 is generally cylindrical in shape and can be formed from a single piece of metal. Connecting hub 1610 has a distal end 1612 and a proximal end 1614. Connecting hub 1610 further has a base section 1622, a center section 1624 and an end section 1626. Center section 1624 has a smaller diameter than base section 1622 and end section 1626 has a smaller diameter than center section 1624. An inner annular surface 1619 is located within base section 1622 and center section 1624. Inner annular surface 1619 defines a bore 1618. Internal threads 1620 are defined on the annular surface 1619 of base section 1622. End cap 1210 (FIG. 47) is attached to connecting hub 1610 by the mating of external threads 1216 (FIG. 47) with the internal threads 1620 in hub 1610. Base section 1622 also has an aperture 1628 that extends perpendicularly through base section 1622 into bore 1618. A distal facing step 1629 is defined at the intersection of center section 1624 with base section 1622. Another distal facing step 1630 is defined at the intersection of end section 1626 with center section 1624.

Center section 1624 has an outer annular surface 1632. Eight equally spaced holes 1634 are formed through center section 1624 extending from outer surface 1632 into bore 1618. An inner annular surface 1638 is located within end section 1626 and defines a bore 1640. Bore 1640 is coaxial and contiguous with bore 1618. An annular lip 1642 protrudes from distal end 1614 into bore 1640. A proximal facing step 1644 is defined in center section 1624 at the terminal end of bore 1618.

Turning to FIG. 54, a release ring 1650 is shown. The release ring 1650 has an annular shape with a proximal end 1651, a distal end 1652, an outer surface 1654 and an inner surface 1656. An opening 1658 thru release ring 1650 is defined by inner surface 1656. An upper threaded aperture 1660 and a diametrically opposed lower threaded aperture 1662 extend perpendicularly thru opposite sides of release ring 1650. Release ring 1650 can be formed from a single piece of metal.

With additional reference to FIGS. 53A and 53B, the release ring 1650 is mounted over center section 1624 of connecting hub 1610 with the ring interior surface 1656 surrounding the hub outer surface 1632. A set screw 1664 is mounted through threaded aperture 1662 and is tightened into engagement with outer surface 1632 in order to retain release ring 1650 to connecting hub 1610.

Figure 46:
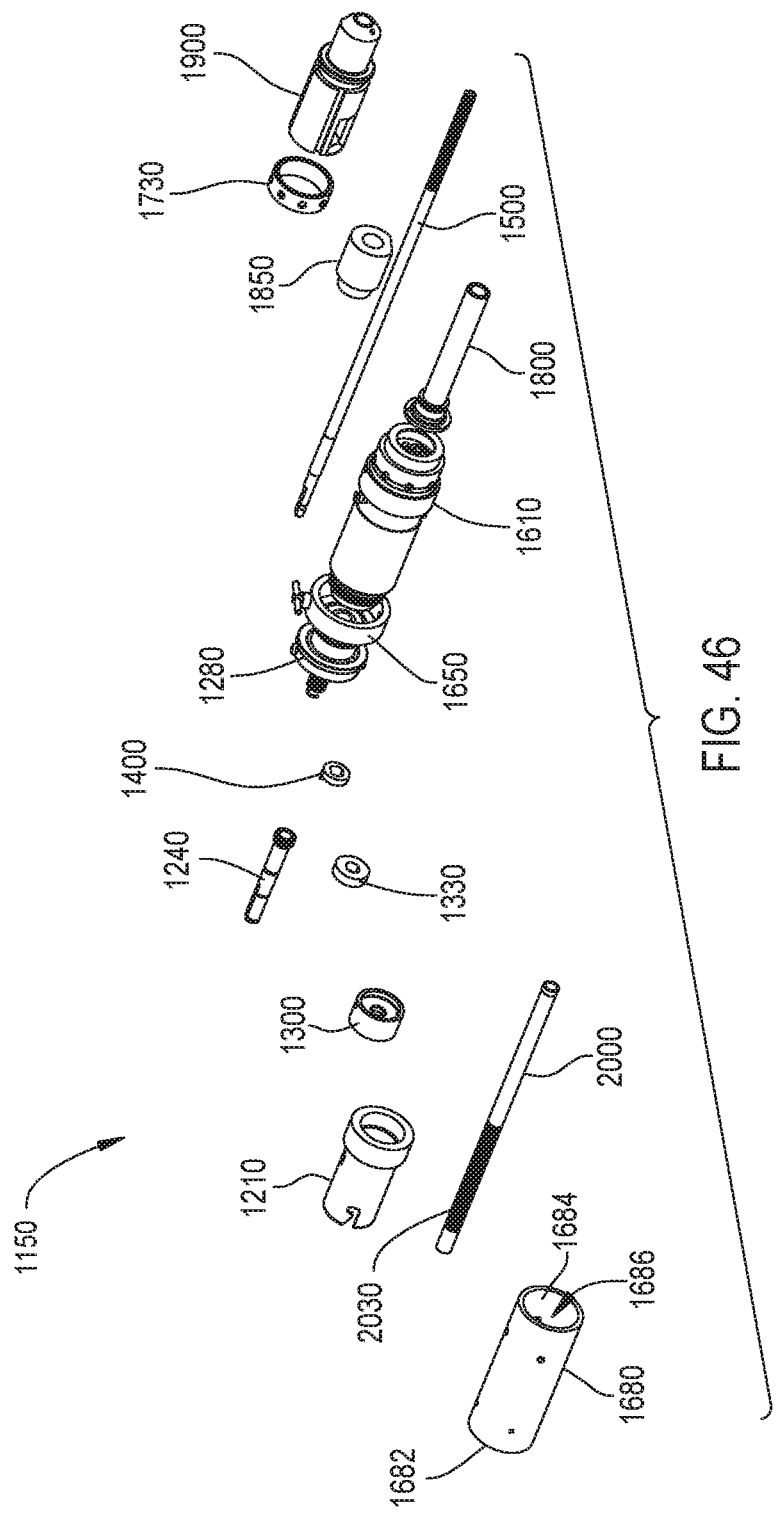
FIG. 46 is an exploded view of the brake mechanism of FIG. 43.

The housing 1680 is illustrated with reference to FIGS. 43 and 46. Housing 1680 is generally cylindrical in shape and can be formed from a single piece of metal. Housing 1680 includes a distal end 1682 and a proximal end 1684. Housing 1680 has an inner annular surface 1684 that defines a through bore 1686. The end section 1626 of connecting hub 1610 (FIG. 53A) is press fit into the proximal end of bore 1686 such that the proximal end 1682 of the housing abuts distal facing step 1630. End cap 1210, connecting hub 1610 and housing 1680 are all connected together to form a unitary piece.

Figure 55:
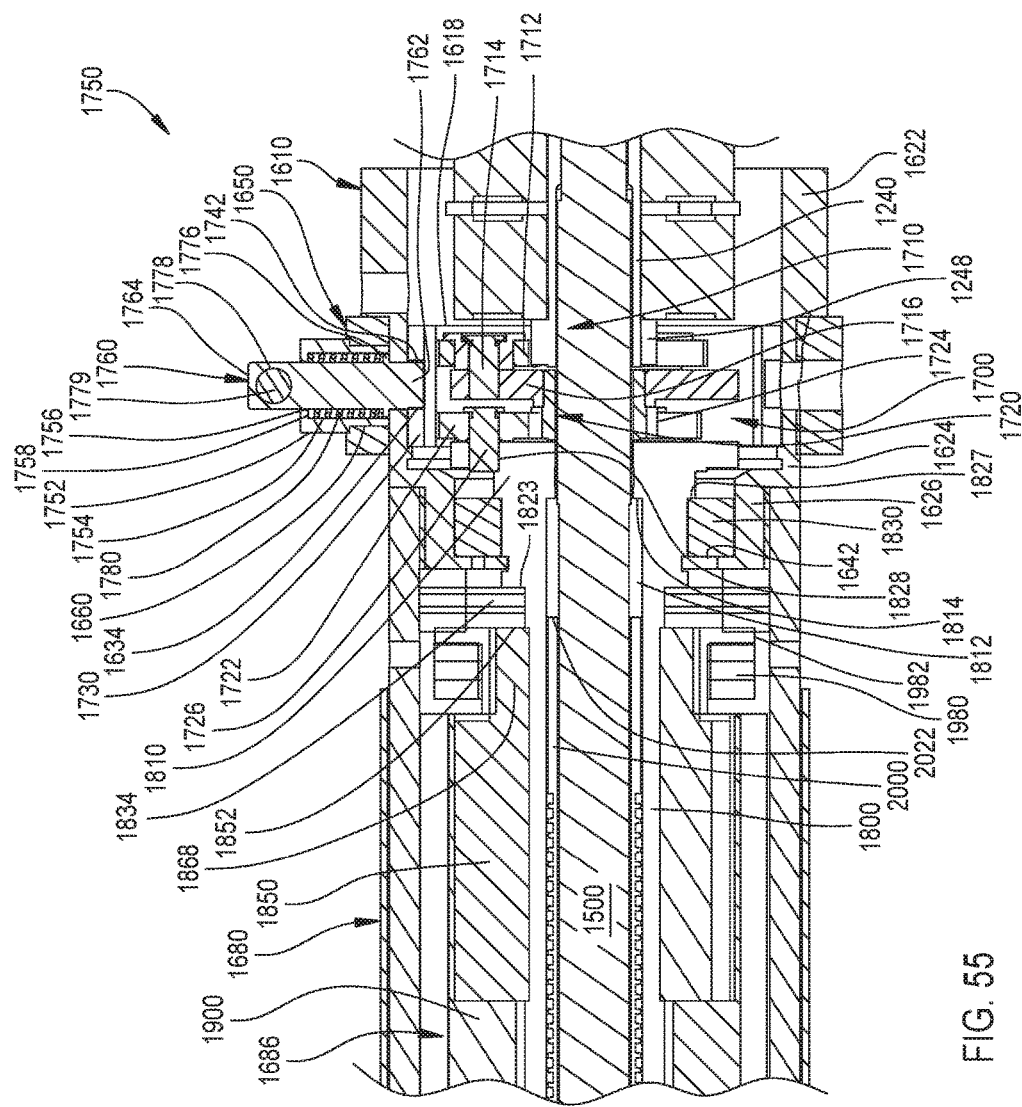
FIG. 55 is an enlarged side cross-sectional view of the first release mechanism, the planetary gear assembly and the proximal portion of the retracting sleeve mechanism illustrating the relative orientation of the components.

From FIG. 55 it can be seen that retracting sleeve mechanism 1600 includes a planetary gear assembly 1700. Planetary gear assembly 1700 is mounted within bore 1618 of connecting hub 1610. The planetary gear assembly 1700 is a two stage planetary gear assembly that includes a first stage 1710 and a second stage 1720. The first stage 1710 has three planet gears 1712. Planet gears 1712 engage the gear teeth 1248 of input drive shaft 1240. The first stage planet gears 1712 drive ring gear 1730. Planet gears 1712 rotate about pins 1714 that are mounted to a disc 1716. Ring gear 1730 drives the second stage 1720 of three planet gears 1722 and a sun gear 1724 connected to disc 1716. The second stage planet gears 1722 rotate about pins 1726 that are mounted to the head 1810 of output drive shaft 1800. The second stage planet gears 1722 drive output drive shaft 1800. The planetary gear assembly 1700 causes a speed reduction in the rotational rate (RPM) of output drive shaft 1800 as compared to the rotational rate of motor shaft 130.

Figure 56:
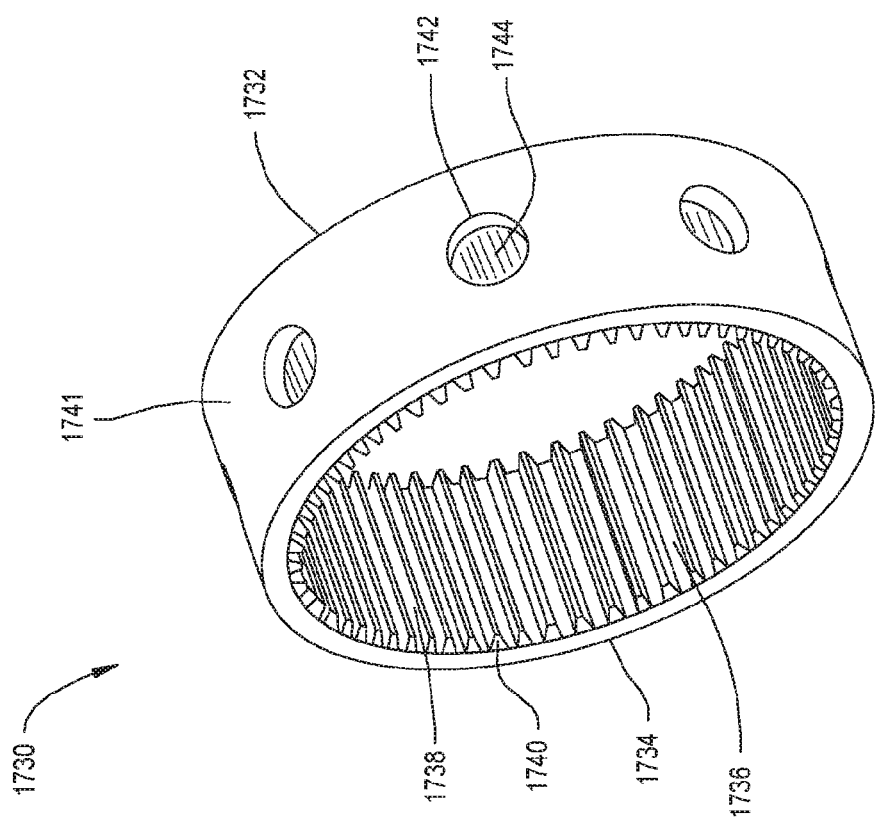
FIG. 56 is a front perspective view of the ring gear.

Turning to FIG. 56, ring gear 1730 is shown. The ring gear 1730 has an annular shape with a proximal side 1732 and a distal side 1734. A central opening 1736 is defined thru ring gear 1730. Ring gear 1730 further has an inner annular surface 1738 upon which teeth 1740 are formed and an outer annular surface 1741. Ring gear teeth 1740 engage teeth of planet gears 1712 and 1722. Eight shallow bores 1742 are equally spaced around the outer circumference of the outer annular surface 1741. The bores 1742 extend partially into ring gear 1730 and terminate at a terminal wall 1744 within each bore. The ring gear 1730 is positioned in connecting hub center section 1624 (FIG. 53B) with the outer surface 1741 adjacent and surrounded by the connecting hub inner surface 1619. Ring gear 1730 can rotate within bore 1618.

Rotary motion is transferred from input drive shaft 1240 through the first stage 1710 planetary gears and the second stage planetary gears to drive output drive shaft 1800. Planetary gear assembly 1700 produces a speed reduction ratio of generally between 10 to 1 and 20 to 1. More often the speed reduction is between 13 to 1 and 16 to 1.

Figure 43:
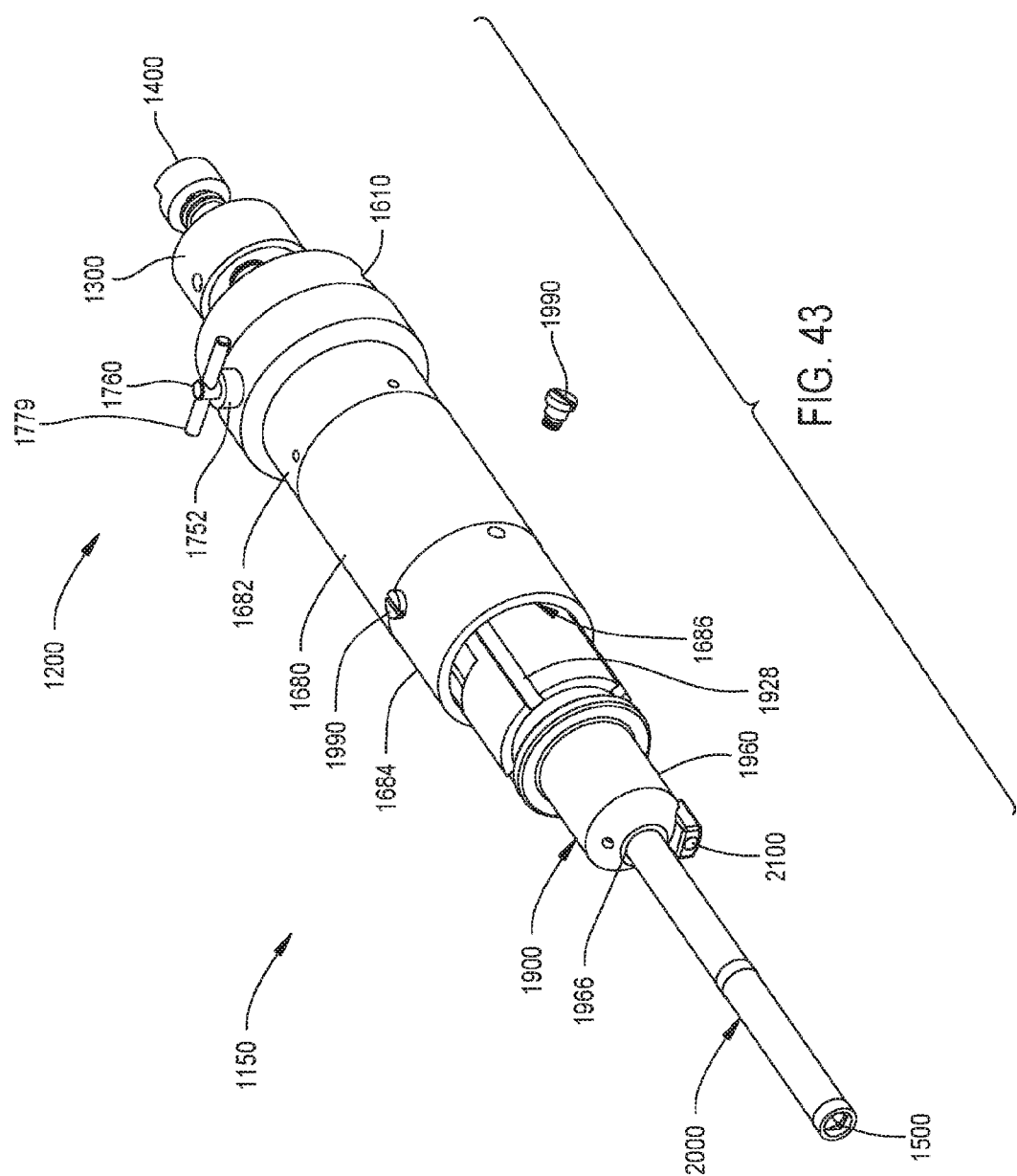
FIG. 43 is a front perspective view of the brake mechanism of FIG. 26 including the chuck assembly and the retracting sleeve mechanism.

Retracting sleeve mechanism 1600 includes a first release mechanism 1750 seen in FIGS. 43 and 55. The first release mechanism 1750 is mounted to release ring 1650. The first release mechanism 1750 includes a barrel 1752 that is screwed into threaded aperture 1660 (FIG. 54). Threads (not shown) are defined on the lower exterior surface of barrel 1752. Barrel 1752 has a hollow cylindrical shaped interior cavity 1754 with an upper opening 1756 and a circumferential rim 1758 that protrudes into opening 1756.

A piston 1760 and coil spring 1780 are mounted in cavity 1754. Specifically, piston 1760 is cylindrical in shape with an inner end 1762 and an outer end 1764. An annular flange 1776 surrounds a lower portion of the piston 1760 and is spaced from inner end 1762. A hole 1778 extends through an upper portion of the post 1760. A handle 1779 is mounted through hole 1778 and affixed to piston 1760. The coil spring 1780 is mounted around the piston 1760. The coil spring 1760 has an upper end that abuts rim 1758 and a lower end that abuts flange 1776.

The coil spring 1780 biases the piston inner end 1762 through one of connecting hub holes 1634 and into one of release ring bores 1742 when one of the hub holes 1634 is in coaxial alignment with one of the release ring bores. The piston inner end 1762 is normally seated against terminal wall 1744 (FIG. 56). In this position, piston 1760 prevents the rotation of ring gear 1730 relative to connecting hub 1610 such that the rotation of input drive shaft 1240 results in the like rotation of output drive shaft 1800.

A user pulls upwardly on handle 1779 resulting in the compression of coil spring 1760 and the piston inner end 1762 being removed from the release ring bore 1742. In this position, ring gear 1730 is free to rotate relative to connecting hub 1610 such that the rotation of input drive shaft 1240 only results in the rotation of ring gear 1730. Output drive shaft 1800 is therefore disconnected from input drive shaft 1240. The first release mechanism 1750 allows a medical practitioner to connect and disconnect output drive shaft 1800 from input drive shaft 1240 so as to move coupler 1900 as will be described later.

Figure 57A:
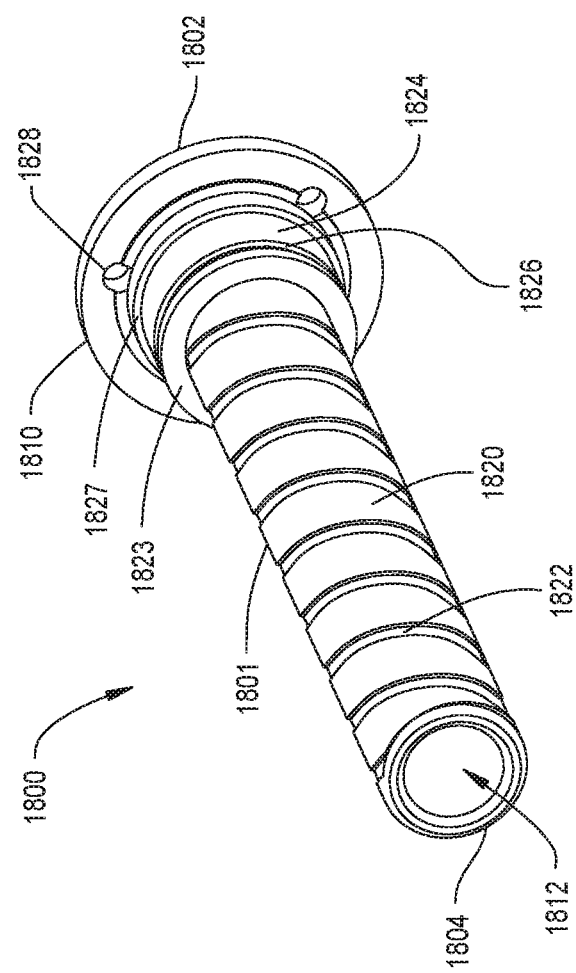
FIG. 57A is a front perspective view of the output drive shaft.

Output drive shaft 1800 is described with reference to FIGS. 55, 57A and 57B. The output drive shaft 1800 is formed from a single piece of metal. Output drive shaft 1800 is generally cylindrical in shape. The output drive shaft 1800 has a center shaft 1801, a proximal end 1802 and a distal end 1804. A disk shaped head 1810 is formed at proximal end 1802. A bore 1812 extends from distal end 1804 in a proximal direction into the output drive shaft and terminates at step 1814. An inner annular surface 1816 defines bore 1812. Another bore 1818 extends through head 1810 in a distal end direction and is coaxial and contiguous with bore 1812. Bore 1812 has a larger diameter than bore 1818.

The output drive shaft 1800 has an outer annular surface 1820. Threads or grooves 1822 are defined in the outer annular surface 1820 and helix around the length of shaft 1800 starting at distal end 1802 and terminating at a step 1823 of a flange 1824. The flange 1824 is located between head 1810 and center shaft 1801. The diameter of flange 1824 is smaller than the diameter of head 1810. The diameter of the center shaft 1801 is smaller than the diameter of flange 1824. A circular groove 1826 is defined around the circumference of flange 1824 and a step 1827 is also defined around the circumference of flange 1824. Three equally spaced apertures 1828 are defined thru head 1810 and extend between the distal and proximal sides of head 1810. Apertures 1828 receive pins 1726 (FIG. 55) that transfer torque from the planetary gear assembly 1700 to output drive shaft 1800.

A bearing 1830 (FIG. 55) has a distal face that is seated against the lip 1642 (FIG. 53B) of connecting hub 1610. The output shaft head 1810 is positioned in bore 1640 (FIG. 53B) with the distal step 1827 seated against the proximal face of bearing 1830. The center shaft 1801 extends into housing bore 1686. The flange 1824 is surrounded and supported for rotary motion by the bore of bearing 1830. A bevel spring washer 1834 is mounted in housing bore 1686 over center shaft 1801 and is seated against step 1823.

Figure 58:
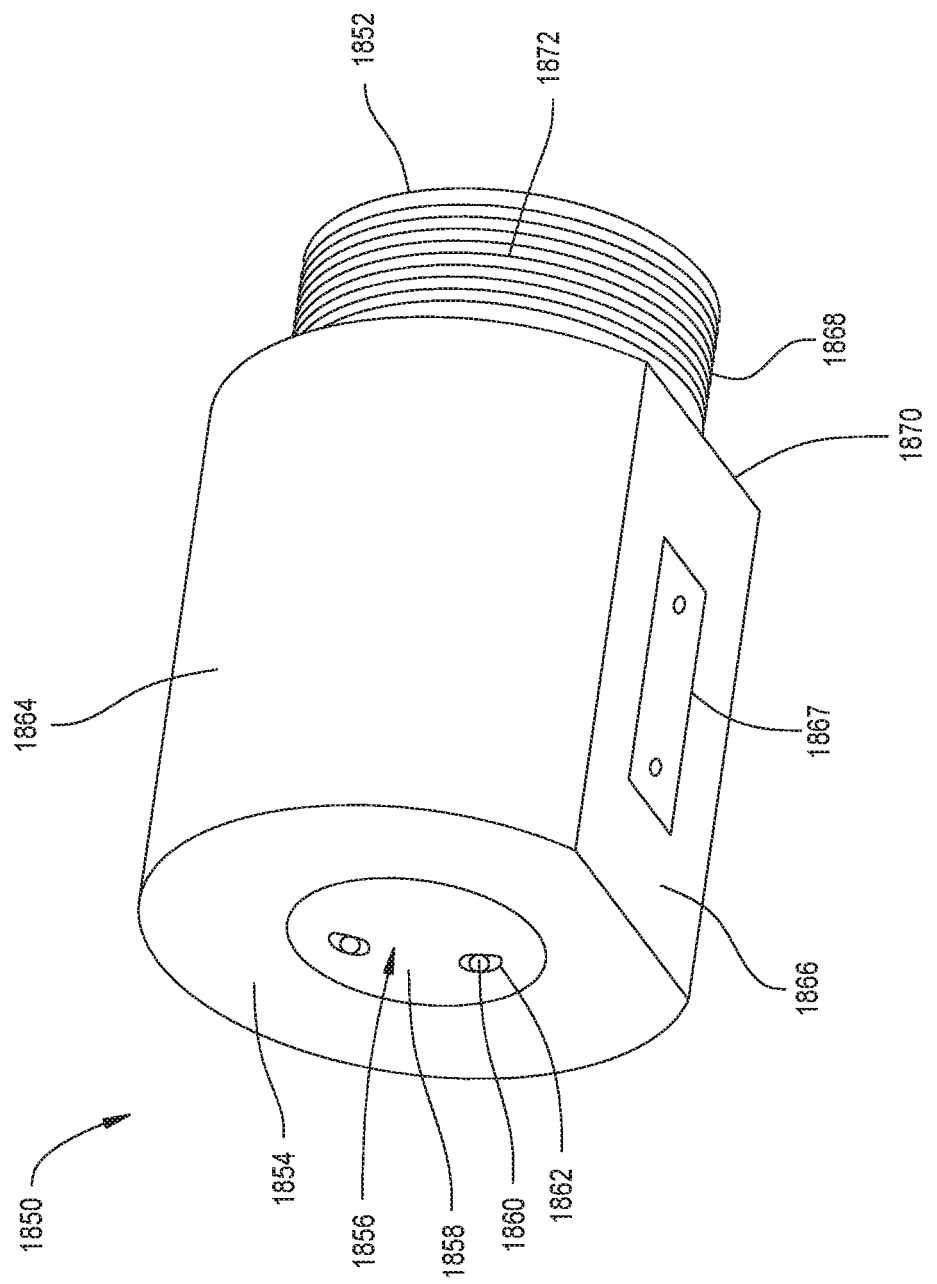
FIG. 58 is a front perspective view of the ball nut.

FIGS. 55 and 58 illustrate features of a ball nut 1850 that is mounted in bore 1640 and around output drive shaft 1800. The ball nut 1850 is a mechanical linear actuator that translates rotational motion to linear motion with little friction and is able to apply or withstand high thrust loads. The ball nut 1850 has a truncated cylindrical shape with a rounded side 1864 and a flat side 1866. Ball nut 1850 has a proximal face 1852 and a distal face 1854. A bore 1856 extends entirely through the ball nut between the proximal and distal faces. Spiral horseshoe shaped raceways 1862 are defined within ball nut 1850. Ball bearings 1860 are disposed in raceways 1862.

The ball nut 1850 is disposed over output drive shaft 1800. Ball bearings 1860 are loaded into raceways 1862 thru an access port 1867. The bearings 1860 circulate thru raceways 1862 and the grooves 1822 of output drive shaft 1800 as the output drive shaft is rotated. The threaded output drive shaft provides a helical raceway for the ball bearings which act as a precision screw. The rotation of output drive shaft 1800 causes a linear translation of ball nut 1850 in either the proximal or distal direction relative to housing 1680 depending upon the rotational direction of output drive shaft 1800.

Ball nut 1850 includes a proximal section 1868 that is defined by a proximal facing step 1870. Proximal section 1868 has a smaller diameter than the remainder of the ball nut. External threads 1872 are defined on proximal section 1868.

FIGS. 55 and 59A-59C show details of a coupler 1900 that is mounted in bore 1640 and to ball nut 1850. Coupler 1900 couples ball nut 1850 to tissue protector sleeve 2000. Coupler 1900 is formed from a single piece of metal and is generally cylindrical in shape. Coupler 1900 has a proximal end 1912 and a distal end 1914. The coupler 1900 has three adjacent cylindrical sections, a base section 1920, a center section 1940 and an end section 1960. The center section 1940 has a diameter that is less than the diameter of base section 1920. End section 1960 has a diameter that is less than the diameter of center section 1940.

The base section 1920 has an outer annular surface 1922 and a bore 1924 that is defined by an inner annular surface 1925. Bore 1924 extends from proximal end 1912 in a distal direction partially into base section 1920 terminating at the internal wall 1926. Wall 1926 is perpendicular to inner annular surface 1925. Four elongated slots 1928 are defined in the outer annular surface 1922 and extend the entire length of base section 1920. The slots 1928 are spaced equidistant apart around the circumference of base section 1920. An arcuate rectangular shaped opening 1930 is located on one side of base section 1920 and faces into bore 1924.

A circumferential lip 1932 extends outwardly from the junction of center section 1940 and end section 1960. Another bore 1942 is defined by an inner annular surface 1944. Bore 1942 extends within the base, center and top sections in a distal direction from wall 1926 and terminates at the internal wall 1946. Wall 1946 is perpendicular to inner annular surface 1944. Bore 1942 is contiguous with bore 1924.

The end section 1960 has a bore 1962 that is defined by an inner annular surface 1964. Bore 1962 extends from distal end opening 1966 in a proximal direction and terminates at wall 1946. Bore 1962 is coaxial and contiguous with bore 1942. An angled nose 1968 is formed in end section 1960. Nose 1968 angles inwardly from the outer surface of end section 1960 and terminates at opening 1966. A rectangular shaped recess 1970 is formed in nose 1968 and has a bottom wall 1972. A threaded aperture 1974 extends between the bottom wall 1972 and inner annular surface 1964 opening into bore 1962. A rim 1976 extends into aperture 1974 from inner annular surface 1964.

Ball nut 1850 and output shaft 1800 are disposed in coupler bore 1924. The ball nut distal wall 1854 seated against the coupler internal wall 1926. The ball nut flat section 1866 faces toward opening 1924. The access port 1867 is accessed through opening 1924. Ball nut 1850 is affixed to coupler 1900 by suitable methods such as by welding or by using fasteners. The output shaft 1800 extends into coupler bore 1942 with the output shaft distal end 1804 spaced slightly away from internal wall 1946.

A bevel spring washer 1980 (FIG. 55) is mounted over a breech 1982. The breech 1982 has internal threads (not shown) that mate with the external threads 1872 of ball nut 1850. Breech 1982 surrounds the ball nut proximal section 1868 and extends over the proximal face 1852 and retains the bevel spring washer 1980 to ball nut 1980. Bevel spring washer 1980 is seated between the distal face 1852 and breech 1982.

Turning to FIG. 43, the housing 1680 is mounted over coupler 1900 such that the coupler 1900 resides within housing bore 1686. Threaded holes 1988 extend thru housing 1680 and are aligned over slots 1928. Screws 1990 are fastened in holes 1988 such that the ends of the screws 1990 extend into and are located within slots 1928, but are not touching the bottom of slots 1928. During use, coupler 1900 moves linearly within bore 1686. Screws 1990 disposed in slots 1928 allow linear motion of coupler 1900, but prevent rotation of coupler 1900 relative to housing 1680.

Figure 60:
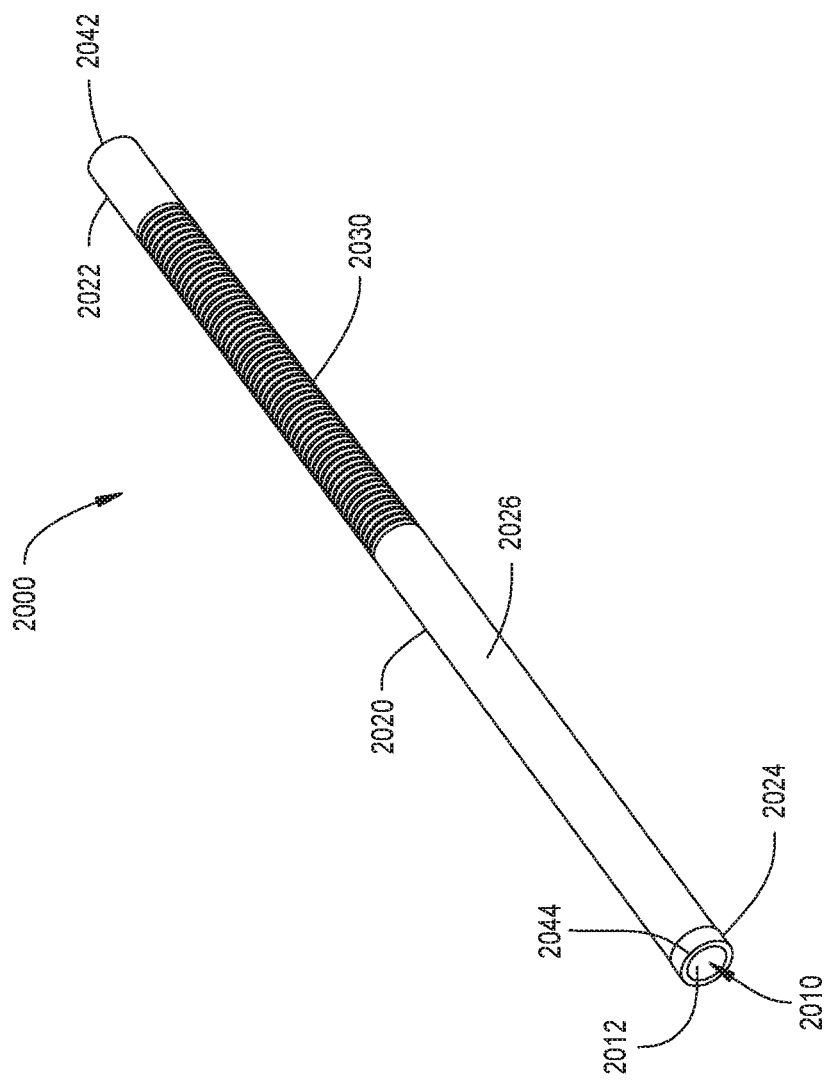
FIG. 60 is a front perspective view of the tissue protector sleeve.

With reference to FIG. 60, features of tissue protector sleeve 2000 are now described. The tissue protector sleeve 2000 has an elongated rod shape. Tissue protector sleeve 2000 is formed with a hollow interior passage 2010 that is defined by an interior circumferential wall or surface 2012. The passage 2010 extends through the entire length of tissue protector sleeve 2000. The tissue protector sleeve 2000 has a center section 2020, a proximal end 2022, a distal end 2024 and an outer surface 2026. An opening 2042 is located at proximal end 2022 and an opening 2024 is located at distal end 2024. A series of parallel grooves 2030 are defined on a portion of outer surface 2026 between the center section 2020 and the proximal end 2022. The grooves 2030 are oriented perpendicular to the longitudinal axis of sleeve 2000.

Figure 57B:
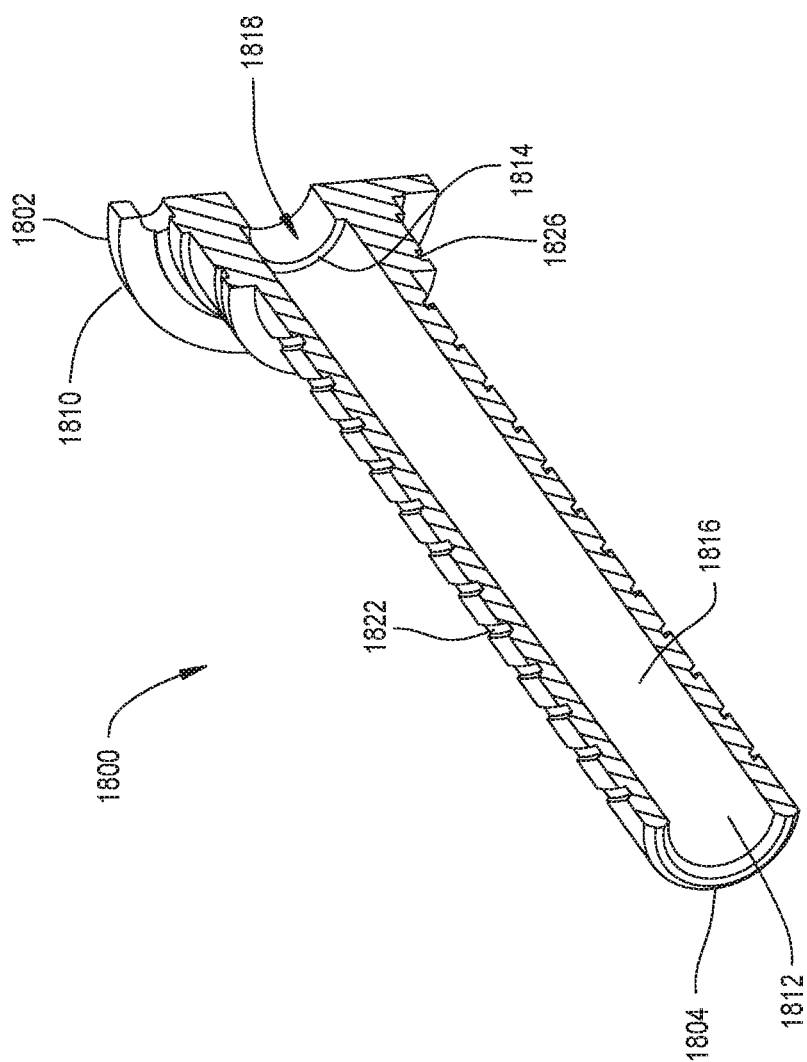
FIG. 57B is a front perspective cross-sectional view of the output drive shaft.

The tissue protector sleeve 2000 is positioned for sliding movement within coupler bores 1942 and 1961 (FIG. 59C) and within output drive shaft bore 1812 (FIG. 57B). In particular, the proximal portion of tissue protector sleeve 2000 is seated in output drive shaft bore 1812 and the center section 2020 is positioned within coupler bores 1942 and 1961. The outer surface 2026 of tissue protector sleeve 2000 is supported by inner annular surface 1964 (FIG. 59C) for sliding motion within bore 1962. The proximal end 2022 of the tissue protector sleeve is received into coupler distal opening 1966 (FIG. 43).

The drill bit 1500 (FIG. 43) is received in sleeve opening 2044 and extends thru bore 2010. The proximal drive head 1520 (FIG. 51) is received within input drive shaft D-shaped bore 1252 and bore 1254 (FIG. 51). The outer circumferential surface of the drill bit 1500 is surrounded by the inner circumferential surface 2012 of the tissue protector sleeve 2000. The tissue protector sleeve 2000 can slide in a longitudinal direction relative to drill bit 1500.

Figure 61:
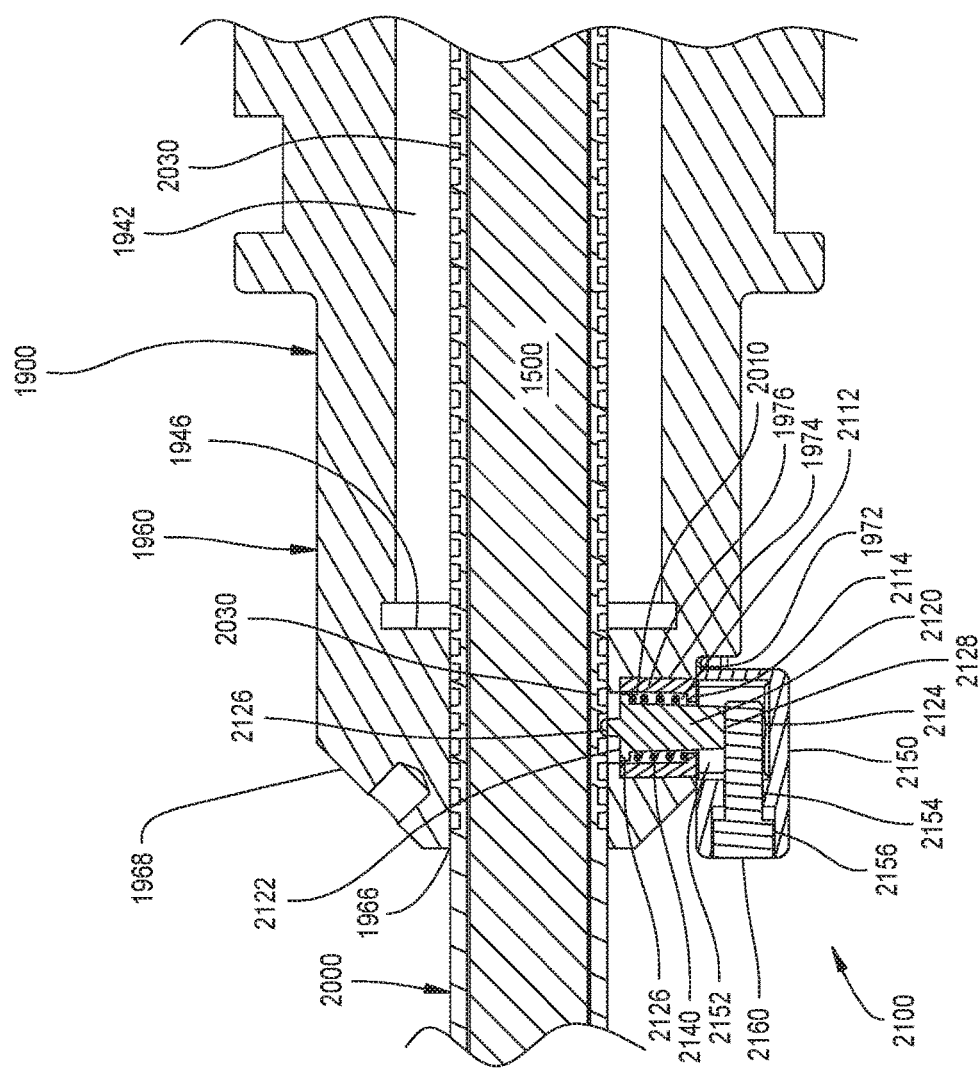
FIG. 61 is an enlarged side cross-sectional view of the second release mechanism and the distal portion of the retracting sleeve mechanism illustrating the relative orientation of the components.

A second release mechanism 2100 is illustrated with reference to FIG. 61. The second release mechanism 2100 is mounted to the nose 1968 of end coupler section 1960. Second release mechanism 2100 includes a barrel 2110 that is screwed into threads 1976 of aperture 1974. Threads (not shown) are defined on the exterior surface of barrel 2110. Barrel 2110 has a hollow cylindrical shaped interior cavity 2112 with and a lower circumferential rim 2114 that protrudes into cavity 2114 at the end of barrel 2110.

A detent arm 2120 and coil spring 2140 are mounted in cavity 2112. Specifically, the detent arm 2120 has a tapered cylindrical shape with an inner end 2122 and an outer end 2124. The inner end 2122 has a larger diameter that the outer end 2124. An annular flange 2126 surrounds inner end 2122. A detent finger 2126 extends away from the inner end 2122. Detent finger 2126 is dimensioned so as to fit into the sleeve grooves 2030. A threaded hole 2128 extends through detent arm 2120 at outer end 2124. The coil spring 2140 is mounted around the detent arm 2120. The coil spring 2140 has an upper end that abuts flange 2126 and a lower end that abuts rim 2114.

The coil spring 2140 biases the detent arm towards tissue protector sleeve 1900 and when the detent finger 2126 is aligned with one of the sleeve grooves 2030, urges the detent finger 2126 to be seated in the corresponding aligned groove 2030.

A knob 2150 is connected to detent arm 2120. Knob 2150 is positioned in recess 1970 and rests on the bottom wall 1972. Knob 2150 is generally rectangular in shape and can be formed from injection molded plastic. Knob 2150 has an internal chamber 2152 that faces bottom wall and an internal bore 2154 that intersects with and is perpendicular to chamber 2152. A counter-bore 2156 extends from the distal side of the knob and terminates at the intersection with internal bore 2154. Counter-bore 2156 is coaxial with internal bore 2154.

Knob 2150 is held to detent arm 2120 by a screw 2160. Screw 2160 extends through counter-bore 2156, internal bore 2154 and is received into threaded hole 2128. The head of screw 2160 is seated in counter-bore 2156 such that the distal face of knob 2150 and the head of the screw are flush.

The detent finger 2126 is normally seated, due to the bias of coil spring 2140, in a corresponding aligned groove 2030. In this position, the tissue protecting sleeve 2000 is connected or locked to the combination of coupler 1900 and ball nut 1850 by the second release mechanism 2100 such that linear movement of the coupler 1900 in a proximal or distal direction results in a like movement of tissue protecting sleeve 2000 in respective proximal or distal directions.

A medical practitioner grasps the distal portion of knob 2150 and move the distal portion of the knob towards or away from coupler nose 1968. Movement of the distal portion of the knob towards or away from coupler nose 1968 results in a lever arm force being applied to detent arm 2120 that moves the detent arm 2120 away from sleeve 2000 and also moves detent finger 2126 out of engagement with grooves 2130. Coil spring 2140 is also compressed by the lever arm force. In this position, the tissue protector sleeve 2000 is free to slide relative to both drill bit 1500 and coupler 1900.

When the distal portion of knob 2150 is released, spring 2140 urges the detent finger 2126 to be seated or engaged with a corresponding aligned sleeve groove 2030. This locks tissue protecting sleeve 2000 to the combination of coupler 1900 and ball nut 1850.

Release mechanism 2100 allows the practitioner to connect and disconnect the tissue protector sleeve from coupler 1900. This allows sliding movement of tissue protector sleeve 2000 relative to drill bit 1500.

The remaining components of rotary surgical drill 1100 including controller 450 and the electrical connections shown in the electrical schematic (FIG. 13) are the same as previously described for rotary surgical drill 100 except that the solenoid 252 and digital caliper 400 have been omitted. Controller 450 controls the operation of braking mechanism 1150.

C. Operation

Figure 62A:
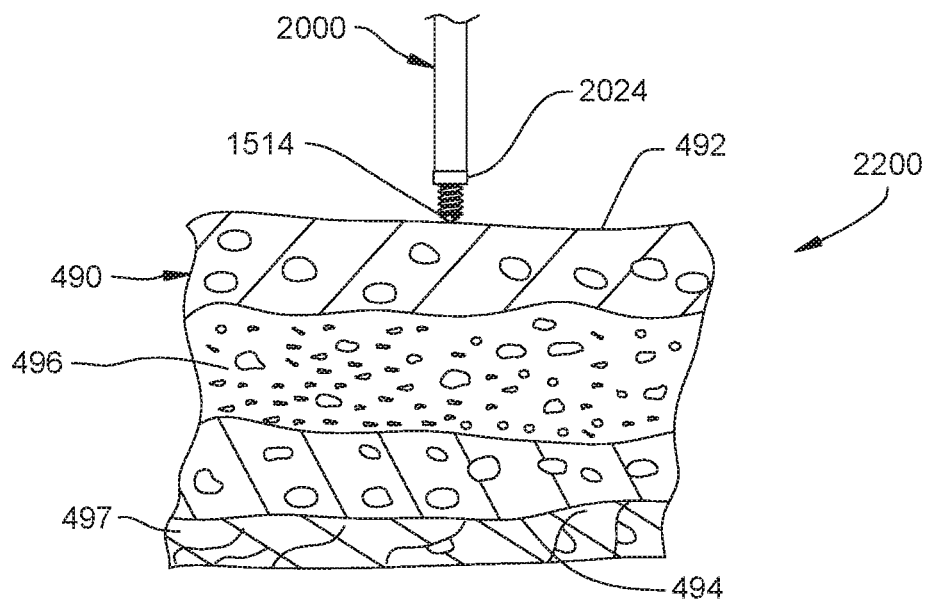
FIG. 62A is a side cross-sectional view of the tissue protector sleeve and drill bit of FIG. 42 prior to the start of drilling into a bone.

FIG. 62A illustrates the rotary surgical drill 1100 being used at a surgical site 2200. The medical practitioner grasps handle 104 and directs the drill bit tip 1514 to the surgical site. Drill bit 1500 is used to drill one or more bores into a bone.

Figure 44A:
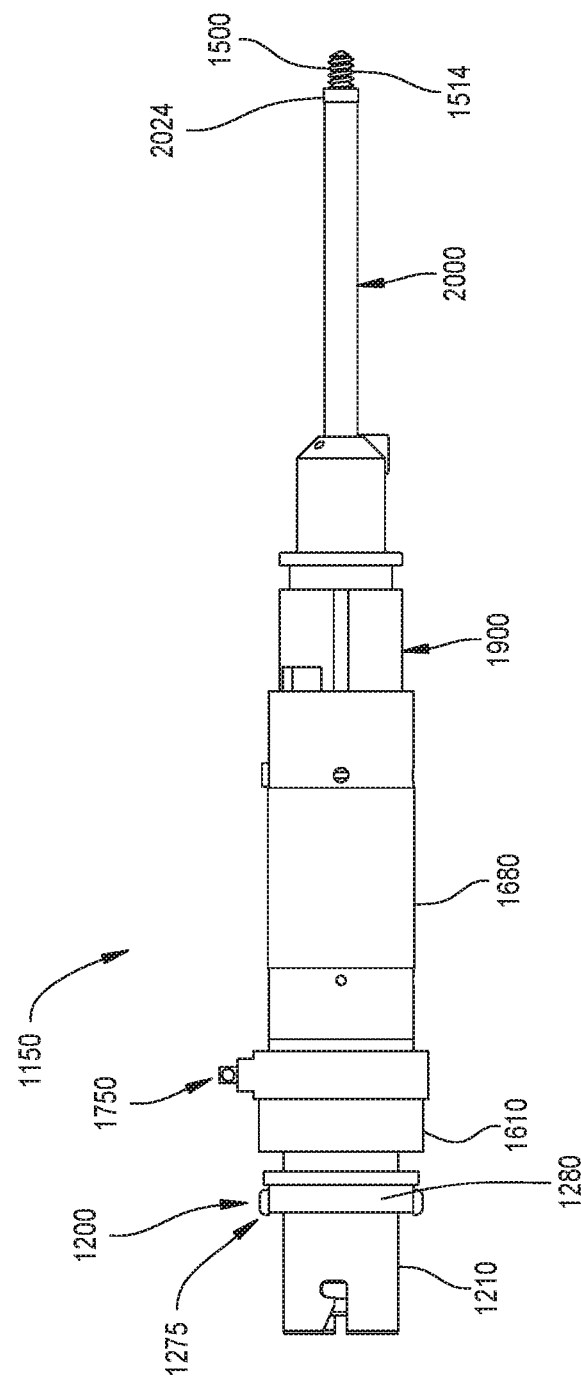
FIG. 44A is a right side view of the brake mechanism of FIG. 26 with the retracting sleeve mechanism in a fully extended position.
Figure 44B:
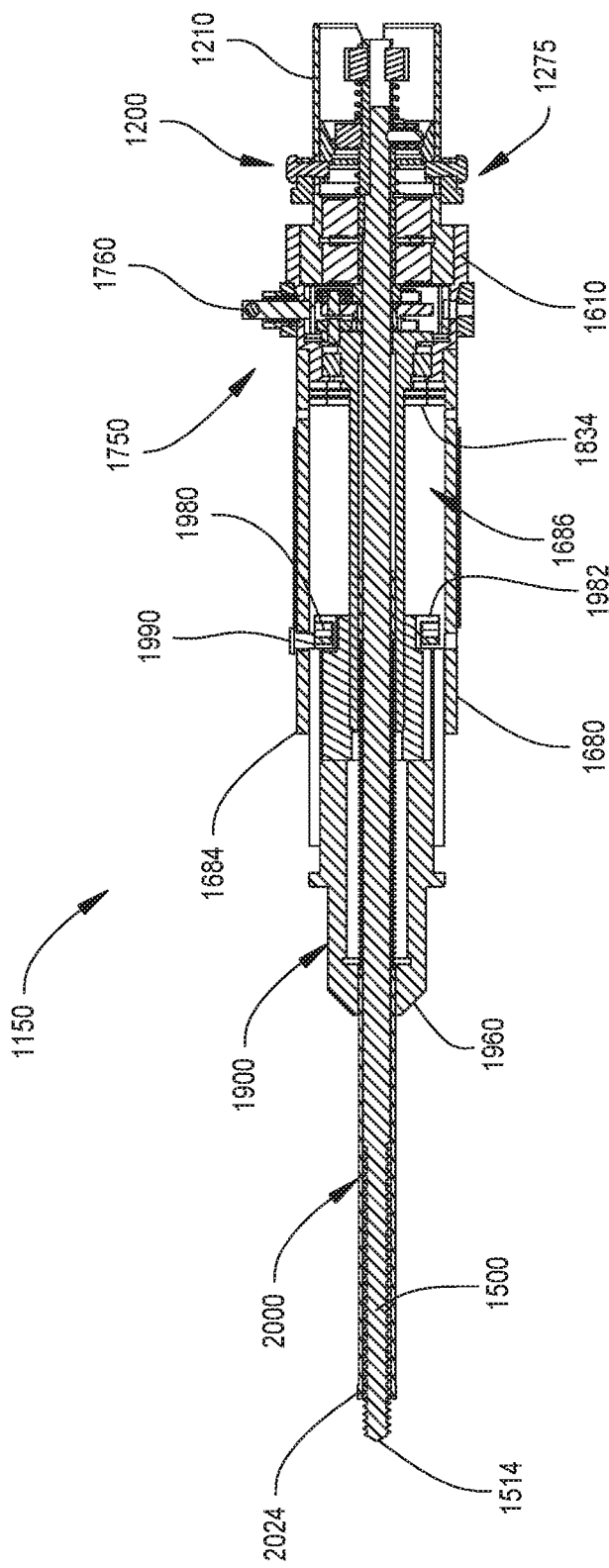
FIG. 44B is a side cross-sectional view of the brake mechanism of FIG. 26 with the retracting sleeve mechanism in a fully extended position.

With reference to FIGS. 44A, 44B and 55, the rotary surgical drill 1100 is initially prepared for drilling a bone bore by the medical practitioner attaching chuck assembly 1200 to handpiece 102 (FIG. 42) and attaching a drill bit 1500 to chuck assembly 1200 using drill bit retainer assembly 1275.

Next, the first release mechanism 1750 is set to disconnect the output drive shaft 1800 from input drive shaft 1240. The medical practitioner pulls upwardly on handle 1779 resulting in the compression of coil spring 1760 and the piston inner end 1762 being removed from one of release ring bores 1742. In this position, ring gear 1730 is free to rotate relative to connecting hub 1610 such that the rotation of the input drive shaft 1240 only results in the rotation of ring gear 1730 and the output drive shaft 1800 is disconnected from the input drive shaft 1240. Also, in this position the combination of the coupler 1900 and the ball nut 1850 are free to slide in a proximal or distal direction relative to housing 1680.

Figure 59A:
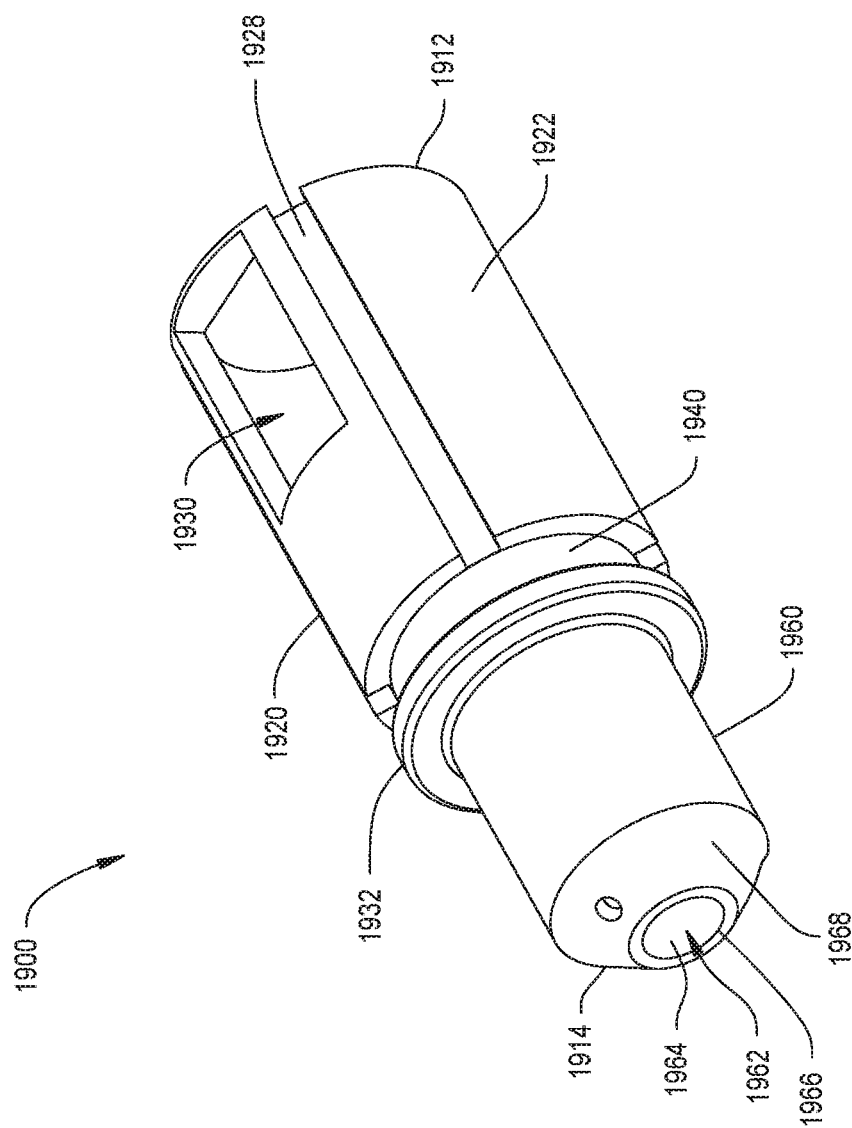
FIG. 59A is a front perspective view of the coupler.
Figure 59B:
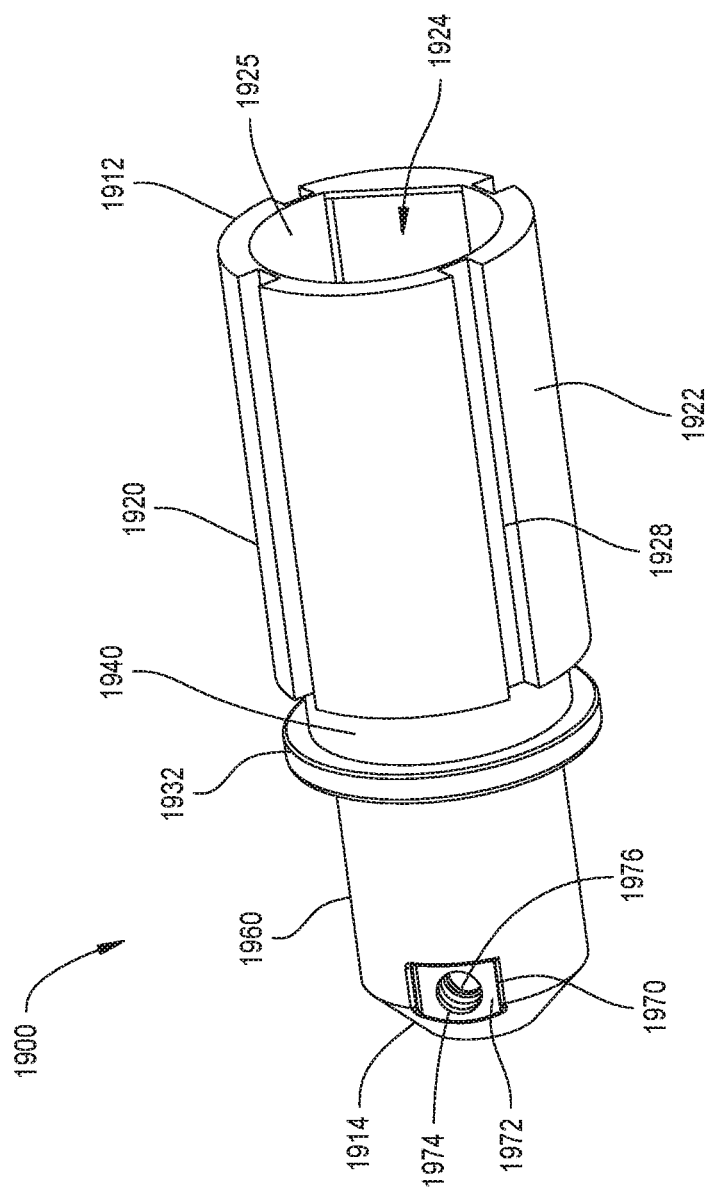
FIG. 59B is a rear perspective view of the coupler.
Figure 59C:
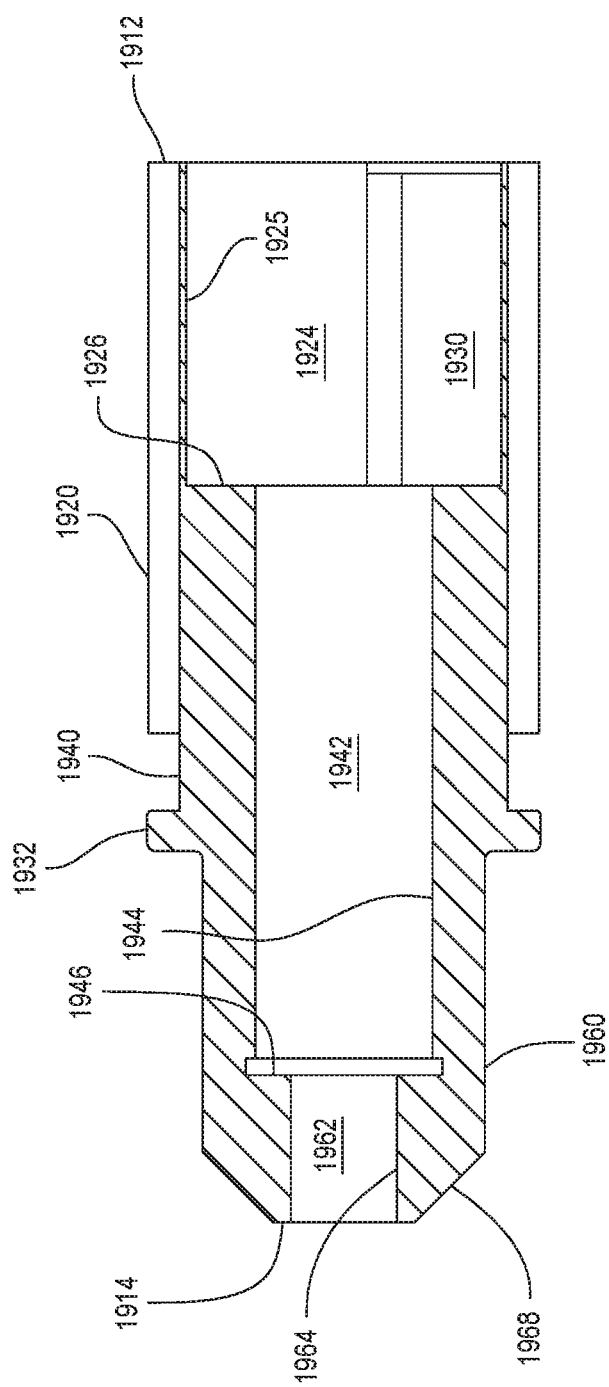
FIG. 59C is a side cross-sectional view of the coupler.

The medical practitioner grasps the coupler end section 1960 and manually moves the coupler 1900 to a distal most position or fully extended position as shown in FIGS. 44A and 44B. The movement of coupler 1900 in the distal direction is limited by the abutment of bevel spring washer 1980 against screws 1990. The movement of coupler 1900 is guided by the ends of screws 1990 tracking within coupler slots 1928 (FIG. 59A).

With the coupler 1900 fully extended, the medical practitioner releases handle 1779. This causes spring 1780 to displace piston 1760 so the piston inner end 1762 is urged through one of connecting hub holes 1634 and into one of release ring bores 1742. The piston end 162 seats against terminal wall 1744 (FIG. 56). In this position, piston 1760 prevents the rotation of ring gear 1730 relative to connecting hub 1610 such that the rotation of input drive shaft 1240 results in the like rotation of output drive shaft 1800. The input drive shaft 1240 is now re-connected to output drive shaft 1800.

The medical practitioner next prepares rotary surgical drill 1100 for drilling a bone bore by positioning the tissue protector sleeve 2000 relative to drill bit 1500 such that a desired length of the drill bit tip 1514 extends beyond the sleeve distal end 2024. The tissue protector sleeve 2000 is positioned using second release mechanism 2100 (FIG. 61). With additional reference to FIG. 61, the medical practitioner grasps the distal portion of knob 2150 and moves the distal portion of the knob towards or away from coupler nose 1968. The movement of the distal portion of the knob towards or away from coupler nose 1968 results in a lever arm force being applied to detent arm 2120. This force moves the detent arm 2120 away from sleeve 2000 and also moves detent finger 2126 out of engagement with grooves 2130. The tissue protector sleeve 2000 is manually grasped and moved in either a distal or proximal direction relative to the drill bit 1500 such that a desired length of the drill bit tip 1514 extends beyond the sleeve distal end 2024. In one embodiment, the tissue protector sleeve 2000 is positioned such that the distal end 2024 is slightly drawn back from the drill bit distal tip 1514 causing only the distal tip 1514 to be exposed as seen in FIG. 62A.

The medical practitioner releases the distal portion of knob 2150. Spring 2140 then urges detent finger 2126 into engagement with a corresponding aligned sleeve groove 2030 This locking the tissue protecting sleeve 2000 to the combination of coupler 1900 and ball nut 1850. The rotary surgical drill 1100 is now ready to drill a bone bore With additional reference to FIGS. 13 and 62A, the surgical drill 1100 is used at a surgical site 2200 to form a bore in a bone. The drill bit tip 1514 is positioned against the proximal side 492 of the bone 490 where a bone bore is to be formed. Also initially, the drill bit 1500 is not subjected to any axial loading.

The drill bit 1500 is forced downwardly by the medical practitioner in an axial direction. After the drill bit 1500 is so positioned, the rotary drill 1100 is actuated in a forward or clockwise rotation.

Figure 62B:
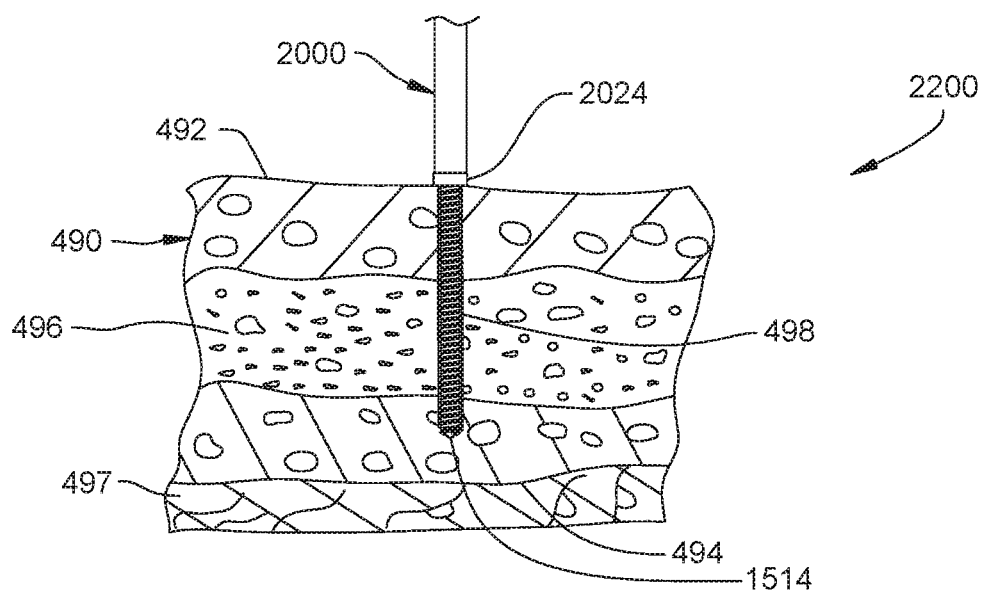
FIG. 62B is a side cross-sectional view of the tissue protector sleeve and drill bit of FIG. 42 during formation of a bone bore in a bone.
Figure 62C:
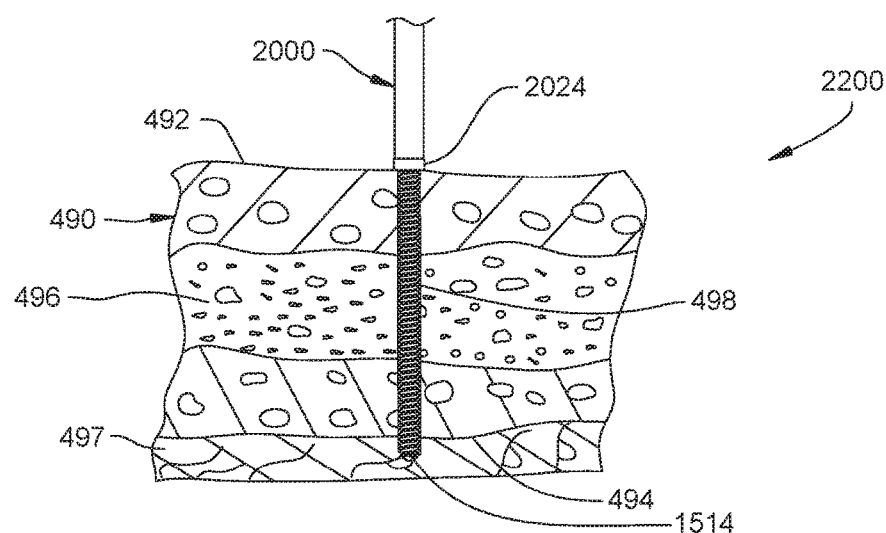
FIG. 62C is a side cross-sectional view of the tissue protector sleeve and drill bit of FIG. 42 after the drill bit has penetrated through the bone.

The combination of the rotating drill bit and the axial load placed on the drill bit results in the cutting edges of the drill bit tip 1514 cutting the bone 490 so as to form a bore 498 (FIG. 62B). Sensor 464 operates as described with the previous versions of the invention.

Referring to FIG. 61B, as the drill bit tip 1514 enters the bone, the distal end 2024 of the tissue protector sleeve 2000 abuts the proximal side 492 of bone 490 limiting the forward movement of drill bit 1500.

At the same time that the drill bit 1500 is rotated by motor 122, the motor 122 drives the retracting sleeve mechanism 1600. Specifically, motor 122 rotates input drive shaft 1240 driving the first and second stages of planetary gear assembly 1700. This results in the rotation of output drive shaft 1800. The rotation of the output drive shaft 1800 causes a linear translation of the ball nut 1850 and the attached coupler 1900 in the proximal direction relative to housing 1680. The coupler 1900 and ball nut 1850 retract into housing bore 1686. Because the tissue protector sleeve 2000 is coupled to coupler 1900 by the second release mechanism 2100, translation of the coupler 1900 in the proximal direction causes the tissue protector sleeve 2000 to retract away from the drill bit tip 1514.

In practice the ball screw rotates at a speed of between 50 to 200 RPM. Often this rotation is between 75 and 125 RPM. The pitch of ball screw is selected so that the screw causes the sleeve 2000 to retract at a speed of between 2.5 mm/sec. to 8.0 mm/sec. More often, the components forming the retraction mechanism are set so that screw causes the sleeve to retract at a rate of between 3.5 mm/sec. and 6.5 mm/sec.

Therefore, as the bone bore 498 is formed, the length of the drill bit 1500 exposed or extending beyond the distal end 2024 of the tissue protector sleeve increases. During drilling of the bone bore, the tissue protector distal end 2024 remains static against the bone 490 while the handpiece, chuck assembly 1200 and housing 1680 move in a distal direction relative to coupler 1900 during drilling.

Figure 45A:
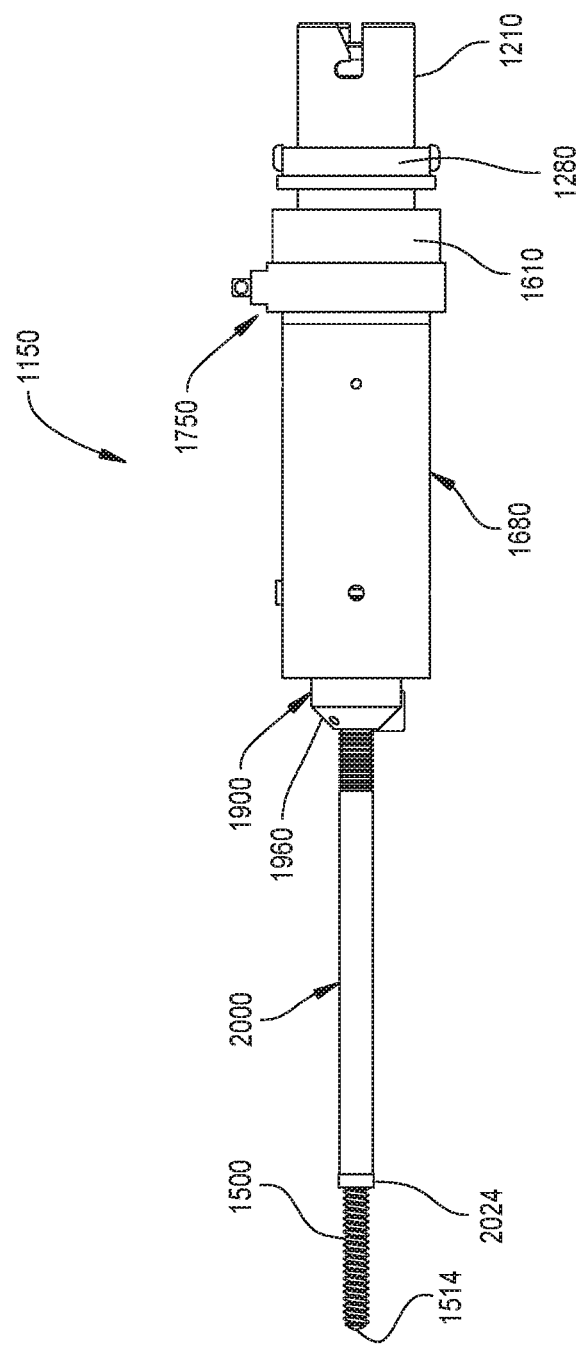
FIG. 45A is a left side view of the brake mechanism of FIG. 26 with the retracting sleeve mechanism in a fully retracted position.
Figure 45B:
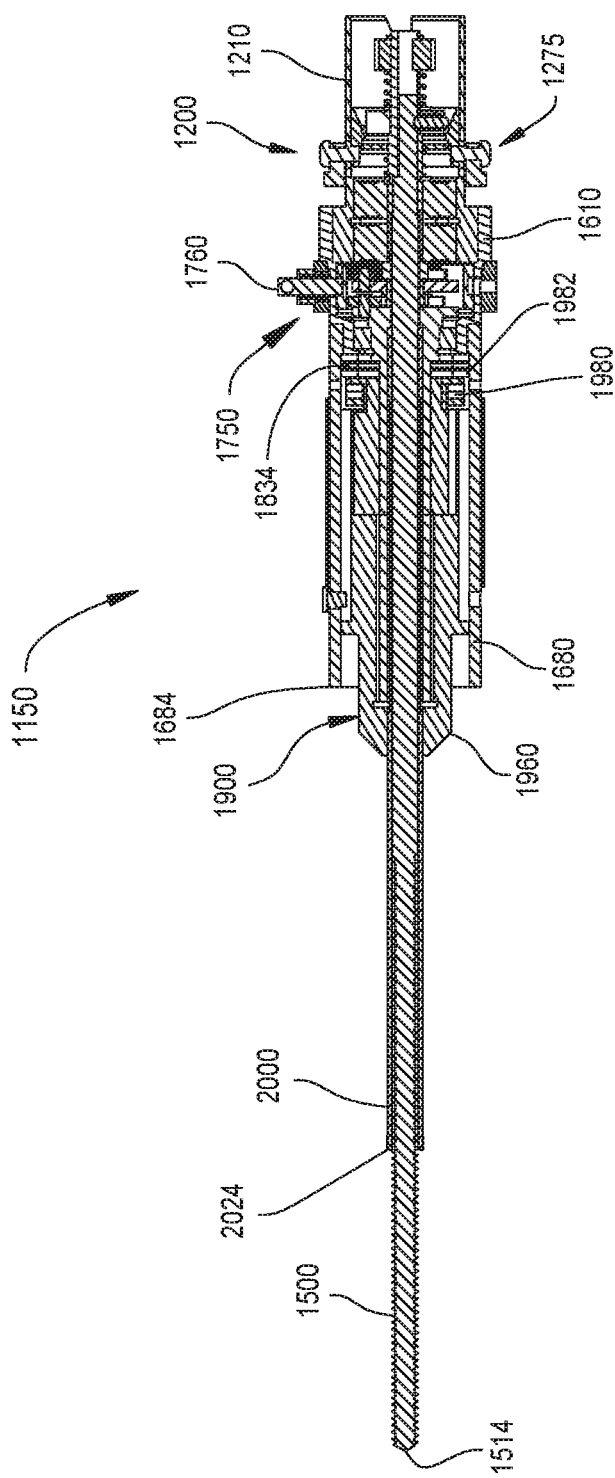
FIG. 45B is a side cross-sectional view of the brake mechanism of FIG. 26 with the retracting sleeve mechanism in a fully retracted position.

Referring to FIGS. 45A and 45B, the retraction of the tissue protecting sleeve 2000 and coupler 1900 into the housing bore 1686 is limited by the abutment of the proximal face of breech 1982 against the bevel spring washer 1834. As shown in FIGS. 45A and 45B, the coupler 1900 is in a proximal most position or fully retracted into housing 1680 such that only a portion of coupler end 1960 extends beyond the distal end 1684 of the housing. In this position, the maximum length of the distal end of the drill bit 1500 extending beyond the distal end 2024 of the tissue protecting sleeve is revealed.

With additional reference to FIGS. 13 and 61C, continued rotation of the drill bit and axial loading causes the drill bit tip 1514 to penetrate through the bone and bone marrow 496 and to approach the distal side 494 of bone 490. Eventually, the drill bit tip 1514 cuts through the distal side 494 of bone 490. As described above with respect to the other versions of the invention, sensor 464 detects the change in current draw and asserts a signal to controller 450.

In response to the change in current drawing being greater than the threshold change in current level, braking mechanism 1150 through processor 452 turns off motor 122 through motor driver circuit 462. When the motor 122 is turned off, the tissue protector sleeve 200 will no longer be retracted. This prevents further advancement of the drill bit 1500. Further the turning off of motor 122 also stops the rotation of the drill bit 1500. Collectively, the stopping of these movements prevents further advancement of the drill bit beyond the distal side 494 of the bone.

After the braking mechanism 1150 has stopped advancement of the drill bit 1500, the length of the drill in the bone bore 498 is equal to the distance between the distal end 2024 of the tissue protector sleeve and the drill bit tip 1514. This length is the approximate length that is required for a bone screw that is to be inserted into the bone bore.

The medical practitioner may pull the drill bit 1500 out from the bone bore 498. However, if the bone bore is deep, the frictional force imposed by the bone may significantly impede the withdrawal of the bit 1500. To break this frictional force, drill 1100 can be actuated drive the bit in either the forward or reverse direction.

Should the practitioner choose to actuate drill 1100 so the bit 1500 is rotated in the reverse direction, brake mechanism 1150 simultaneously advances the sleeve 2000 in the distal direction. This repositions the sleeve 2000 so that the distal end of the sleeve is located relatively close to the tip 1514 of the drill bit 1500. Thus an advantage of driving the drill 1100 in the reverse direction to withdraw the bit, is that at the end of the process sleeve 2000 is essentially repositioned to again function as stop that prevents overdrilling of the next bore.

With the drill bit 1500 removed from the bone bore, the medical practitioner can place bone screws adjacent the drill bit portion that extends beyond the distal end 2024 of the tissue protector sleeve and visually select the bone screw that matches the depth of the bone bore. Alternatively, the medical practitioner can use a measurement scale to measure the drill bit portion that extends beyond the distal end 2024 of the tissue protector sleeve.

In some procedures, it may be necessary to use drill 1100 to drill plural bores in the patient. Between the drilling of two bore, it is often desirable to reset sleeve 2000 to the extended position. One means by which sleeve 2000 may be so extended is, once the bit 1500 is removed from the patent, reengaging the release mechanism and then, while the bit is out of the patient, driving the drill in reverse. This results in release mechanism 1600 advancing the sleeve 2000 distally forward over the bit 1500. This method assumes that the release mechanism 1600 is engaged with the planetary gear assembly.

Alternatively, when the handle 1779 is in the disengaged state, sleeve 2000 can simply be manually extended over the drill bit 1500. Once the sleeve 2000 is so positioned, handle 1779 is reset to the engaged state. Drill 1100 is again ready for use.

Before the medical practitioner can use rotary surgical drill 1100 to form another bore, the braking mechanism 1150 is reset to allow rotation of motor 122 in a forward direction. In one embodiment, processor 452 allows forward rotation of motor 122 after sensing depression of reverse trigger switch 117. In another embodiment, processor 452 allows forward rotation of motor 122 after detecting a certain sequence of depression of the trigger switches 116, 117. For example, processor 452 can reset braking mechanism 1150 after detecting the simultaneous depression of both trigger switches 116 and 117. In an additional embodiment, a separate switch (not shown) can be provided to reset braking mechanism 1150.

The braking mechanism 1150 of the present invention using retracting sleeve mechanism 1600 allows a drill bit 1500 that is forming a bone bore to stop further penetration beyond the bone after the initial penetration through the bone, thereby preventing damage to any tissue adjacent the distal side of the bone. After the drill bit 1500 has cut through the bone, the drill bit 1500 stops rotating in a forward direction thereby avoiding cutting any tissue adjacent the distal side of the bone bore.

The above description is directed to specific versions of the invention. Other versions of the invention may have features different from what has been described. For example components from the various versions of the inventions may be combined.

Further sensors other than sensors that simply monitor changes in current draw may be used to provide the signal indicating that the drill bit penetrated the side of the bone not visible to the practitioner. These sensors include force sensors that monitor the force applied when pushing the drill bit forward. A signal indicating the sudden drop off in applied force would be interpreted as an indication that the drill bit has completely penetrated the bone. Still another type of sensor that may be used to provide a signal indicative of drill bit penetration is a sensor that monitors the torque applied by the drill bit. Sensors other than sensors that operate by measuring current draw can provide a measure of drill bit torque. A signal from this type of sensor indicating that the quantity of torque output by the drill bit has significantly dropped in a short amount of time is interpreted as an indication that the drill bet has fully penetrated the bone. Still another type of sensor that may be employed to provide an indication of drill bit penetration is an accelerometer. This type of sensing may be useful because, as the drill bit penetrates the bone, there is a rapid acceleration of the bit and handpiece 102. Accordingly, the signal from the accelerometer could be used to provide this indication that the drill bit has penetrated bone.

The above sensors are often used in versions of this invention wherein the handpiece motor is a motor other than an electrically driven motor. These motors include pneumatic and hydraulically driven motors.

In some versions of the invention, the stop at the distal end of the telescoping rod 360 may not be a ring 378 that extends around the drill bit. Instead the stop may be a small tab that projects from the rod 360. Alternatively the stop may simply be the distal end of the rod 360.

A device other than a solenoid may move the brake between the engaged and disengaged states. These devices include stepper motors. In these versions of the invention, the actuator in addition to moving the brake from the disengaged to the engaged state can be run in reveres to move the brake from engaged to the disengaged state. This would eliminate the need to provide a spring or other biasing component to hold the brake in the disengaged state. In still other versions of the invention the spring may normally bias the brake into the engaged state. In these versions of the invention, the solenoid or other actuator, in opposition to the spring force normally holds the brake in the disengaged state. Upon receiving the command signal that the brake is to be set, the actuator releases the force holding the brake. The spring or other biasing component provides the force that drives the brake into engagement with the rack.

In versions of the invention wherein the telescoping member that retracts with the actuation of the motor, this member may not always be a sleeve. In alternative versions of this invention this telescoping member may be a single rod to which a stop is attached. Alternatively, this telescoping member can be plural rods that surround the drill bit. A single stop may be attached to the distal ends of these rods.

Similarly, it should be understood that the direction of movement of the brake from the disengaged state to the engaged state may vary from what has been described. Thus there is no requirement that when the brake is so displaced, the brake move either towards the handle 104 or away from the handle 104. In some versions of the invention, the brake may move along a path of travel that is perpendicular to the top to bottom longitudinal axis through the handle.

Accordingly, it is an object of the appended claims to cover all variations and modifications that come within the true spirit and scope of this invention.

What is claimed is:

1. A surgical drill assembly comprising:
a handpiece with a motor, a chuck attached to the motor for releasably holding a drill bit to the motor so the drill bit can be rotated by the motor;
a telescoping member having opposed proximal and distal ends, a proximal section of the telescoping member moveably mounted to the handpiece to allow the telescoping member to move proximally and distally along the handpiece and a stop attached to the distal end of the telescoping member so as to be located at a distal end of the drill assembly;
a brake assembly is attached to said handpiece, said brake assembly including a member having:
a brake that is moveably attached to said handpiece to move between engaged and disengaged positions with the telescoping member, wherein when the brake is in the engaged position with the telescoping member, said brake stops movement of the telescoping member; and
an actuator, that in response to a command signal, selectively moves said brake from the disengaged position to the engaged position;
wherein the telescoping member comprises a plurality of teeth, and the brake comprises a plunger moveable between the engaged and disengaged positions, such that the plunger is configured to engage the teeth of the telescoping member when the plunger is in the engaged position and the plunger is configured to disengage the teeth of the telescoping member when the plunger is in the disengaged position.

2. The surgical drill of claim 1, wherein:
the handpiece has an end: and
said brake and said actuator are mounted to the handpiece so as to be located adjacent to the end of said handpiece.

3. The surgical drill assembly of claim 1, wherein:
said plurality of teeth of said telescoping member extends proximally to distally along the telescoping member; and
said brake is formed with a tooth dimensioned to, when the brake is in the engaged position seat between said plurality of teeth of said telescoping member.

4. The surgical drill assembly of claim 1 further including the actuator that normally holds the brake in the disengaged position.

5. The surgical drill assembly of claim 1, wherein said actuator is a solenoid.

6. The surgical drill assembly of claim 1, wherein:
a sensor is mounted to said handpiece to monitor when said drill bit penetrates through bone and asserts a sensor signal indicative of when the drill penetrates through bone;
a control circuit is mounted to said handpiece to receive from said sensor the sensor signal indicative of when said drill bit penetrates through bone and, in response to receipt of the sensor signal, asserts the command signal to said actuator that causes said actuator to move said brake from the disengaged position to the engaged position.

7. The surgical drill assembly of claim 6, wherein said motor is an electrically powered motor; and said sensor is configured to monitor when the drill bit penetrates bone by monitoring current draw of said motor.

8. The surgical drill assembly of claim 1, further including a depth gauge mounted to the handpiece to monitor the movement of the telescoping member.

9. A surgical drill assembly comprising:
a handpiece with a motor, a chuck attached to said motor for releasably holding a drill bit to said motor so the drill bit can be rotated by the motor;
a telescoping member having opposed proximal and distal ends, a proximal section of the telescoping member moveably mounted to the handpiece to allow the telescoping member to move proximally and distally along the handpiece and a stop attached to the distal end of the telescoping member so as to be located at a distal end of the drill assembly, where at least a portion of said telescoping member is located proximal to the drill bit and is at least partially contained in the handpiece; and a brake that is moveably attached to said handpiece to move between engaged and disengaged positions with the telescoping member, wherein when the brake is in the engaged position with the telescoping member, said brake stops movement of the telescoping member; and an actuator, that in response to a command signal, selectively moves said brake from the disengaged position to the engaged position;

said motor has a rotor with an axially extending throughbore;

a portion of said telescoping member is slidably disposed in the throughbore of the motor rotor and extends out of a proximal end of the motor rotor; and said brake is mounted to the handpiece so as to be located proximal to the motor so as to engage a portion of the telescoping member that extends proximally from the motor.

10. A surgical drill comprising:

a handpiece with a motor, a chuck attached to the motor for releasably holding a drill bit to the motor so the drill bit can be rotated by the motor;

a telescoping member having opposed proximal and distal ends, a proximal section of the telescoping member moveably mounted to the handpiece to allow the telescoping member to move proximally and distally along the handpiece, the distal end shaped to abut tissue adjacent tissue into which the drill bit bores; and a retraction assembly attached to the telescoping member and capable of, simultaneously with actuation of the motor to rotate the drill bit retracting the telescoping member proximally so the distal end of the telescoping member is retracted proximally away from a distal end tip of the drill bit, wherein said retraction assembly is connected to said motor so that said motor, simultaneously with the rotation of the drill bit, causes the retraction assembly to retract the telescoping member proximally;

wherein the telescoping member is a sleeve that is disposed over the drill bit.

11. The surgical drill assembly of claim 1, wherein the actuator comprises a solenoid configured to be energized and move the plunger to the engaged position where the plunger engages with the plurality of teeth of the telescoping member.

* * * * *

UNITED STATES PATENT AND TRADEMARK OFFICE
CERTIFICATE OF CORRECTION

PATENT NO. : 10,245,043 B2
APPLICATION NO. : 14/991224
DATED : April 2, 2019
INVENTOR(S) : Mark M. Xie Page 1 of 1

It is certified that error appears in the above-identified patent and that said Letters Patent is hereby corrected as shown below:

In the Claims

Column 44, Lines 3-4, Claim 10, Please delete:
"the distal end shaped to abut tissue adjacent tissue into which the drill bit bores"

Signed and Sealed this
Thirteenth Day of August, 2019

Andrei Iancu
*Director of the United States Patent and Trademark Office*